United States Patent
Miyazawa

(10) Patent No.: US 10,945,681 B2
(45) Date of Patent: Mar. 16, 2021

(54) CONTROL DEVICE FOR CONTROLLING TOMOSYNTHESIS IMAGING, IMAGING APPARATUS, IMAGING SYSTEM, CONTROL METHOD, AND PROGRAM FOR CAUSING COMPUTER TO EXECUTE THE CONTROL METHOD

(71) Applicant: CANON KABUSHIKI KAISHA, Tokyo (JP)

(72) Inventor: Nobu Miyazawa, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 956 days.

(21) Appl. No.: 14/899,061

(22) PCT Filed: Jun. 18, 2014

(86) PCT No.: PCT/JP2014/066183
§ 371 (c)(1),
(2) Date: Dec. 16, 2015

(87) PCT Pub. No.: WO2014/203938
PCT Pub. Date: Dec. 24, 2014

(65) Prior Publication Data
US 2016/0128648 A1 May 12, 2016

(30) Foreign Application Priority Data
Jun. 18, 2013 (JP) .................................. 2013-127975

(51) Int. Cl.
*A61B 6/02* (2006.01)
*A61B 6/00* (2006.01)
(Continued)

(52) U.S. Cl.
CPC .............. *A61B 6/025* (2013.01); *A61B 6/461* (2013.01); *A61B 6/463* (2013.01); *A61B 6/465* (2013.01);
(Continued)

(58) Field of Classification Search
CPC ................................ A61B 6/465; G06F 19/00
See application file for complete search history.

(56) References Cited

U.S. PATENT DOCUMENTS 6,418,236 B1 * 7/2002 Ellis .................... G06K 9/00127
382/128
7,292,675 B1 * 11/2007 Li .......................... A61B 6/025
378/116
(Continued)

FOREIGN PATENT DOCUMENTS

| CN | 1661468 A | 8/2005 |
| CN | 1989907 A | 7/2007 |

(Continued)

*Primary Examiner* — Gandhi Thirugnanam
(74) *Attorney, Agent, or Firm* — Canon U.S.A., Inc. IP Division

(57) ABSTRACT

In tomosynthesis imaging for obtaining a tomosynthesis image from a projected image group captured by irradiating an object with X-rays from a plurality of different angles by using an X-ray generation unit and an X-ray detection unit, in association with a process for setting data of a projected image group as a reject, data of a tomosynthesis image generated on the basis of the projected image group is set as a reject.

20 Claims, 29 Drawing Sheets

(51) Int. Cl.
*G16H 40/63* (2018.01)
*G06T 11/00* (2006.01)
*G16H 30/20* (2018.01)

(52) U.S. Cl.
CPC .............. *A61B 6/466* (2013.01); *A61B 6/468* (2013.01); *A61B 6/50* (2013.01); *A61B 6/5205* (2013.01); *A61B 6/5223* (2013.01); *A61B 6/5258* (2013.01); *A61B 6/54* (2013.01); *G16H 40/63* (2018.01); *A61B 6/563* (2013.01); *G06T 11/005* (2013.01); *G16H 30/20* (2018.01)

(56) References Cited

U.S. PATENT DOCUMENTS

| | | | | |
|---|---|---|---|---|
| 8,879,813 | B1* | 11/2014 | Solanki | G16H 30/20 382/128 |
| 10,383,582 | B2* | 8/2019 | Miyazawa | A61B 6/4452 |
| 2005/0111614 | A1* | 5/2005 | Matsuura | A61B 6/032 378/19 |
| 2006/0104412 | A1* | 5/2006 | Kawanabe | A61B 6/469 378/20 |
| 2006/0171573 | A1* | 8/2006 | Rogers | G06K 9/3233 382/128 |
| 2007/0071299 | A1* | 3/2007 | Matsuura | G06T 11/005 382/128 |
| 2009/0003679 | A1* | 1/2009 | Ni | A61B 6/025 382/132 |
| 2009/0208075 | A1* | 8/2009 | Fischer | G06T 7/11 382/128 |
| 2010/0027752 | A1* | 2/2010 | Matsumoto | A61B 6/10 378/115 |
| 2011/0058724 | A1* | 3/2011 | Claus | G06T 11/006 382/132 |
| 2012/0033868 | A1* | 2/2012 | Ren | A61B 6/025 382/131 |
| 2012/0050576 | A1* | 3/2012 | Yamada | G03B 42/02 348/239 |
| 2016/0120495 | A1* | 5/2016 | Miyazawa | A61B 6/54 378/21 |
| 2016/0128648 | A1* | 5/2016 | Miyazawa | A61B 6/025 378/21 |
| 2016/0128649 | A1* | 5/2016 | Miyazawa | A61B 6/025 378/21 |
| 2016/0135760 | A1* | 5/2016 | Miyazawa | A61B 6/465 378/25 |
| 2016/0183898 | A1* | 6/2016 | Cormican | A61B 6/0414 378/37 |

FOREIGN PATENT DOCUMENTS

| | | |
|---|---|---|
| EP | 3011904 A1 | 4/2016 |
| JP | 2000-46760 A | 2/2000 |
| JP | 2006-218139 A | 8/2006 |
| JP | 2010-179092 A | 8/2010 |
| JP | 2010-246862 A | 11/2010 |
| JP | 2011-87619 A | 5/2011 |
| JP | 2012-50566 A | 3/2012 |
| JP | 2013-39197 A | 2/2013 |
| JP | 2013-144097 A | 7/2013 |
| JP | 2015-000322 A | 1/2015 |
| WO | 2014/203936 A1 | 12/2014 |
| WO | 2014/203940 A1 | 12/2014 |

* cited by examiner

FIG. 8

| EXAM ID | PATIENT ID | PATIENT NAME | GENDER | DATE OF BIRTH | AGE |
|---|---|---|---|---|---|
| O001 | P333 | SABURO YAMADA | MALE | 11/11/1981 | 29 |
| O002 | P222 | JIRO YAMADA | MALE | 2/2/2002 | 7 |
| O003 | P111 | TARO YAMADA | MALE | 1/10/2001 | 8 |
| O004 | P777 | HANAKO YAMADA | FEMALE | 7/7/1977 | 12 |
| O005 | P123 | ICHIRO YAMADA | MALE | 3/3/2003 | 3 |
| O006 | P444 | SHIRO YAMADA | MALE | 4/4/1964 | 45 |
| O007 | P555 | GORO YAMADA | MALE | 5/5/1955 | 54 |
| O008 | P666 | ROKURO YAMADA | MALE | 6/6/1976 | 33 |

FIG. 20
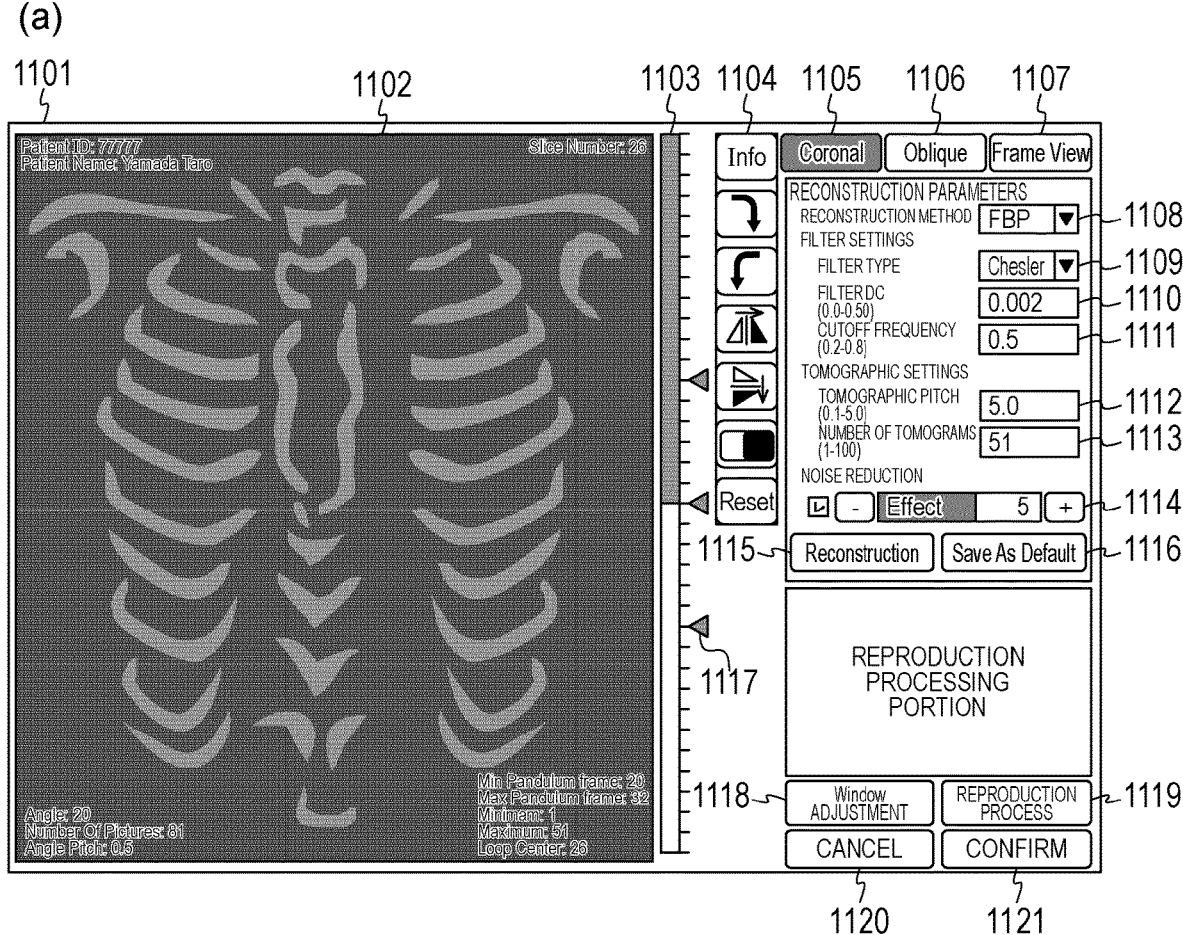
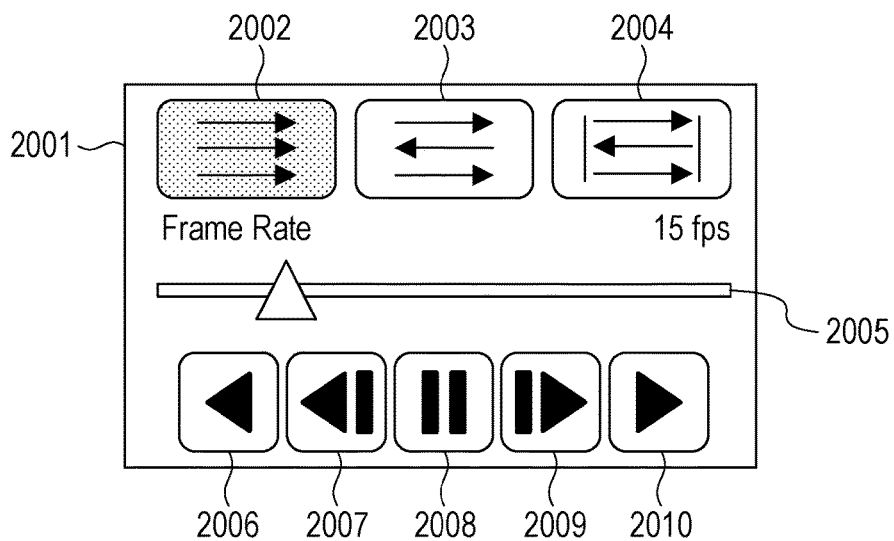

FIG. 22
(a)
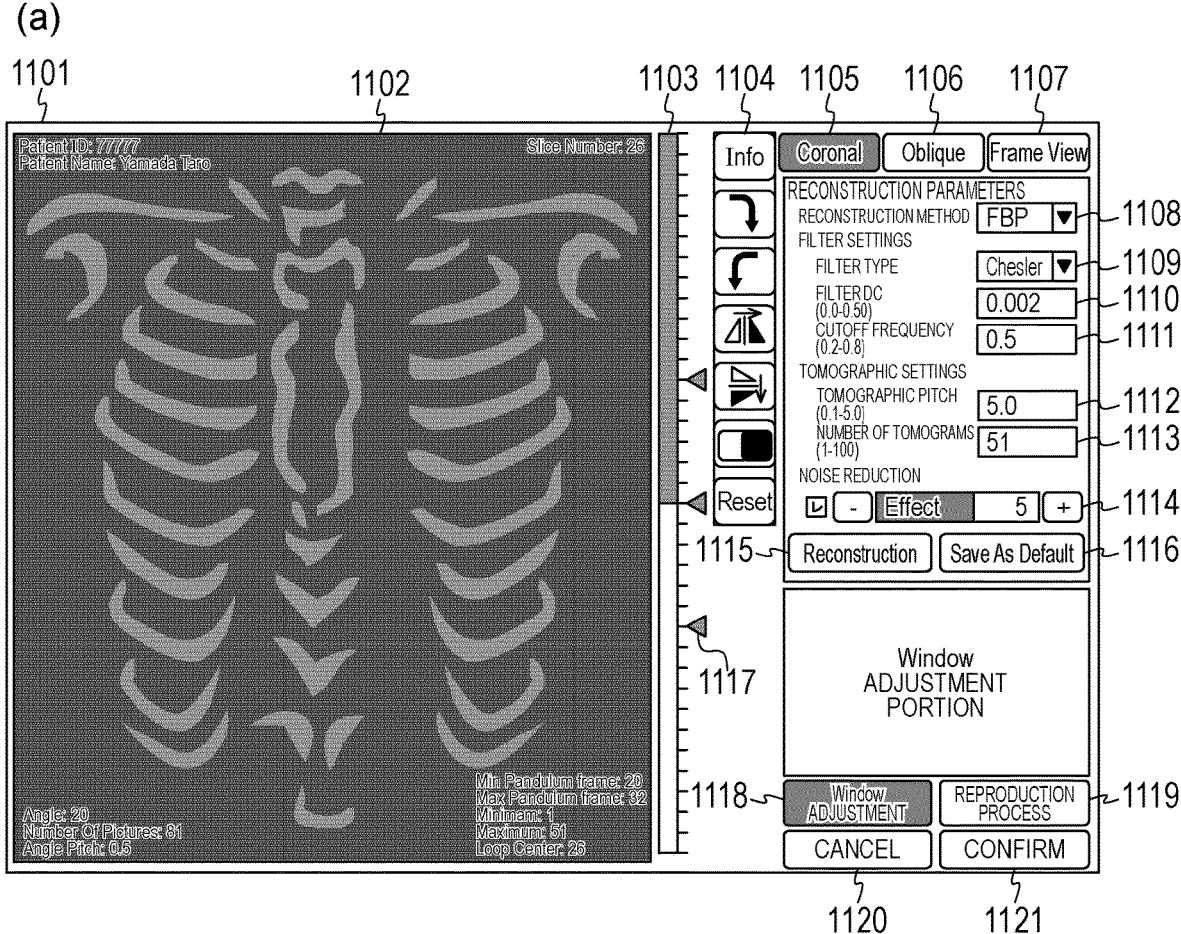
(b)
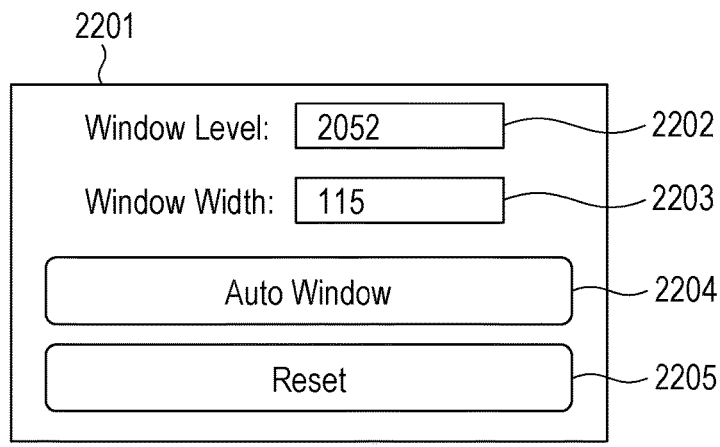

CONTROL DEVICE FOR CONTROLLING TOMOSYNTHESIS IMAGING, IMAGING APPARATUS, IMAGING SYSTEM, CONTROL METHOD, AND PROGRAM FOR CAUSING COMPUTER TO EXECUTE THE CONTROL METHOD

TECHNICAL FIELD

The present disclosure relates to a control device for controlling tomosynthesis imaging for capturing projected images of a plurality of frames and obtaining a tomosynthesis image from the plurality of projected images, an imaging apparatus, an imaging system, a control method, and a program for causing a computer to execute the control method.

BACKGROUND ART

In tomosynthesis imaging, an X-ray generation apparatus irradiates a person being examined with X-rays at different angles while being moved and an X-ray detector detects X-rays transmitted through the object, thereby allowing continuous capture of projected images of a plurality of frames having different imaging angles. The captured projected images of the plurality of frames are shifted so that the preset center positions thereof coincide with each other to make corresponding pixels overlap each other, thereby executing the reconstruction of a tomosynthesis image that is a tomographic image of a certain cross section of the person being examined (PTL 1). In addition, the reconstruction is re-performed with the reconstruction method, the filter settings, the slice pitch, and the number of slices changed, enabling a plurality of tomosynthesis images to be generated for projected images acquired in a single imaging session. The generated plurality of tomosynthesis images are subjected to window adjustment or geometric transformation processing, and are then used for diagnosis.

CITATION LIST

Patent Literature

PTL 1: Japanese Patent Laid-Open No. 2000-46760

SUMMARY OF INVENTION

Technical Problem

In a case where at least one tomosynthesis image is reconstructed on the imaging apparatus side, the tomosynthesis image is output to a PACS, an image viewer, a printer, or the like via a network after the end of an examination. In this case, it is conceivable that an image obtained as a result of imaging failure or a tomosynthesis image that does not need to be output is set as a reject, thereby switching ON/OFF of the output target. However, if a group of projected images on which a tomosynthesis image is based is set as rejects, the tomosynthesis image may also have a certain problem.

Solution to Problem

Accordingly, a control device for controlling tomosynthesis imaging according to an embodiment of the present invention is a control device for controlling tomosynthesis imaging for obtaining a tomosynthesis image from a projected image group captured by irradiating an object with X-rays from a plurality of different angles by using an X-ray generation unit and an X-ray detection unit. The control device includes a communication circuit that transmits at least either of data of a tomosynthesis image and data of the projected image group to an external device, setting means for setting at least one of the data of the tomosynthesis image or the data of the projected image group as a reject, and output control means for limiting transmission of the data set as a reject to the external device. In response to the data of the projected image group being set as a reject, the setting means sets data of a tomosynthesis image generated on the basis of the projected image group as a reject.

Advantageous Effects of Invention

This can facilitates a reject setting of a tomosynthesis imaging technique, and enables image output ON/OFF to be set.

BRIEF DESCRIPTION OF DRAWINGS

FIG. 8 is a diagram illustrating a patient information input screen according to the embodiment of the present invention.

FIG. 20 includes diagrams illustrating a screen showing a reproduction processing portion on the reconstruction screen according to the embodiment of the present invention.

FIG. 22 includes diagrams illustrating a screen showing a window adjustment portion on the reconstruction screen according to the embodiment of the present invention.

DESCRIPTION OF EMBODIMENTS

The configuration and operation of an X-ray imaging system according to an embodiment of the present invention will be described hereinafter with reference to FIGS. 1 to 29.

Figure 1:
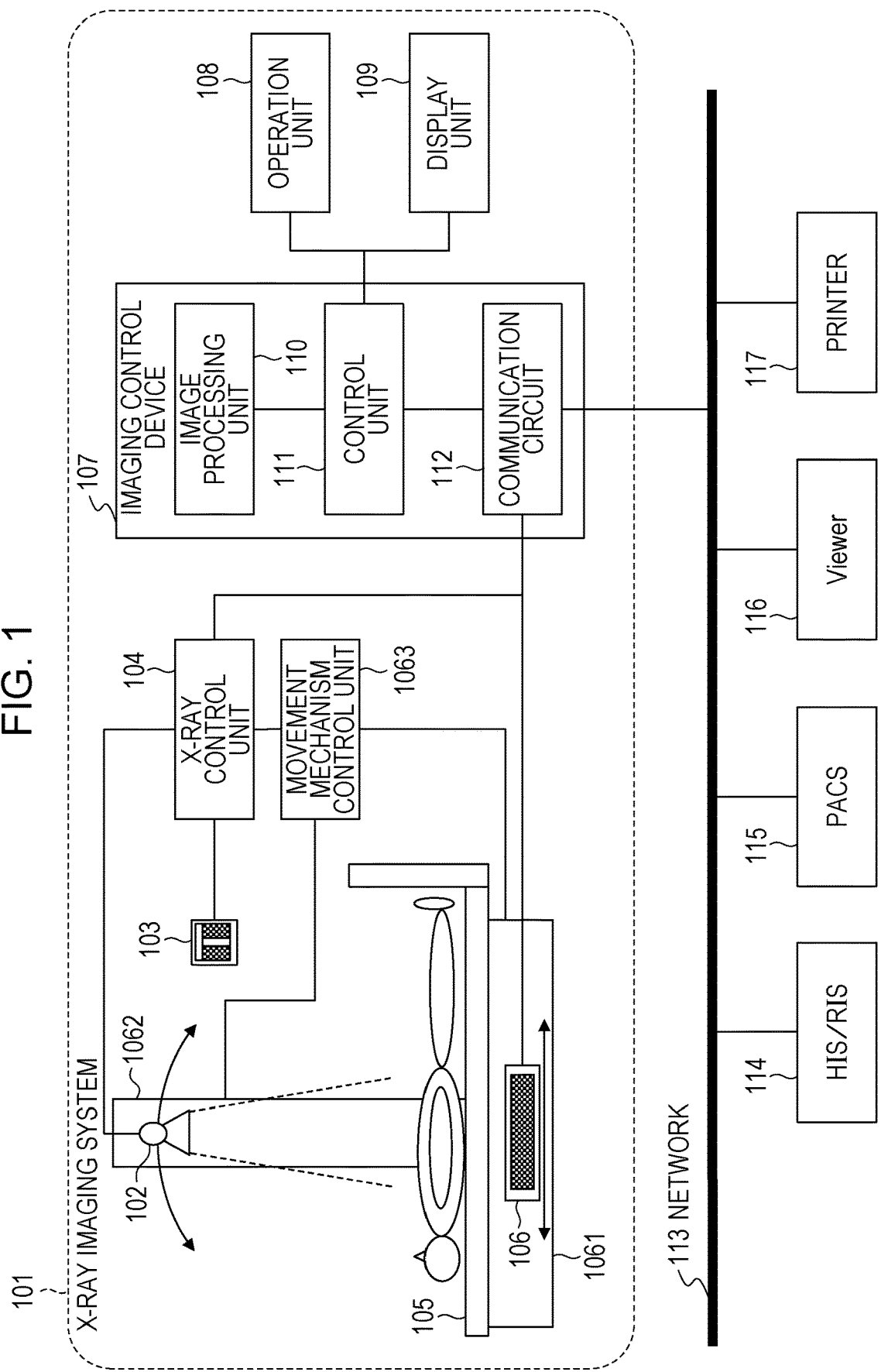
FIG. 1 is a configuration diagram of an X-ray imaging system according to an embodiment of the present invention.

FIG. 1 illustrates the configuration of an X-ray imaging system according to an embodiment of the present invention. An X-ray imaging system 101 includes an X-ray generation unit 102, a movement mechanism 1061, a column 1062, an X-ray irradiation switch 103, an X-ray control unit 104, an imaging table 105, an X-ray detector 106, an imaging control device 107, an operation unit 108, and a display unit 109. The X-ray detector 106 and the imaging control device 107 collectively serve as an X-ray imaging apparatus, in particular. The X-ray generation unit 102 and the X-ray control unit 104 collectively serve as an X-ray generation apparatus, in particular. The movement mechanism 1061, the column 1062, and a movement mechanism control unit 1063 collectively serve as an imaging system holding apparatus. The term imaging system, as used herein, is used to include the X-ray generation apparatus and the X-ray imaging apparatus, namely, the X-ray generation unit 102 and the X-ray detector 106. The X-ray generation apparatus and the imaging system holding unit may be collectively referred to as an X-ray generation apparatus.

The X-ray generation unit 102 performs X-ray irradiation. Further, the X-ray generation unit 102 transmits imaging execution conditions such as tube voltage and tube current and position information such as an imaging angle and an X-ray source moving distance to the X-ray control unit 104 in accordance with X-ray irradiation. Further, the X-ray generation unit 102 receives default imaging conditions and default position information from the X-ray control unit 104, and performs an imaging preparation process.

The movement mechanism 1061 is capable of linearly moving the X-ray detector 106 in the direction of the axis of the body of the object, for example. The column 1062 includes a movement mechanism that movably supports the X-ray generation unit 102, and is capable of moving the X-ray generation unit 102 along an arc in the direction of the axis of the body of the object.

The movement mechanism control unit 1063 controls the movement of the movement mechanism 1061 of the X-ray detector and the column 1062. The movement mechanism control unit 1063 is capable of moving the movement mechanism 1061 and the column 1062 in synchronization with each other. Here, the movement mechanism 1061 and the column 1062 are moved in synchronization with each other, the X-ray generation unit 102 is moved in a first direction, and the X-ray detector 106 is moved in a direction opposite to the first direction, thereby providing an execution of tomosynthesis imaging for obtaining projected images from a plurality of directions.

Further, the movement mechanism control unit 1063 is connected to the X-ray control unit 104. The movement mechanism control unit 1063 receives information on the timing of X-ray irradiation, and outputs position information on the X-ray generation unit 102 and the X-ray detector 106 at this timing to the X-ray control unit 104. For example, in the case of intermittent emission of pulsed X-rays, position information on the X-ray generation unit 102 and the X-ray detector 106 at the start of emission of the pulsed X-rays, at the end of the emission, or at a certain time during the emission is output.

The X-ray irradiation switch 103 transmits an irradiation start notification and an irradiation end notification to the X-ray control unit 104. When pressed by an operator, the X-ray irradiation switch 103 transmits an irradiation start notification. When released by the operator, the X-ray irradiation switch 103 transmits an irradiation end notification. When the X-ray irradiation switch 103 is being pressed, a sequence of projected images is captured while the X-ray generation unit 102 and the X-ray detector 106 are moved. During the capture of a sequence of projected images, for example, The X-ray generation unit 102 performs X-ray irradiation while being moved over a range from minus 30 degrees to plus 30 degrees. In this case, if the pressing of the X-ray irradiation switch 103 is stopped in the middle of the range at the time when an angle of plus 10 degrees is reached, the capture of projected images is interrupted. Note that a 0-degree position is established when the column 1062 extends in the vertical direction.

The X-ray control unit 104 is connected to the X-ray generation unit 102, the X-ray irradiation switch 103, and the imaging control device 107. The X-ray control unit 104 controls the start and end of X-ray irradiation, and transmits imaging execution conditions and position information. Further, the X-ray control unit 104 receives imaging conditions and position information from the imaging control device 107, and notifies the X-ray generation unit 102 of the imaging conditions and the position information.

The imaging table 105 is a support on which an object is placed. The movement mechanism 1061 of the X-ray detector, which moves the X-ray detector 106 in a direction along the top of the table, is provided immediately below the top.

The X-ray detector 106 includes an X-ray sensor having a plurality of photoelectric conversion elements arranged in a matrix. The X-ray detector 106 detects X-rays transmitted through the object, and converts the X-rays into X-ray image data. A discrete two-dimensional planar array of the plurality of photoelectric conversion elements defines an X-ray detection region and an X-ray detection surface. The X-ray detection surface extends in a direction along a surface of the X-ray detector 106, and is desirably substantially parallel to an upper surface. The X-ray detector 106 is arranged substantially in parallel to the top of the imaging table. In addition, the X-ray detector moves substantially in parallel to the top, and therefore the X-ray detector 106 moves along the X-ray detection surface. Here, "substantially" means that complete parallelism is not required for imaging and, for example, an error of about several degrees is tolerable.

The X-ray detector 106 is further connected to the imaging control device 107, and transmits the X-ray image data to the imaging control device 107 together with imaging execution information such as the scan area and the binning size and position information such as the X-ray detector moving distance. Further, the X-ray detector 106 receives default position information from the imaging control device 107, and performs an imaging preparation process. The transmission of the X-ray image data and the imaging execution and position information is performed by using wired communication via a cable connected to the imaging control device 107 or by using wireless communication. The imaging control device 107 may be configured to receive position information on the X-ray detector 106 from the X-ray control unit 104 via the movement mechanism control unit 1063.

The imaging control device 107 is a control device that totally controls the X-ray imaging system. The imaging control device 107 controls X-ray imaging with a combination of the X-ray control unit 104 and the X-ray detector 106, a reconstruction process using the X-ray image data, image processing such as tone conversion processing to be performed on the X-ray image data, an execution of an examination including X-ray imaging, input and output to and from the operation unit 108 and the display unit 109, transmission and reception to and from an external device via a network 113, and other operations. The imaging control device 107 is constituted by an image processing unit 110, a control unit 111, and a communication circuit 112.

The imaging control device 107 executes a method for controlling tomosynthesis imaging for obtaining a tomographic image from projected images obtained by irradiating an object with X-rays from a plurality of different angles by using an X-ray generation unit and an X-ray detection unit.

The imaging control device 107 is connected to the X-ray control unit 104 and the X-ray detector 106. The imaging control device 107 acquires projected images obtained through X-ray imaging and position information on the X-ray detector 106 and the X-ray generation unit 102 when the projected images are obtained, and reconstructs a tomosynthesis image. The image obtained by reconstruction is displayed on the display unit 109.

Additionally, the imaging control device 107 is connected to an HIS/RIS 114, a PACS 115, a viewer 116, and a printer 117 via the network 113. The HIS/RIS 114 is a hospital/radiology information management system for managing information in the radiology department, such as patient information and examination request information. The PACS 115 is an image management server whose main purpose is to save images. The viewer 116 is connected to the PACS 115, and a high-definition monitor is mainly used for visual inspection and detailed post-processing of an image obtained by imaging using the X-ray imaging system 101, and for diagnostic operations. The printer 117 prints and outputs the X-ray image data or tomosynthesis image data.

The image processing unit 110 performs image processing, such as tone conversion processing and noise reduction processing, on the received X-ray image data. Further, the image processing unit 110 performs a reconstruction process using the X-ray image data and the position information to reconstruct a tomosynthesis image. An image reconstructed from projected images obtained through tomosynthesis imaging is referred to as a tomosynthesis image in particular. A tomosynthesis image according to one embodiment is a representation of three-dimensional volume data based on a plurality of projected images.

The control unit 111 performs control for the execution of an examination and the execution of imaging, or saves/reads information on the execution of a suspended examination or a completed examination or X-ray image data. Further, the control unit 111 determines the situation in which interruption of imaging is occurring on the basis of the notified position information, and determines the availability of the execution of reconstruction and the availability of the display of an oblique cross section. Further, the control unit 111 calculates valid frames of a tomosynthesis image on the basis of the notified position information.

The communication circuit 112 transmits a variety of driving conditions such as an accumulation period of time, a binning condition, and a frame rate, in addition to an X-ray irradiation preparation request and an X-ray irradiation preparation cancellation request, to the X-ray control unit 104 and the X-ray detector 106 via a communication I/F. Further, the communication circuit 112 receives X-ray image data, imaging execution information, and position information from the X-ray control unit 104 and the X-ray detector 106. Further, the communication circuit 112 receives examination request information, transmits examination execution information, and outputs the X-ray image data or tomosynthesis image data via the network 113.

The operation unit 108 is an input interface that accepts an operation performed by an operator. The input interface of the operation unit 108 may be any interface having input capabilities, such as a keyboard, a mouse, or a multi-touch monitor. The operation unit 108 transmits input information to the imaging control device 107 in accordance with the operation. Further, the operation unit 108 receives a request from the imaging control device 107, and switches the display of the input interface.

The display unit 109 is an output interface on which a user interface of control software for X-ray imaging is displayed. The display unit 109 may be any interface having display capabilities, such as a separate monitor or a monitor incorporated in an X-ray imaging apparatus. A plurality of monitors on which captured images are displayed may be connected to a single imaging control device 107, and a captured image and a previous image may be displayed as previews on different monitors. In this case, the display unit 109 judges on which monitor and which image is displayed in accordance with a notification from the imaging control device 107.

The image processing unit 110 further generates a two-dimensional tomographic image from the volume data, if necessary. Examples of the generated two-dimensional tomographic image include a tomographic image (first two-dimensional tomographic image) in the direction along the detection surface. Referring to the configuration of the imaging system illustrated in FIG. 1, this tomographic image corresponds to a coronal image of the object. A two-dimensional tomographic image in the direction along the detection surface (referred to as a first two-dimensional tomographic image) is often used since an obtained tomographic image can at least have sufficient image quality, which depends on the limitations on the irradiation angle in tomosynthesis imaging.

In addition, the image processing unit 110 is also capable of generating a two-dimensional tomographic image intersecting the detection surface (second two-dimensional tomographic image). For example, the image processing unit 110 is capable of generating a so-called oblique image that is a tomographic image having a certain inclination to the direction of the axis of the body of the object, that is, the movement direction of the X-ray generation unit 102 and the X-ray detector 106. Needless to say, it is possible to generate any other two-dimensional tomographic image intersecting the detection surface. For example, referring to the imaging system illustrated in FIG. 1, sagittal images or axial images can be generated. In the case of tomosynthesis imaging in which the X-ray generation unit 102 and the X-ray detector 106 are moved along the axis of the body of the object, it can be conceived in terms of image quality that an oblique image is generated whereas no sagittal image or axial image is generated. In the case of tomosynthesis imaging in which the X-ray generation unit 102 and the X-ray detector 106 are two-dimensionally moved along the top of the imaging table 105, a sagittal image or an axial image may be generated.

In another embodiment, a set of two-dimensional tomographic images along, more desirably, parallel to, the detection surface of the X-ray detector 106 may be directly reconstructed from a sequence of projected images, and may be handled as a tomosynthesis image. In this case, a process for directly reconstructing, for example, each of oblique, sagittal, and axial images from projected images is executed.

The communication circuit 112 transmits driving conditions for the X-ray detector 106 to the X-ray detector 106, and receives from the X-ray detector 106 a sequence of projected images to be used for the reconstruction process based on projected images described above. Accordingly, the imaging control device 107 can obtain projected images to be used for a reconstruction process.

In addition, the communication circuit 112 receives from the X-ray control unit 104 position information on the X-ray generation unit 102 and the X-ray detector 106 at the timings when the respective projected images are captured. In this regard, the communication circuit 112 functions as a unit for acquiring projected images and position information. Based on the sequence of projected images and the position information, the image processing unit 110 performs a reconstruction process. The position information includes, for example, information on the direction in which the X-ray generation unit 102 performs X-ray irradiation to the X-ray detector 106.

Here, the desired tomographic image may not be obtained due to the interruption of the imaging or the limitations on the movement mechanism 1061 or the movement mechanism of the column 1062 or depending on conditions such as the imaging interval for projected images or the setting of the irradiation angle or the range of the irradiation direction of the X-ray generation unit 102.

Accordingly, the control unit 111 performs display control to impose a limitation on a second two-dimensional tomographic image to be displayed, by using the information on the irradiation direction of the X-ray generation unit 102 within the position information obtained from the communication circuit 112. For example, projected images have been obtained in the irradiation direction from −30 degrees to +10 degrees. In this case, a limitation is imposed such that an oblique image having an intersection angle up to ±10 degrees to the detection surface of the X-ray detector 106 or the top of the imaging table 105 is displayed, whereas an oblique image having an intersection angle larger than +10 degrees or an intersection angle smaller than −10 degrees is not displayed. It is a matter of course that an oblique image having an intersection angle up to ±5 degrees may be a target to be displayed. Further, an oblique image may be displayed with an intersection angle in the range from −30° to +10°. In another example, projected images have been obtained with irradiation angles in the range from −20 degrees to +20 degrees. In this case, a limitation is imposed such that an oblique image having an intersection angle up to ±20 degrees to the detection surface of the X-ray detector 106 or the top of the imaging table 105 is displayed, whereas an oblique image having an intersection angle larger than +20 degrees or an intersection angle smaller than −20 degrees is not displayed.

In the way described above, a process for specifying the range of the display target on the basis of the range of the irradiation direction, causing a second two-dimensional tomographic image within the specified range of the display target, and removing a second two-dimensional tomographic image outside the range from the display target is executed. This enables a two-dimensional tomographic image of a guaranteed sufficient quality to be displayed, and can reduce the probability of false diagnosis.

In another example, in the case of irradiation over a range from −30 degrees to 30 degrees, the display of oblique images is prohibited if only projected images up to −5 degrees have been obtained. In still another example, in the case of similar irradiation conditions, the display of oblique images is also uniformly prohibited if only projected images over a range from −30 degrees to 10 degrees are successfully obtained due to circumstances such as interruption of the imaging. In the manner described above, if it is determined that projected images satisfying the desired irradiation conditions are not successfully obtained, a uniform limitation on the display of oblique images can ensure higher image quality.

In still another example, if the irradiation interval for projected images is 0.5 degrees, oblique images are also controlled not to be displayed at intervals less than 0.5 degrees, and, if the irradiation interval is 0.1 degrees, oblique images are also controlled not to be displayed at intervals less than 0.1 degrees. In the manner described above, a limitation on the display interval of oblique images by using information on X-ray irradiation directions for the respective projected images can ensure the quality of the oblique images to be displayed.

In addition, such generation and display of coronal images or oblique images are performed within a modality, in particular, by the imaging control device 107 that controls tomosynthesis imaging. Accordingly, whether or not tomosynthesis imaging is appropriate can be checked before transmission to the PACS 115 and the like, enabling an improvement in the efficiency of medical diagnosis.

Figure 2:
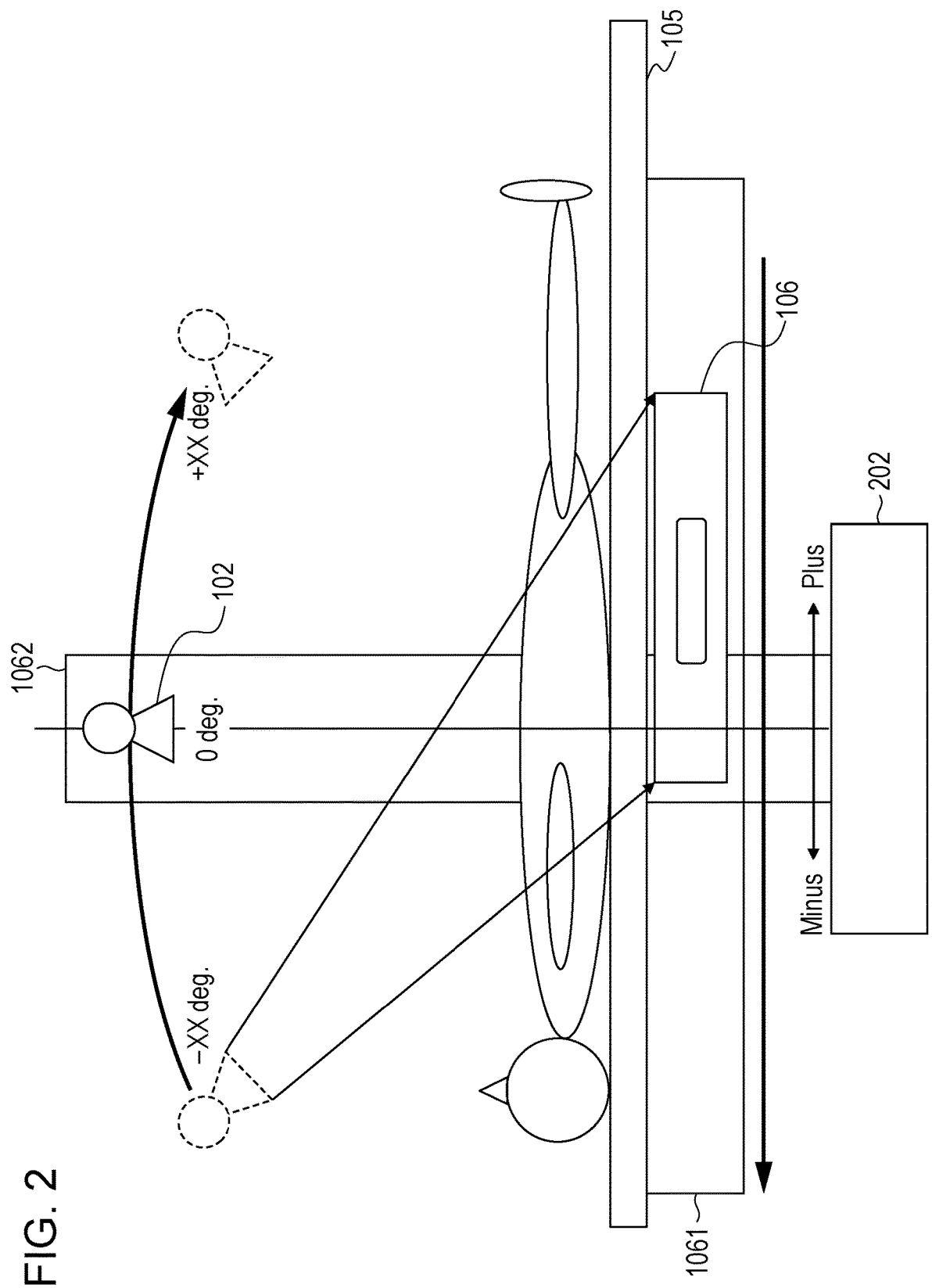
FIG. 2 is a system configuration diagram of tomosynthesis imaging according to the embodiment of the present invention.

Here, a system configuration related to tomosynthesis imaging is illustrated using FIG. 2. The X-ray generation unit 102 is fixed to the column 1062 which is inclinable. During the collection of projected image data, the X-ray generation unit 102 and the X-ray detector 106 move in horizontally opposite directions, with respect to, as a center, a position at which the imaging table 105 and the column 1062 are perpendicular to each other before the start of irradiation, by a preset distance in a direction (horizontal direction) along the imaging table 105 and the detection surface. In this case, the irradiation range of the X-ray generation unit 102 is set so as to be included in the detection region of the X-ray detector 106. Along with the start of irradiation, the X-ray generation unit 102 and the X-ray detector 106 collect projected image data on which the reconstruction process is based and acquires position information while moving toward the center. The tomosynthesis image described above is generated based on the projected image data obtained by imaging in the way described above.

The imaging control device 107 or the X-ray control unit 104 sets the range of the irradiation direction or the irradiation interval of the X-ray generation unit 102. In this embodiment, the column 1062 is configured to allow the X-ray generation unit 102 to move on an arc, where the position at which the column 1062 is vertical is defined as a 0-degree position and a θ direction is plotted in the left-to-right direction in FIG. 2. In addition to this, setting information indicating plus minus θ degrees is input to the movement mechanism control unit 1063 from the imaging control device 107 or the X-ray control unit 104, and the column 1062 causes the X-ray generation unit 102 to move so that the initial position before the imaging is minus θ degrees. When the X-ray generation unit 102 is at a position of θ° with respect to the upright direction of the column 1062 (the vertical direction), θ° is referred to as an irradiation angle. Furthermore, a direction connecting the focal point of the X-ray generation unit 102 and the center position of the X-ray detector 106 at this time is referred to as an X-ray irradiation direction. The angle defined by the X-ray irradiation direction with respect to the vertical direction is θ° in the condition where an isocenter for tomosynthesis imaging is fixed. Thus, in the following exemplary embodiment, the irradiation angle and the irradiation direction are used with similar meanings.

In FIG. 2, the X-ray generation unit 102 moves from left to right. In accordance with this setting information, the movement mechanism 1061 allows the X-ray detector 106 to move. The range of the irradiation direction is not limited to the definition described above, and, for example, a position of −90 degrees in the example described above may be used as a reference. As an alternative, the range of the irradiation direction of the X-ray generation unit 102 may be set using a parameter other than the angle. For example, as in FIG. 2, the distance over which the center position of the column 1062 or the X-ray generation unit 102 is displaced from the state where the column 1062 is upright may be used as setting information. Setting information is converted into the movement mechanism 1061 or the column 1062 or a control value by the X-ray control unit 104 or the movement mechanism control unit 1063, and is output to a driving mechanism for these components, such as a motor, so that the driving mechanism allows the X-ray generation unit 102 and the X-ray detector 106 to move.

The imaging interval is a parameter indicating an interval at which projected images are captured, and has a value defined by the interval of the irradiation angle, for example. Alternatively, the imaging interval can be defined by a displacement of the X-ray generation unit 102 in the horizontal direction with respect to the position at which the column 1062 is upright. The imaging interval is not necessarily an equal interval, and is decided on as necessary. For example, in the case of imaging with an irradiation angle of ±30 degrees, the imaging interval is decided on by setting the number of imaging sessions. In the case of tomosynthesis imaging in the step-and-shoot mode, the movement mechanism control unit 1063 causes the movement mechanism 1061 and the column 1062 to move by a control amount corresponding to the interval of the irradiation angle, and the X-ray control unit 104 instructs the X-ray generation unit 102 to emit X-rays at the timing when the movements are stopped. After the X-ray irradiation is completed, the movement mechanism control unit 1063 again causes the movement mechanism 1061 and the column 1062 to move by a control amount defined by the parameter of the imaging interval. In the case of tomosynthesis imaging in the continuous mode, X-rays are emitted during the movement. The movement mechanism control unit 1063 continuously monitors the positions, and the X-ray control unit 104 starts X-ray irradiation at the timing when an X-ray irradiation position (imaging position) defined by the imaging interval is reached.

Figure 3:
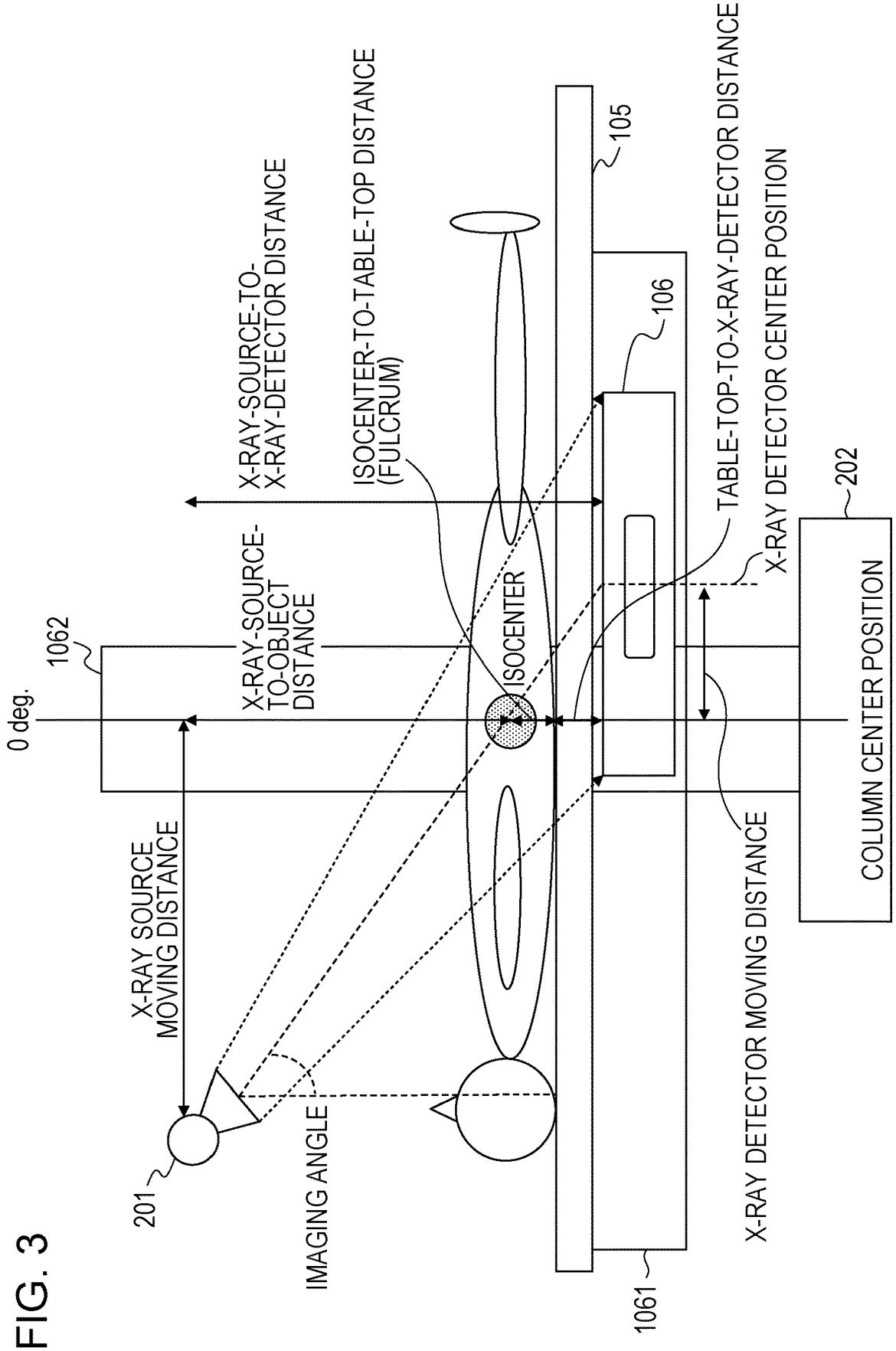
FIG. 3 is a diagram illustrating position information acquired during tomosynthesis imaging.

FIG. 3 illustrates the details of the position information obtained during the collection of projected image data. As a method for moving the X-ray generation unit 102, either a method in which the column 1062 horizontally moves or a method in which the column 1062 is inclined in its portion in contact with a foundation 202 may be used.

Here, the details of the position information are illustrated using FIG. 3. Here, the angle at which the imaging table 105, the X-ray detector 106, and the column 1062 to which an X-ray source 201 is fixed are perpendicular is defined as 0°. (I do not have a good explanation for this; the absolute value of the angle increases like ±1, 2, . . . as inclination increases in opposite directions from) 0°. Further, a position at which the X-ray detector 106, the X-ray source 201, and the position of the isocenter are aligned in series with a position perpendicular to the imaging table 105 is defined as a center position at which the moving distance is 0. (The absolute value of the moving distance increases like ±1, 2, . . . in accordance with movements in opposite directions from the center position). The isocenter is in a tomographic position at which the clearest image is generated among a plurality of frames of a tomosynthesis image created by reconstruction. The respective moving distances of the X-ray source 201, the X-ray detector 106, and the imaging table 105 on which the object is placed are controlled so that the isocenter is always located on a straight line connecting the focal point position of the X-ray source 201 and the detection region center position of the X-ray detector 106 during the capture of projected images. The isocenter-to-table-top distance (hereinafter, referred to the fulcrum) is the distance from the isocenter at the center position to the topmost of the imaging table 105. A specific value is used for each imaging session. The fulcrum is set as one of the default imaging conditions included in imaging technique information. In addition, a temporary change to the settings or a change to the default settings can be made by input to the operation unit 108 during the execution of an examination. The X-ray control unit 104 controls the operation of the X-ray generation unit 102 by referring to the fulcrum received from the imaging control device 107. Thereafter, at the completion of irradiation for projected images, the X-ray control unit 104 receives the input of fulcrum as a piece of position information, and transmits the fulcrum to the imaging control device 107. The fulcrum is used for the reconstruction process based on the FBP (Filtered Back Projection) algorithm and the shift-and-add algorithm. The fulcrum is also used for the calculation of the X-ray-source-to-object distance. The imaging angle is the inclination of the X-ray source 201 when the center position is 0°. A maximum imaging angle is set as one of the default imaging conditions included in imaging technique information. In addition, a temporary change to the settings or a change to the default settings can be made by input to the operation unit 108 during the execution of an examination. In a single imaging session, the inclination is successively changed from the maximum imaging angle in the negative direction to the maximum imaging angle in the positive direction through the center position. The positive and negative directions in which the inclination is changed may be reversed. As the imaging angle, an imaging angle obtained when image data is read is acquired for each of a plurality of consecutive X-ray image frames of projected images. At the completion of irradiation for projected images, the X-ray control unit 104 receives the input of the imaging angle as a piece of position information, and transmits the imaging angle to the imaging control device 107. An imaging angle pitch that is changed for each read of image data is decided on by dividing the amount by which the angle is changed in a single imaging session by the number of frames scheduled to be captured. The imaging angle is used for the reconstruction process based on the FBP (Filtered Back Projection) algorithm and the shift-and-add algorithm. The imaging angle is also used for the determination of an imaging state by an imaging interruption determination unit 401. In addition, the imaging angle is further used for limiting the designation of the angle during the display of a reconstruction oblique cross section. The X-ray source moving distance is a distance through which the X-ray source 201 moves in a direction parallel to the imaging table 105 with respect to the center position. The X-ray source 201 moves to the right or left from the center position in synchronization with the X-ray detector 106, and is inclined at an angle that allows the isocenter to be located on a straight line connecting the focal point position of the X-ray source 201 and the detection region center position of the X-ray detector 106 to meet the imaging angle corresponding to the setting. Accordingly, the X-ray source moving distance is decided on in synchronization with the setting of the imaging angle. As the X-ray source moving distance, an X-ray source moving distance obtained when image data is read is acquired for each of a plurality of consecutive X-ray image frames of projected images. At the completion of irradiation for projected images, the X-ray control unit 104 receives the input of an X-ray source moving distance for each X-ray image frame as a piece of position information, and transmits the X-ray source moving distance to the imaging control device 107. The X-ray source moving distance is used for the reconstruction process based on the FBP (Filtered Back Projection) algorithm and the shift-and-add algorithm. The X-ray detector moving distance is a distance through which the X-ray detector 106 moves in a direction parallel to the imaging table 105 with respect to the center position. The X-ray detector 106 moves to the right or left from the center position in a direction opposite to that of the X-ray source 201 in synchronization with the X-ray source 201, and moves so that the isocenter is located on a straight line connecting the focal point position of the X-ray source 201 and the detection region center position of the X-ray detector 106 to meet the imaging angle corresponding to the setting. Accordingly, similarly to the X-ray source moving distance, the X-ray detector moving distance is also decided on in synchronization with the setting of the imaging angle. As the X-ray detector moving distance, an X-ray detector moving distance obtained when image data is read is acquired for each of a plurality of consecutive X-ray image frames of projected images. At the completion of irradiation for projected images, the X-ray control unit 104 receives the input of an X-ray detector moving distance for each X-ray image frame as a piece of position information, and transmits the X-ray detector moving distance to the imaging control device 107. The X-ray detector moving distance is used for the reconstruction process based on the FBP (Filtered Back Projection) algorithm and the shift-and-add algorithm. An X-ray-source-to-X-ray-detector distance is a distance from the X-ray source 201 at the center position to the topmost of the X-ray detector 106. The X-ray-source-to-X-ray-detector distance has a specific value for each imaging apparatus. The X-ray-source-to-X-ray-detector distance is used for the calculation of the X-ray-source-to-object distance. A table-top-to-X-ray-detector distance is a distance from the topmost of the imaging table 105 at the center position to the topmost of the X-ray detector 106. The table-top-to-X-ray-detector distance has a specific value for each imaging apparatus. The table-top-to-X-ray-detector distance is used for the calculation of an X-ray-source-to-object distance. The X-ray-source-to-object distance is a distance from the X-ray source 201 at the center position to the object with respect to the isocenter. The X-ray-source-to-object distance has a specific value for each imaging session depending on the fulcrum set for each imaging session. More specifically, the X-ray-source-to-object distance is calculated by an imaging control unit 405 in accordance with the equation below using the X-ray-source-to-X-ray-detector distance, fulcrum, and table-top-to-X-ray-detector distance included in the position information received by the imaging control device 107 at the completion of irradiation for projected images.

*X*-ray-source-object distance=*X*-ray-source-to-*X*-ray-detector distance−(fulcrum+table-top-to-*X*-ray-detector distance)

The X-ray-source-object distance is used for the reconstruction process based on algorithms such as the FBP (Filtered Back Projection) algorithm and the shift-and-add algorithm.

The parameters described above are used as position information on the X-ray generation unit 102 and the X-ray detector 106. Among the pieces of position information, the isocenter position, the table-top-to-X-ray-detector distance, and the fulcrum have common values for the imaging system or in a single imaging session, whereas the other pieces of position information are different for the capture of each projected image. Accordingly, a set of pieces of position information common for a single imaging session and position information different for each projected image is output from the X-ray control unit 104 to the imaging control device 107 via the movement mechanism control unit 1063.

Figure 4:
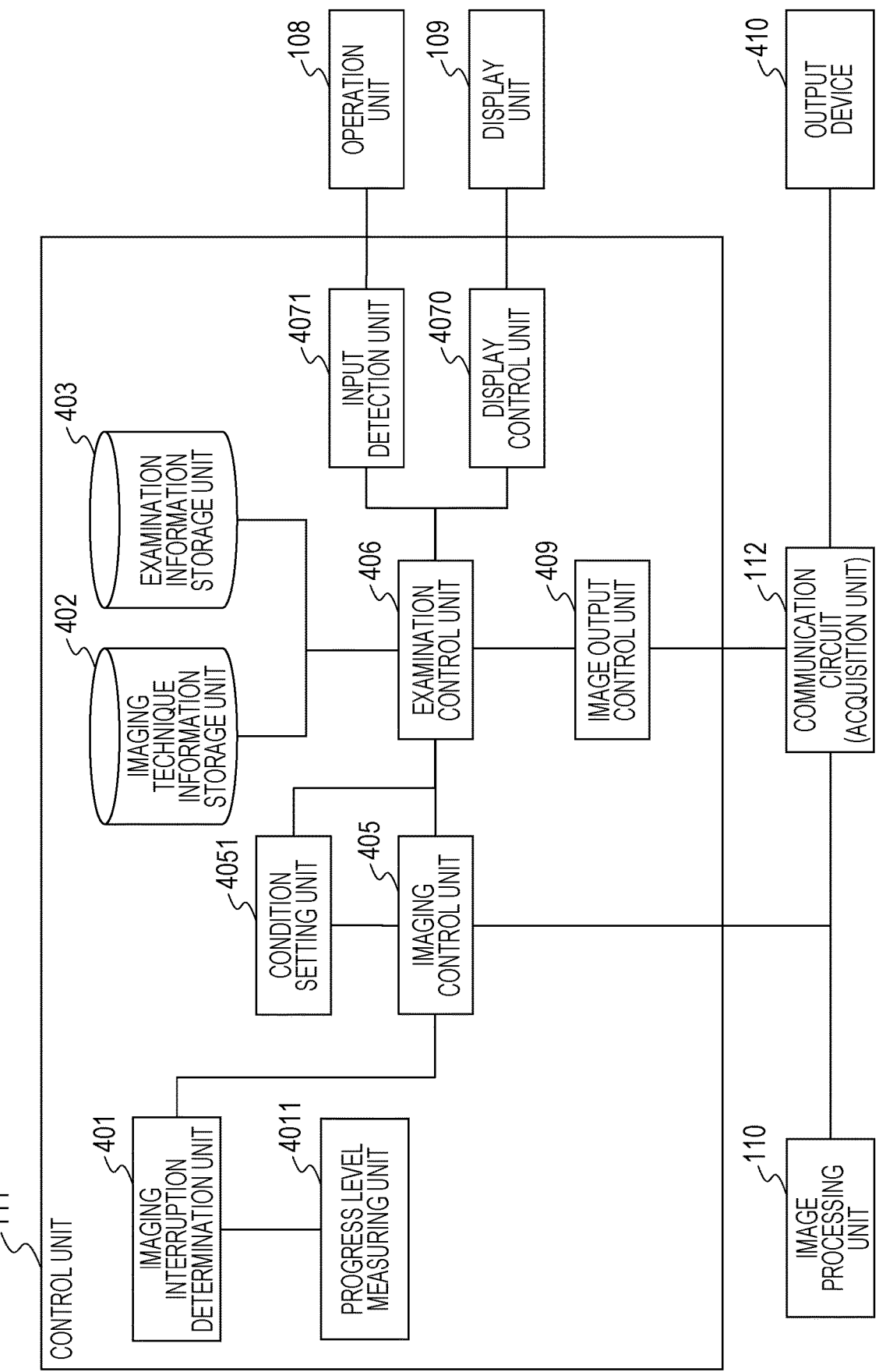
FIG. 4 is a configuration diagram of an imaging control unit according to the embodiment of the present invention.

FIG. 4 illustrates a detailed configuration of the control unit 111 related to the X-ray imaging system 101 in the present invention. The control unit 111 includes the imaging interruption determination unit 401, an imaging technique information storage unit 402, an examination information storage unit 403, an imaging control unit 405, a condition setting unit 4051, an examination control unit 406, a display control unit 4070, an input detection unit 4071, an image output control unit 409, and a progress level measuring unit 4011.

The imaging technique information storage unit 402 saves, updates, deletes, and searches for imaging technique information. The imaging technique information illustrated here includes items that can be set for each imaging technique and that cover from the execution of imaging to post-processing and image output settings, such as information for identifying an imaging technique such as the part to be imaged and the imaging direction, imaging conditions, image processing parameters, reconstruction parameters, storage transfer settings, and printing settings. The imaging technique information storage unit 402 is constituted by a database. The examination information storage unit 403 registers, updates, deletes, and searches for examination information of examination information. The examination information storage unit 403 is constituted by a database.

The imaging control unit 405 transmits and receives data of imaging availability, imaging execution conditions, and position information to and from the X-ray generation unit 102 and the X-ray detector 106 via the communication circuit 112. Further, the imaging control unit 405 performs control of the overall flow of a single X-ray imaging session and the overall flow of the execution of a reconstruction process, such as control for the execution of a reconstruction process and the storage of X-ray image data.

The condition setting unit 4051 sets an imaging condition in accordance with, for example, an operation input from the operation unit 108. The condition setting unit 4051 is a setting unit that extracts imaging conditions from the imaging technique information obtained from the imaging technique information storage unit 402 and that transmits the imaging conditions as imaging parameters to the respective units such as the imaging control unit 405, the image processing unit 110, the X-ray detector 106, the X-ray generation unit 102, and the movement mechanism control unit 1063. The term imaging parameters, as used herein, is used to include, for example, the number of projected images captured, the imaging interval for projected images, information on a range of X-ray irradiation positions ($\pm\theta$), the number of coronal image first secondary tomographic images (coronal images) created, the creation pitch, other image processing parameters, and drive parameters for the X-ray detector 106.

The examination control unit 406 performs control of the overall flow of the execution of an examination, such as control of the update/registration of patient information, examination-scheduled-to-be-conducted information, and imaging technique information, control of screen transitions, storage of tomosynthesis image data, and a process for adding a tomosynthesis image. The term examination refers to a concept that encompasses a plurality of units of imaging, and common information is processed for a transition between imaging sessions and a plurality of imaging sessions included in one unit of examination.

The input detection unit 407 accepts and interprets an operation input from the operation unit 108. The display control unit 4070 performs the overall display control of the display unit 109 in response to output instructions notified by the examination control unit 406, such as a screen transition. For example, the display control unit 4070 performs display control of a projected image or a tomosynthesis image, a process for changing the display of a GUI (Graphical User Interface) in accordance with the operation input to the operation unit 108, and so forth.

The image output control unit 409 determines image output availability of an image included in the received examination information, and instructs the communication circuit 112 to output the image to an output device 410. The output device 410 corresponds to, for example, the PACS 115, the viewer 116, or the printer 117.

The imaging interruption determination unit 401 determines whether or not the imaging has been interrupted, by using the position information notified from the X-ray control unit 104. If the imaging is interrupted, position information not corresponding to a predetermined range of irradiation positions is obtained or the number of projected images is insufficient to meet a specified amount. Accordingly, the imaging interruption determination unit receives, as input, information on a preset number of projected images captured, information on the range of irradiation positions, position information obtained as a result of imaging, information on projected images, and other information, and determines whether or not the tomosynthesis imaging has been interrupted.

An example of the interruption determination method is as follows. In a case where the number of projected images captured has been set by the condition setting unit 4051, if the number of projected images obtained through the communication circuit 112 is less than that value, the imaging interruption determination unit 401 determines that the imaging has been interrupted. If both numbers match, the imaging interruption determination unit 401 determines that the imaging has been completed.

In another example, it is determined that the imaging has been interrupted if the number of elements of position information included in the set of pieces of position information obtained from the X-ray control unit 104 is smaller than a predetermined number of captured images, and it is determined that the imaging has been completed if the number of elements is equal to the number of captured images. If the number of elements of position information is larger than the number of captured images, it can be determined that an error has occurred. Alternatively, if at least one of the number of pieces of position information and the number of projected images is smaller than a prescribed number of captured images, it is determined that the imaging has been interrupted. If both numbers match the number of captured images, it is determined that the imaging has been completed without interruption. Such an example is also provided.

In another example, in a case where the range of irradiation positions is set to $\pm\theta$, it is determined that the imaging has been interrupted if the position information obtained through the communication circuit 112 ranges from $-\theta\theta$ to $+\theta'$ ($<\theta$), and it is determined that the imaging has been completed if data in the range from $-\theta$ to $+\theta$ has been obtained. In this case, the actually set range does not necessarily exactly match a range of position information acquired in actuality. Thus, for example, any digits in the difference after the decimal place are ignored and it is determined that an interruption has occurred.

Alternatively, the X-ray control unit 104 may be configured to output notifications of the start, interruption, and completion of imaging, and the output may be received by the communication circuit 112 and interpreted by the interruption determination unit 401 to determine that an interruption has occurred.

Alternatively, there is also considered a case where the pieces of position information described above are not used directly for determination. For example, during imaging, the communication circuit 112 regularly receives the progress of capturing projected images from the X-ray control device 104. If the X-ray control device 104 notifies the imaging control device 107 of the completion of the imaging before the progress reaches 100%, it is determined that an interruption has occurred. If there is a notification indicating that the progress has reached 100%, it is determined that the imaging has been completed without interruption. The progress is obtained in the X-ray control device 104 by, for example, dividing the number of times irradiation has been provided by a specified number of times of irradiation. Instead of the progress, the value of the number of times imaging has been performed (the number of times of irradiation) can be directly handled as information indicating the degree of progress.

Alternatively, such a degree of progress can be obtained within the control unit 111. In such an embodiment, the control unit 111 includes the progress level measuring unit 4011. The progress level measuring unit 4011 measures a level of progress of imaging by using setting information, such as the number of projected images captured and the information on the range of irradiation positions, and execution information, such as the number of projected images that have been captured and the set of pieces of position information. After the completion of the imaging, the progress level measuring unit 4011 identifies a degree of progress indicating a degree to which the capture of projected images has been completed, or a level of progress of imaging, by using information such as the set of pieces of position information.

The display control unit 4070 limits the display of oblique images or second two-dimensional tomographic images by using the information on the degree of progress of the imaging. For example, the display of oblique images is limited in accordance with the degree of progress in such a manner that, if it is determined that the imaging has been interrupted when the degree of progress is 60%, oblique images having intersection angles up to 5 degrees to the detection surface are displayed, and oblique images having intersection angles up to 15 degrees are displayed if an interruption has occurred when the degree of progress is 80%. The relationship between the degree of progress and the degree of limitation of display can be experimentally determined.

In addition, for example, the display control unit 4070 imposes a limitation so that no two-dimensional tomographic image (second two-dimensional tomographic image) intersecting the detection surface is displayed if the imaging interruption determination unit 401 determines that an interruption has occurred and if the degree of progress is greater than or equal to 50% and less than 100%. On the other hand, since the degree of progress is greater than or equal to 50%, the embodiment in FIG. 2 described above allows projected image data obtained by irradiation from the respective positions in the range of at least −θ° to 0° to have been obtained. Thus, a two-dimensional tomographic image (coronal image) along the detection surface is displayed because the quality can be guaranteed. This threshold value may be set as desired by the display control unit 4070 or may be experimentally determined in accordance with the progress and information on irradiation positions. If the degree of progress is less than 50%, the display of both a first tomographic image and a second tomographic image is limited. In this case, the imaging control unit 405 additionally performs control to prohibit the reconstruction process for a tomosynthesis image, which is performed by the image processing unit 110, to lessen the processing load. In this case, furthermore, the image output control unit 409 handles imaging data of the relevant projected image group as reject data, and limits the output of such data to the output device 410, which can prevent unwanted image data from being output.

Figure 5:
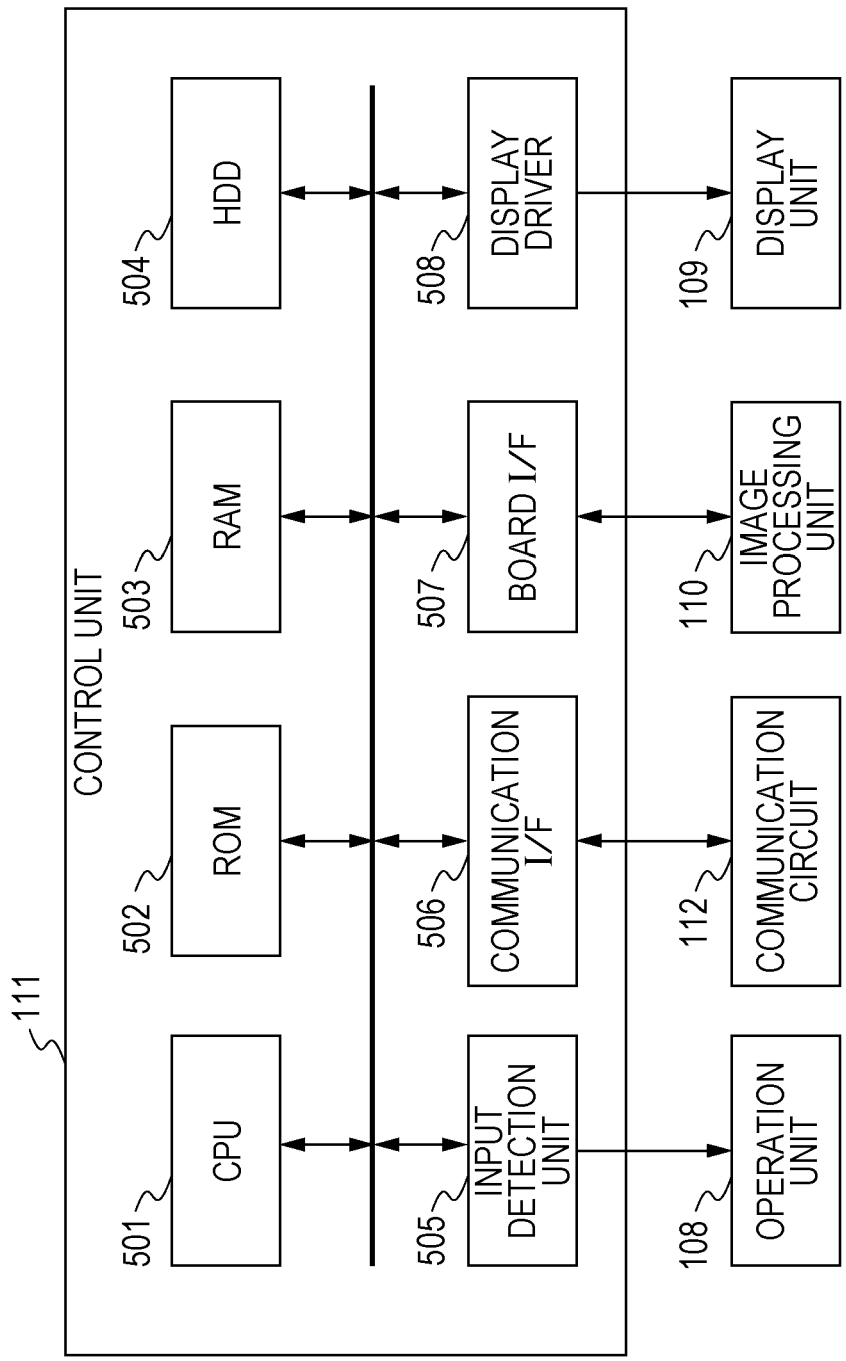
FIG. 5 is a hardware configuration diagram of the imaging control unit according to the embodiment of the present invention.

The hardware example configuration of the imaging control device according to the embodiment will be described with reference to FIG. 5. The control unit 111 includes a CPU 501, a ROM 502, a RAM 503, an HDD 504, an input detection unit 505, a communication I/F 506, a graphics board 507, and a display driver 508. These components are connected to one another via a bus such as a data bus. The CPU 501 is configured to perform the overall control of the control unit 111, and executes an instruction program stored in the ROM 502 to execute control. The program is executed by the CPU 501 to cause the control unit 111 to exert the functions of the imaging interruption determination unit 401, the progress level measuring unit 4011, the imaging technique information storage unit 402, the examination information storage unit 403, the imaging control unit 405, the condition setting unit 4051, the examination control unit 406, the display control unit 4070, the input detection unit 4071, and the image output control unit 409. Further, the program is a program for executing processes illustrated in FIG. 6, FIG. 7, and FIG. 13 described below.

Further, the CPU 501 performs input/output control for the display unit 109 via the display driver 508, and input/output control for the operation unit 108 via the input detection unit 505. The RAM 503 is configured to reserve a working storage area when the CPU performs control in accordance with an instruction program. The HDD 504 is an auxiliary storage device that saves various kinds of data such as X-ray image data. The communication I/F 506 is a communication interface constituting the communication circuit 112, and transmits and receives data between the control unit 111 and each of the X-ray control unit 104, the X-ray detector 106, and the network 113. The graphics board 507 is configured to constitute the image processing unit 110, and performs image processing and a reconstruction process using a GPU.

Subsequently, an example of the flow from the start to the end of a typical tomosynthesis imaging examination in the present invention is illustrated using FIG. 6.

In step S601, patient information is created prior to the start of the examination. The patient information illustrated here includes all the pieces of information for identifying a patient, such as the patient's name, patient ID, age, date of birth, gender, height, weight, and pregnancy state.

In step S601, the display unit 109 displays a patient information input screen 801. When an instruction for confirming the patient information is given, the operation unit 108 transmits a patient information confirmation notification including the patient information to the input detection unit 4071. Upon receipt of the patient information confirmation notification, the input detection unit 4071 transmits the patient information confirmation notification to the examination control unit 406. Upon receipt of the patient information confirmation notification, the examination control unit 406 newly generates examination-scheduled-to-be-conducted information. The examination-scheduled-to-be-conducted information illustrated here includes the patient information described above, examination information including all the items for identifying an examination, such as examination ID and examination date and time, and imaging technique information including all the pieces of information for identifying an imaging technique, such as the part to be imaged. Then, the examination control unit 406 inputs the patient information included in the patient information confirmation notification to the examination-scheduled-to-be-conducted information. Thereafter, the examination control unit 406 transmits a notification of a request to obtain all the registered imaging technique information to the imaging technique information storage unit 402. Upon receipt of the notification of the request to obtain all the imaging technique information, the imaging technique information storage unit 402 acquires all the registered imaging technique information, and transmits the acquired imaging technique information to the examination control unit 406. Upon receipt of the imaging technique information, the examination control unit 406 transmits an imaging technique selection screen transition notification together with the imaging technique information to the display control unit 4070. Upon receipt of the imaging technique selection screen transition notification, the display control unit 4070 transmits the imaging technique selection screen transition notification to the display unit 109 for display. Upon receipt of the imaging technique selection screen transition notification, the display unit 109 displays an imaging technique selection screen 901. The display unit 109 displays all the pieces of received imaging technique information on the imaging technique selection screen 901.

Then, in step S602, examination information is created. The creation of examination information illustrated here includes the selection of a scheduled imaging technique. When an instruction for starting the examination is given, the operation unit 108 transmits an examination information confirmation notification including the examination information and the selected scheduled imaging technique to the input detection unit 4071. Upon receipt of the examination information confirmation notification, the input detection unit 4071 transmits the examination information confirmation notification to the examination control unit 406. Upon receipt of the examination information confirmation notification, the examination control unit 406 inputs the examination information and the scheduled imaging technique, which are included in the examination information confirmation notification, to the examination execution information generated at the time when the patient information is confirmed.

The flow of manually creating patient information, examination information, and a scheduled imaging technique is illustrated in steps S601 to S602, but is not limited thereto. Selecting work list information acquired from the HIS/RIS 114 enables patient information, examination information, and a scheduled imaging technique to be created at once. In this case, step S601 is omitted. When an instruction for starting the examination is given, the operation unit 108 transmits an examination information confirmation notification including patient information, examination information, and a scheduled imaging technique, which are included in the selected work list information, to the input detection unit 4071. The subsequent flow is similar to that described above.

Then, in step S603, an examination start process is carried out. When the creation of examination execution information is completed in step S602, the examination control unit 406 transmits an examination start notification to the examination information storage unit 403 and the display control unit 4070. The examination start notification includes examination-scheduled-to-be-conducted information. Upon receipt of the examination start notification, the examination information storage unit 403 registers the examination-scheduled-to-be-conducted information as new examination information. Then, the examination information storage unit 403 updates the examination status of the registered new examination information to in progress". The examination status includes not started", in progress", in suspension", and "end". Upon receipt of the examination start notification, the display control unit 4070 transmits an imaging screen transition notification to the display unit 109. The imaging screen transition notification includes the examination-scheduled-to-be-conducted information. Upon receipt of the imaging screen transition notification, the display unit 109 displays an imaging screen 1001. The display unit 109 displays, on the imaging screen 1001, the patient information, the examination information, and the imaging technique information included in the received examination information.

In step S604, an imaging technique with which imaging is executed next is selected from among the scheduled imaging techniques included in the started examination information. The selection of an imaging technique is selected by pressing an imaging technique display portion 1009 displayed on the imaging screen 1001. Upon acceptance of the pressing of an imaging technique button, the operation unit 108 transmits an imaging technique selection notification to the input detection unit 4071. The imaging technique selection notification includes selected imaging technique information. Upon receipt of the imaging technique selection notification, the input detection unit 4071 transmits an imaging technique selection notification to the examination control unit 406. The display control unit 4070 transmits an under-preparation-for-irradiation display notification to the display unit 109. Upon receipt of the under-preparation-for-irradiation display notification, the display unit 109 switches the display of a sensor status display portion 903 on the imaging screen 1001. Upon receipt of the imaging technique selection notification, the examination control unit 406 transmits an irradiation permission request notification to the imaging control unit 405. The irradiation permission request notification includes the selected imaging technique information. Upon receipt of the irradiation permission request notification, the imaging control unit 405 transmits the irradiation permission request notification to the communication circuit 112. Upon receipt of the irradiation permission request notification, the communication circuit 112 transmits the irradiation permission request notification to the X-ray control unit 104 and the X-ray detector 106. Upon receipt of the irradiation permission request notification, the X-ray control unit 104 notifies the X-ray generation unit 102 of the imaging conditions and position information included in the imaging technique information included in the irradiation permission request notification. Thereafter, when the setting of conditions for the X-ray generation unit 102 and the movement of the X-ray generation unit 102 to the initial position are completed, the X-ray control unit 104 transmits an irradiation permission notification to the communication circuit 112. The irradiation permission notification includes imaging technique information for which irradiation has been permitted. Upon receipt of the irradiation permission request notification, the X-ray detector 106 moves to the default position in accordance with the default position information included in the imaging technique information included in the irradiation permission request notification. When X-ray detection is ready for use, the X-ray detector 106 transmits an irradiation permission notification to the communication circuit 112. Upon receipt of the irradiation permission notifications from both the X-ray control unit 104 and the X-ray detector 106, the communication circuit 112 transmits an irradiation permission notification to the imaging control unit 405. Upon receipt of the irradiation permission notification, the imaging control unit 405 transmits the irradiation permission notification to the examination control unit 406. Upon receipt of the irradiation permission notification, the examination control unit 406 transmits the irradiation permission notification to the display control unit 4070. Upon receipt of the irradiation permission notification, the display control unit 4070 transmits an irradiation permission display notification to the display unit 109. Upon receipt of the irradiation permission display notification, the display unit 109 switches the display of the sensor status display portion 903 on the imaging screen 1001. Further, the display unit 109 displays an intended-for-imaging thumbnail 1012 in the imaging technique display portion 1009 on the imaging screen 1001. In the way described above, switching the display of the sensor status display portion 903 and the imaging technique display portion 1009 allows the viewer to easily identify that irradiation is available and distinguish the imaging technique for which an image is to be added in the next irradiation. While the flow of manual selection of an imaging technique has been described, the present invention also enables automatic selection of an imaging technique at the timing when the next imaging session is ready to start, such as at the start of an examination or at the end of irradiation. In this case, at the time when the next imaging session is ready to start, the examination control unit 406 acquires imaging technique information whose status is "imaging not yet started" from among the scheduled imaging technique information included in the examination-scheduled-to-be-conducted information. The status of the imaging technique information includes "imaging in progress" and "imaging completed" as well as "imaging not yet started". The examination control unit 406 selects the first registered imaging technique in the imaging technique information indicating "imaging not yet started", and transmits an irradiation permission request. The method for selecting one imaging technique is not limited thereto. This can save the time taken for an operator to manually select the next imaging technique each time imaging is performed, and achieve smooth work flow.

In step S605, the object is placed. The placement of the object is performed by an operator or a person in charge of the examination. Step S605 may be performed before or after steps S601 to S604.

In step S606, a center position for reconstruction is set. Mainly the operator or the person in charge of the examination measures the center position (hereinafter, the isocenter position) on the basis of the region of interest of the object, and the isocenter position is input through the operation unit 108. When the input of the isocenter position is confirmed, the operation unit 108 transmits a center position confirmation notification to the input detection unit 4071. The center position confirmation notification includes isocenter position information. Upon receipt of the center position confirmation notification, the input detection unit 4071 transmits the center position confirmation notification to the examination control unit 406. Upon receipt of the center position confirmation notification, the examination control unit 406 transmits the center position confirmation notification to the imaging control unit 405. Upon receipt of the center position confirmation notification, the imaging control unit 405 inputs the isocenter position information to the position information included in the currently selected imaging technique information.

In step S607, positioning of the object with fluoroscopy is performed. In particular, since the influence of artifacts on tomosynthesis largely depends on the direction of X-rays with which the examinee is irradiated, fluoroscopy is used to check the placement of the patient to check whether the object has been placed in the correct position. When the X-ray irradiation switch 103 is pressed, the X-ray irradiation switch 103 transmits an irradiation start request to the X-ray control unit 104. Upon receipt of the irradiation start request, the X-ray control unit 104 transmits an irradiation start instruction to the X-ray generation unit 102. Upon acceptance of the irradiation start instruction, the X-ray generation unit 102 starts X-ray irradiation. Thereafter, the X-ray generation unit 102 transmits an irradiation start notification to the X-ray control unit 104. Upon receipt of the irradiation start notification, the X-ray control unit 104 transmits the irradiation start notification to the imaging control unit 405 via the communication circuit 112. Upon receipt of the irradiation start notification, the imaging control unit 405 transmits the irradiation start notification to which the currently selected imaging technique information is added to the examination control unit 406. Upon receipt of the irradiation start notification, the examination control unit 406 updates the status of the imaging technique for which irradiation has been started within the imaging technique information included in the examination-scheduled-to-be-conducted information to "imaging in progress". Further, the examination control unit 406 transmits the irradiation start notification to the display control unit 4070. Upon receipt of the irradiation start notification, the display control unit 4070 transmits an irradiation-in-progress display notification to the display unit 109. Upon receipt of the irradiation-in-progress display notification, the display unit 109 switches the display of the sensor status display portion 903 on the imaging screen 1001. Meanwhile, the X-ray detector 106 detects the emitted X-rays, and converts the X-rays into X-ray image data. Further, the X-ray detector 106 acquires position information in synchronization with the detection of the X-rays. The X-ray detector 106 transmits the X-ray image data and the position information to the imaging control unit 405 via the communication circuit 112. Upon receipt of the X-ray image data and the position information, the imaging control unit 405 inputs the position information to the currently selected imaging technique. Further, the imaging control unit 405 transmits the X-ray image data to the examination control unit 406. Upon receipt of the X-ray image data, the examination control unit 406 transmits the X-ray image data to the display control unit 4070. Upon receipt of the X-ray image data, the display control unit 4070 transmits the X-ray image data to the display unit 109. Upon receipt of the X-ray image data, the display unit 109 displays the X-ray image data in live view in an image display portion 1002 on the imaging screen 1001. Thereafter, when the X-ray irradiation switch 103 is released, the X-ray irradiation switch 103 transmits an irradiation stop request to the X-ray control unit 104. Upon receipt of the irradiation stop request, the X-ray control unit 104 transmits an irradiation stop instruction to the X-ray generation unit 102. Upon acceptance of the irradiation stop instruction, the X-ray generation unit 102 stops X-ray irradiation. Thereafter, the X-ray generation unit 102 transmits an irradiation end notification and an imaging execution condition notification to the X-ray control unit 104. The imaging execution condition notification includes imaging execution conditions and position information. Upon receipt of the irradiation end notification and the imaging execution condition notification, the X-ray control unit 104 transmits the irradiation end notification and the imaging execution condition notification to the imaging control unit 405 via the communication circuit 112. Upon receipt of the irradiation end notification and the imaging execution condition notification, the imaging control unit 405 transmits the irradiation end notification to which the currently selected imaging technique information is added and the imaging execution condition notification to the examination control unit 406. Upon receipt of the irradiation end notification, the examination control unit 406 updates the status of the imaging technique for which irradiation has been completed within the imaging technique information included in the examination-scheduled-to-be-conducted information to "imaging completed". Further, upon receipt of the irradiation implementation condition notification, the examination control unit 406 inputs the irradiation implementation conditions to the imaging technique for which irradiation has been completed within the imaging technique information included in the examination-scheduled-to-be-conducted information. At the same time, the examination control unit 406 transmits the irradiation end notification and the imaging execution condition notification to the display control unit 4070. Upon receipt of the irradiation end notification and the imaging execution condition notification, the display control unit 4070 transmits an irradiation end display notification and the imaging execution condition notification to the display unit 109. Upon receipt of the irradiation end display notification, the display unit 109 switches the display of the sensor status display portion 903 on the imaging screen 1001. Further, upon receipt of and the imaging execution condition notification, the display unit 109 updates the corresponding display annotation in an image display portion 902. While the case where the X-ray generation unit 102 simultaneously transmits an irradiation end notification and an imaging execution condition notification has been described, the present invention is not limited thereto. A notification of imaging execution conditions may be sent in real time during irradiation, or imaging execution conditions may be transmitted after the end of irradiation at a different timing from the transmission of an irradiation end notification. Alternatively, imaging execution conditions and position information may be transmitted at different timings.

Tomosynthesis imaging may not involve positioning with fluoroscopy. In this case, step S607 is omitted.

Figure 13:
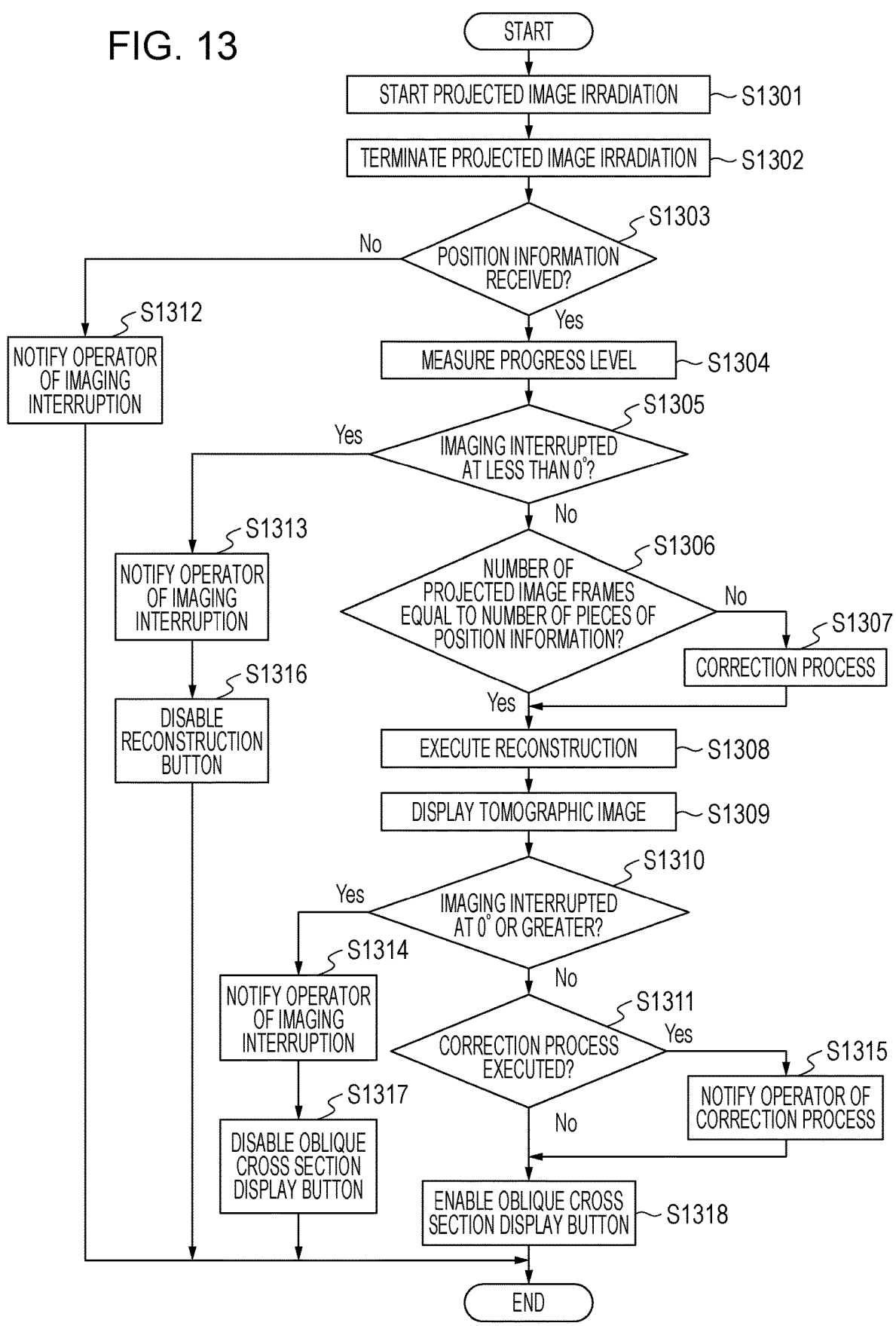
FIG. 13 is a flowchart diagram illustrating a process flow according to the embodiment of the present invention from the start of irradiation for projected images to the display of a reconstruction screen.
Figure 14:
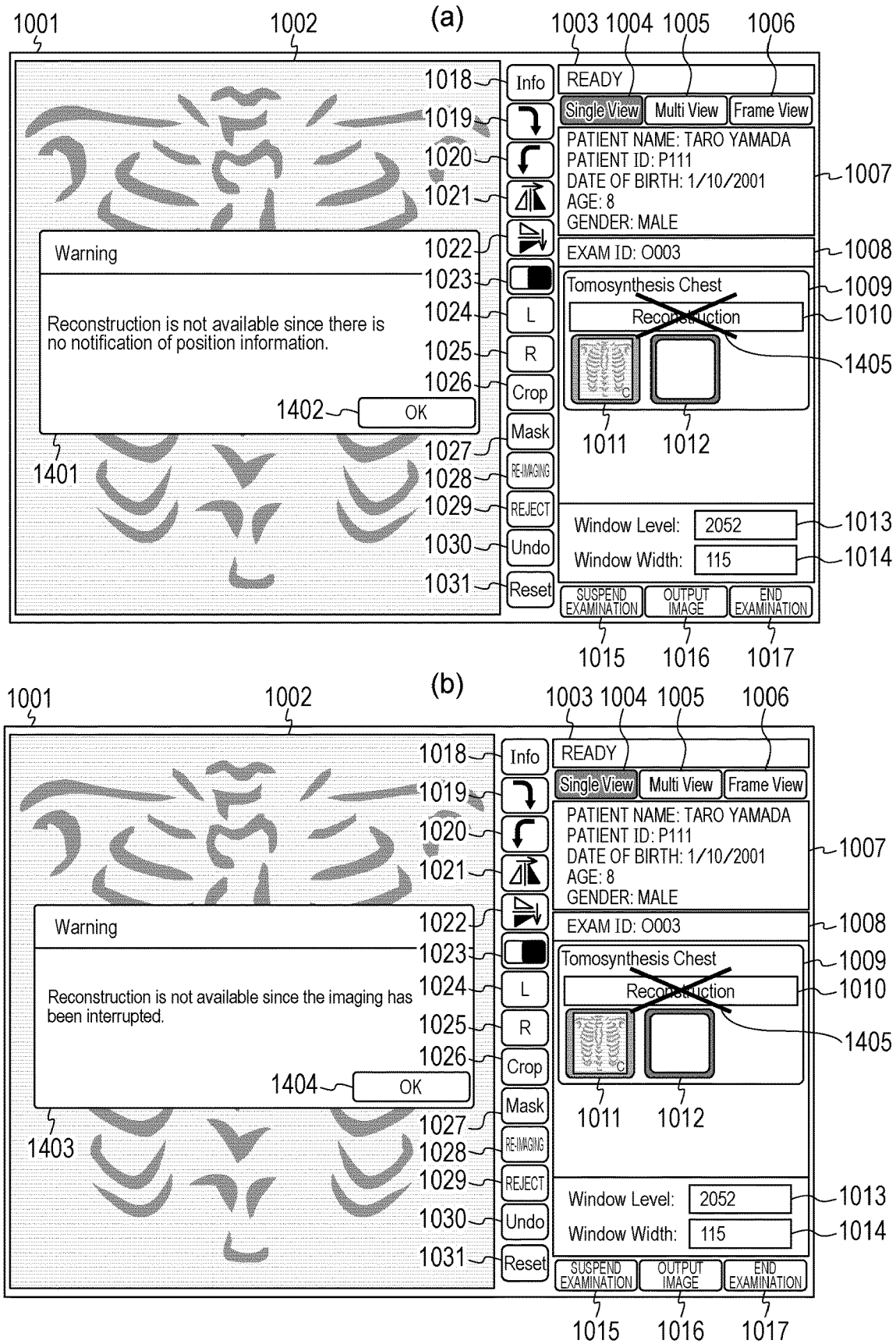
FIG. 14(a) is a diagram illustrating the imaging screen according to the embodiment of the present invention in a case where there is no notification of position information.
FIG. 14(b) is a diagram illustrating the imaging screen according to the embodiment of the present invention in a case where imaging is interrupted at less than 0°.

In step S608, projected images are captured. The process flow for the capture of projected images is almost similar to that with fluoroscopy in step S607. Note that, in the capture of projected images, upon receipt of the X-ray image data and the position information, the imaging control unit 405 inputs the position information to the currently selected imaging technique and saves the X-ray image data. In the present invention, furthermore, upon receipt of an irradiation end notification for projected images, the imaging control unit 405 determines the situation in which interruption of imaging is occurring from the position information. The imaging control unit 405 decides on whether a reconstruction process is available or not or whether the display of an oblique cross section is available or not in accordance with the situation in which interruption of imaging is occurring obtained as a result of the determination, and notifies the examination control unit 406 of the result (FIG. 13). This can prevent wasteful execution of reconstruction and prevent the display of an ineffective tomosynthesis image if the capture of projected images has been interrupted. This can also avoid the risk of false diagnosis by the reference to an oblique cross section with missing information.

In step S609, a reconstruction process is performed. Upon receipt of the X-ray image data of projected images and position information, the imaging control unit 405 transmits a reconstruction start notification to the display control unit 4070. At the same time, the imaging control unit 405 transmits a reconstruction request notification to the image processing unit 110. The reconstruction request notification includes the imaging technique information, the X-ray image data, and the position information. In this case, in the present invention, the imaging control unit 405 compares the number of frames of the X-ray image data of the projected images with the number of elements of position information. If both numbers are equal, the imaging control unit 405 transmits the reconstruction request notification as is. If there is a discrepancy between the numbers, the imaging control unit 405 performs a correction process to make the numbers match, and then transmits the reconstruction request notification (FIG. 13). This can also avoid the risk of failure of the reconstruction process if a discrepancy occurs between the number of frames of the X-ray image data and the number of elements of position information due to factors such as incorrect control of the X-ray generation unit 102 or the X-ray detector 106. Upon receipt of the reconstruction start notification, the display control unit 4070 transmits reconstruction screen display to the display unit 109. Upon receipt of the reconstruction screen notification, the display unit 109 displays a reconstruction screen 1101, and displays a progress bar on the image display portion 1002. Meanwhile, upon receipt of the reconstruction request notification, the image processing unit 110 performs a reconstruction process by using default reconstruction parameters in the imaging technique information, the position information, and the X-ray image data. When the reconstruction process is completed, the image processing unit 110 transmits a reconstruction completion notification to the imaging control unit 405. The reconstruction completion notification includes the generated tomosynthesis image, reconstruction parameters, and image processing parameters. Upon receipt of the reconstruction completion notification, the imaging control unit 405 transmits the reconstruction completion notification to the examination control unit 406.

Upon receipt of a reconstruction confirmation notification, the examination control unit 406 transmits a reconstruction end notification to the display control unit 4070. The reconstruction end notification includes imaging technique information in which the saved tomosynthesis image is present. Upon receipt of the reconstruction end notification, the display control unit 4070 transmits an imaging screen display notification to the display unit 109. Upon receipt of the imaging screen display notification, the display unit 109 shows a transition to the imaging screen 1001. At the same time, the display unit 109 adds a captured image thumbnail 1011 of the saved tomosynthesis image, and displays the captured image thumbnail 1011 as a preview.

In step S610, post-processing for tomosynthesis images is performed. The post-processing for tomosynthesis images includes the editing of cropped regions, parallel display (multi-view) of tomosynthesis images, a re-imaging process, and a reject process. When all the scheduled imaging techniques have been completed and the post-processing for tomosynthesis images has been completed, an examination end instruction is given. When an examination end instruction is given, the operation unit 108 transmits an examination end request notification to the input detection unit 4071. Upon receipt of the examination end request notification, the input detection unit 4071 transmits the examination end request notification to the examination control unit 406.

Then, in step S611, an examination termination process is carried out. The examination control unit 406 transmits an examination end notification to the examination information storage unit 403 and the display control unit 4070. The examination end notification includes examination-scheduled-to-be-conducted information. At the same time, the examination control unit 406 transmits an image output notification to the image output control unit 409. The image output notification includes examination-scheduled-to-be-conducted information. Upon receipt of the examination end notification, the examination information storage unit 403 searches for and acquires examination-scheduled-to-be-conducted information from the registered examination information. Then, the examination information storage unit 403 updates the examination status in the acquired examination information to "end". Upon receipt of the examination end notification, the display control unit 4070 transmits the examination end notification to the display unit 109. Upon receipt of the examination end notification, the display unit 109 shows a transition to the patient information input screen 801. Also when the operation unit 108 accepts a suspension of the examination, a flow similar to that for the termination of the examination is used. Note that the examination information storage unit 403 updates the examination status in the acquired examination information to "in suspension". Then, in step S612, image output is carried out. Upon receipt of the image output notification, the image output control unit 409 performs an image output process for the output device 410 via the communication circuit 112.

Figure 6:
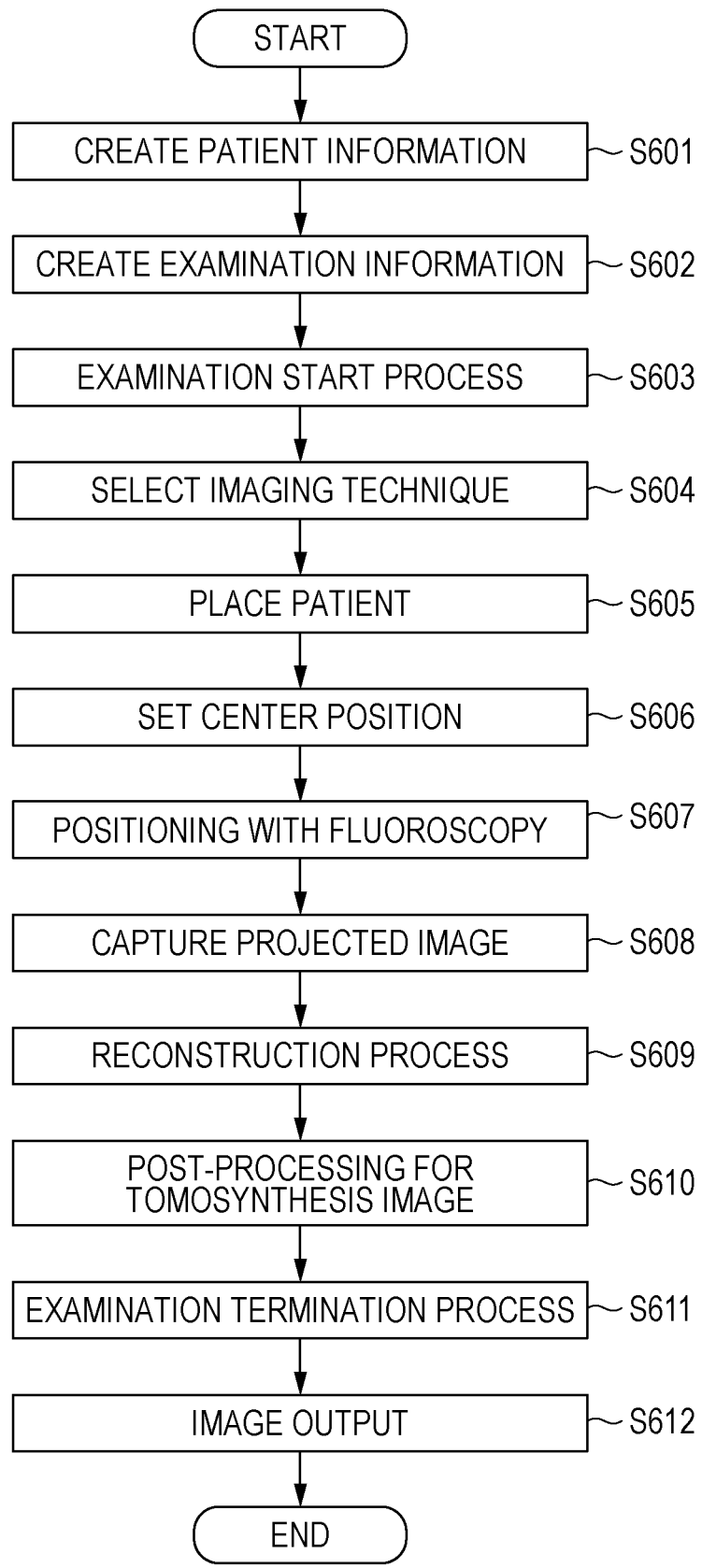
FIG. 6 is a flowchart diagram illustrating a process flow according to the embodiment of the present invention from the start to the end of an examination during tomosynthesis imaging.
Figure 7:
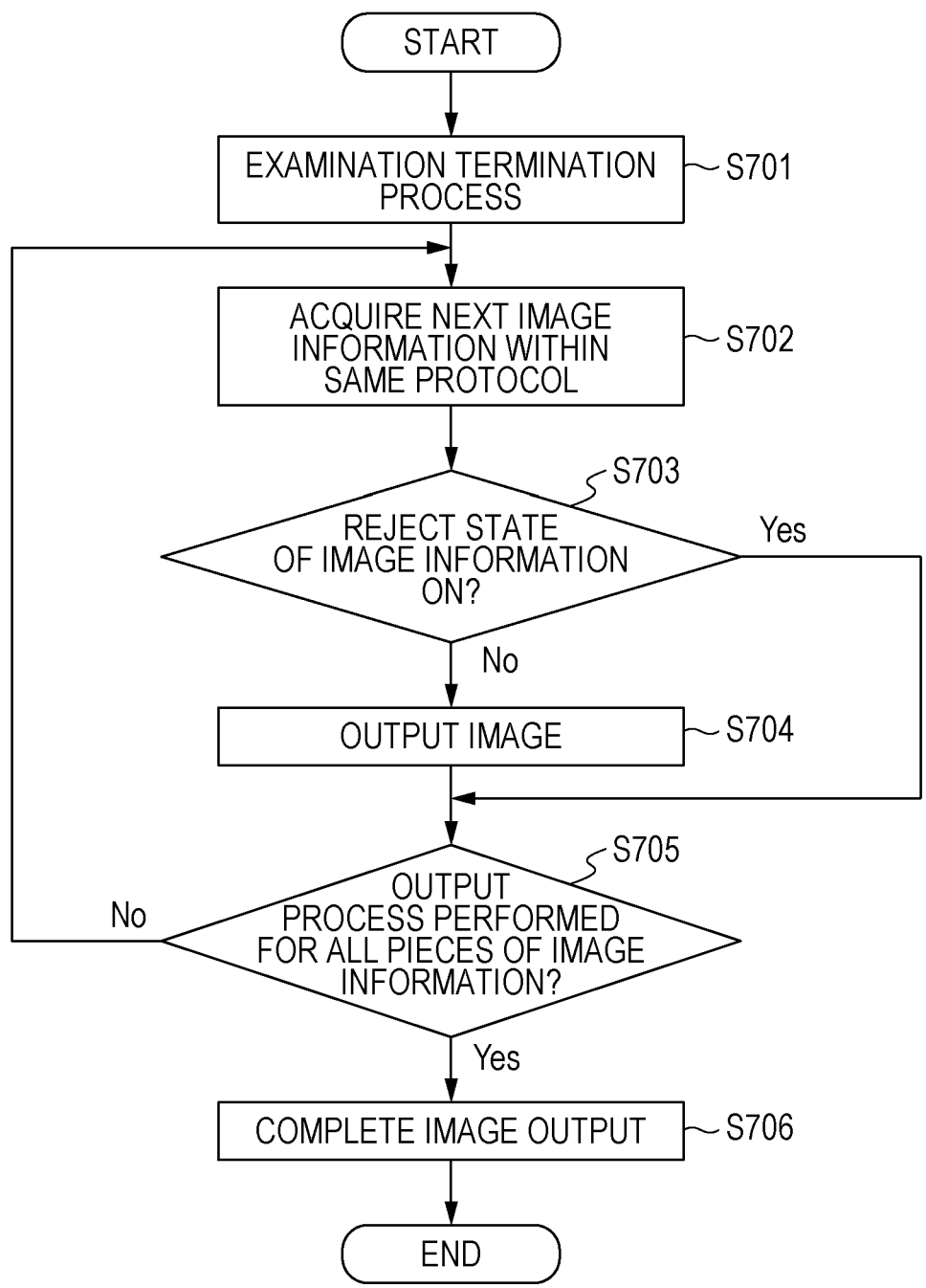
FIG. 7 is a flowchart diagram illustrating a process flow according to the embodiment of the present invention from the end of the examination to the completion of image output.

Here, the flow of an image output process in the present invention will be illustrated using FIG. 7. First, in step S701, an examination termination process is carried out. The examination termination process is similar to that in step S611 in FIG. 6. Then, in step S702, the image output control unit 409 acquires all the imaging techniques whose status is "imaging completed" from the examination-scheduled-to-be-conducted information included in the image output notification, and acquires the image information at the beginning. Then, in step S703, the image output control unit 409 checks the reject state of the acquired image information. If the reject state is OFF, the image output control unit 409 proceeds to step S704. In step S704, the image output control unit 409 transmits an image output request notification to the communication circuit 112. The image output request notification includes X-ray image data or tomosynthesis image data, and image information. At the same time, the image output control unit 409 sets the output state of the image information to ON. Upon receipt of the image output request notification, the communication circuit 112 outputs the image data or tomosynthesis image data included in the image output request notification to the output device 410. Then, in step S705, the image output control unit 409 checks whether or not an output process has been performed on all the pieces of image information acquired in step S702. If the output state of the image information is ON or the reject state is ON, the image output control unit 409 judges that an output process has been performed. If there is any image information on which no output process has been performed, the image output control unit 409 returns to step S702. If an output process has been performed on all the pieces of image information, the image output control unit 409 proceeds to step S706. Then, in step S706, the image output control unit 409 transmits an image output completion notification to the examination control unit 406. Thus, the image output process ends.

In the way described above, the image output control unit 409 limits the transmission of data set as a reject to an external device.

In the following, a description will be given of an example display screen displayed on the display unit 109 by the display control unit 4070.

An example of the patient information input screen 801 displayed in step S601 in FIG. 6 will be illustrated with reference to FIG. 8. The patient information input screen 801 is a screen on which information on a patient to be subjected to an examination is input. The patient information input screen 801 is constituted by a patient information input portion 802, a patient information list 803, a patient information confirmation instruction portion 804, a patient information display portion 805, an examination information display portion 806, and an examination start instruction portion 807. The patient information input portion 802 is an area in which values of items included in the patient information are input or selected. In the patient information list 803, pieces of patient information used for examinations conducted in the past are displayed in list form. The patient information list 803 has columns, each showing one of the items included in the patient information. The list has rows, each showing a piece of patient information on one patient. When an arbitrary one of the pieces of patient information in the list is selected, the selected piece of patient information is input to the respective entry portions in the patient information input portion 802. The patient information confirmation instruction portion 804 is a button for confirming the values input to the patient information input portion 802 as patient information. When the button is pressed, it is checked whether values have been input to required input items or whether the values input to the input items are correct or acceptable. If there is no problem, the values are confirmed as patient information. The patient information display portion 805 is an area in which confirmed patient information is displayed. No values are displayed in items until patient information is confirmed, and, at the time when patient information is confirmed, values are displayed. The examination information display portion 806 is an area in which input examination information is displayed. The examination information illustrated here includes information for identifying an examination, such as an examination ID, an inquiring physician's name, a radiologist's name, examination description, and a facility name. In addition, an imaging technique selected as intended for imaging is also included. Note that at least one or more imaging techniques are selectable per examination. The examination information display portion 806 has an area in which items in the examination information are displayed, and an area in which the selected imaging technique or imaging techniques are displayed. No values are displayed in the respective items until examination information is input. Likewise, no imaging techniques are displayed until any imaging technique is selected. Values and an imaging technique are respectively displayed when examination information is input and at the time when the imaging technique is selected. In addition, a plurality of examinations can be conducted at once in a single imaging session. In this case, a number of examination information display portions 806 corresponding to the number of examinations are displayed side by side. The examination start instruction portion 807 is a button for providing an instruction to start an examination. When the button is pressed, it is checked whether patient information and examination information have been input and, in addition, whether one or more imaging techniques have been selected for each examination. If there is no problem, an examination start process is carried out. If there is any examination for which no imaging technique has been selected, the imaging technique selection screen 901 is displayed.

Figure 9:
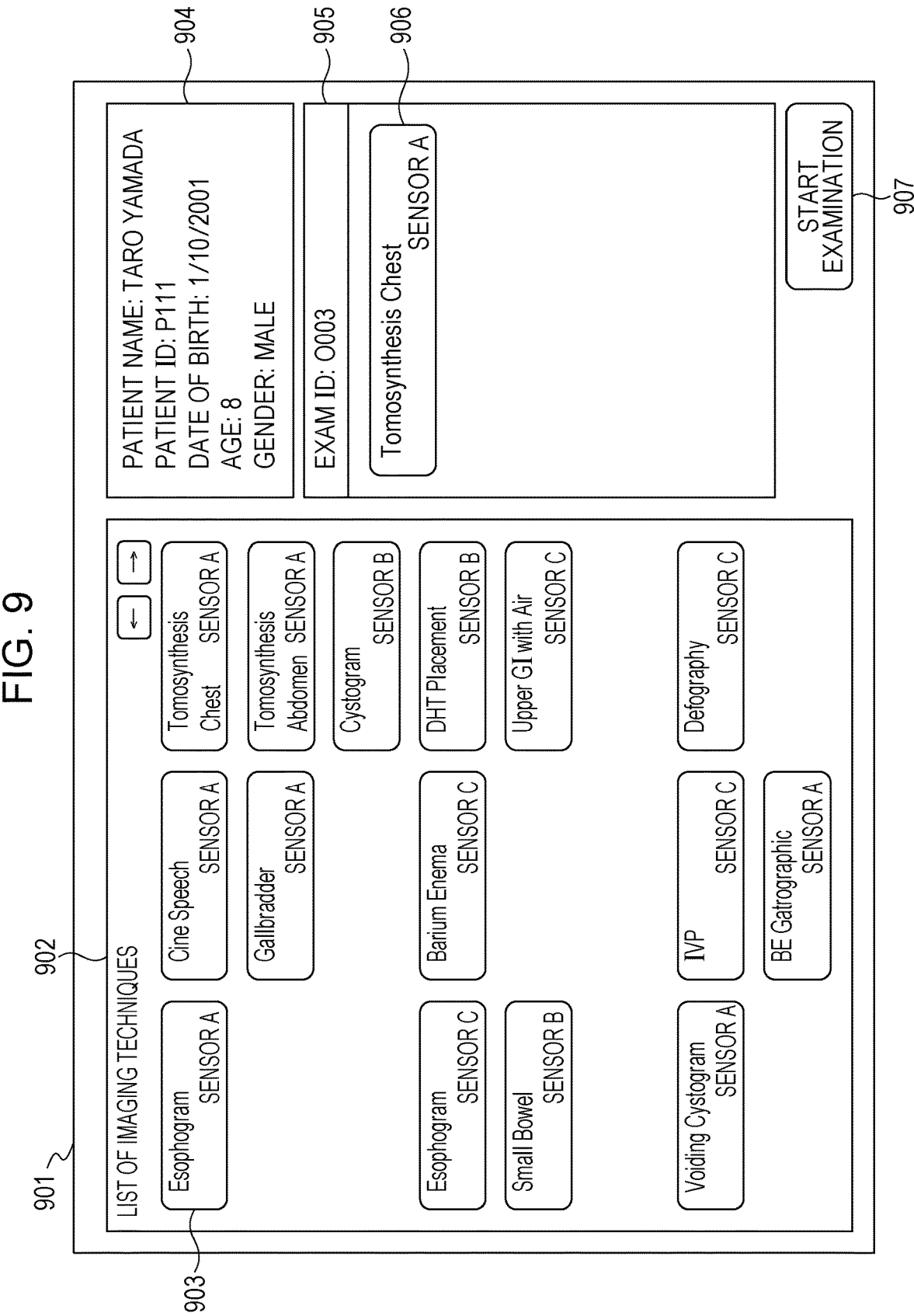
FIG. 9 is a diagram illustrating an imaging technique selection screen according to the embodiment of the present invention.

Next, an example of the imaging technique selection screen 901 displayed in step S602 in FIG. 6 is illustrated using FIG. 9. The imaging technique selection screen 901 is a screen on which an imaging technique intended for imaging in an examination to be conducted is selected. The imaging technique selection screen 901 is constituted by an imaging technique display portion 902, imaging technique buttons 903, a patient information display portion 904, an examination information display portion 905, a selected imaging technique button 906, and an examination start instruction portion 907. The imaging technique display portion 902 is an area in which the imaging techniques saved in the imaging technique information storage unit 402 are displayed one by one by using the imaging technique buttons 903. The locations where the buttons are displayed can be changed as desired. In addition, one page is not sufficient to display all the buttons, the buttons can be displayed over a plurality of pages, in which case the display pages are switched in response to an instruction to switch between pages. The imaging technique buttons 903 are buttons each displayed for one of the imaging techniques saved in the imaging technique information storage unit 402. Each imaging technique button shows the name of an imaging technique and the name of a sensor to be used. When any button is pressed, the selected item is confirmed as intended for imaging in the currently selected examination. The patient information display portion 904 is an area in which confirmed patient information is displayed. The examination information display portion 905 is an area in which input examination information is displayed. As the selected imaging technique button 906, an imaging technique button 903 selected in the imaging technique display portion 902 is displayed. Since one or more imaging techniques are selectable for each examination, another selected imaging technique button 906 is added to the bottom of the examination information display portion 905 each time an imaging technique button is selected. The examination start instruction portion 807 is a button for providing an instruction to start an examination. When the button is pressed, it is checked whether patient information and examination information have been input and, in addition, whether one or more imaging techniques have been selected for each examination. If there is no problem, an examination start process is carried out. When an examination start process is carried out, a transition to the imaging screen 1001 occurs. If there is any examination for which no imaging technique has been selected, the user is prompted to select any imaging technique, and no screen transition occurs. The imaging technique selection screen 901 having the configuration described above is displayed.

Figure 10:
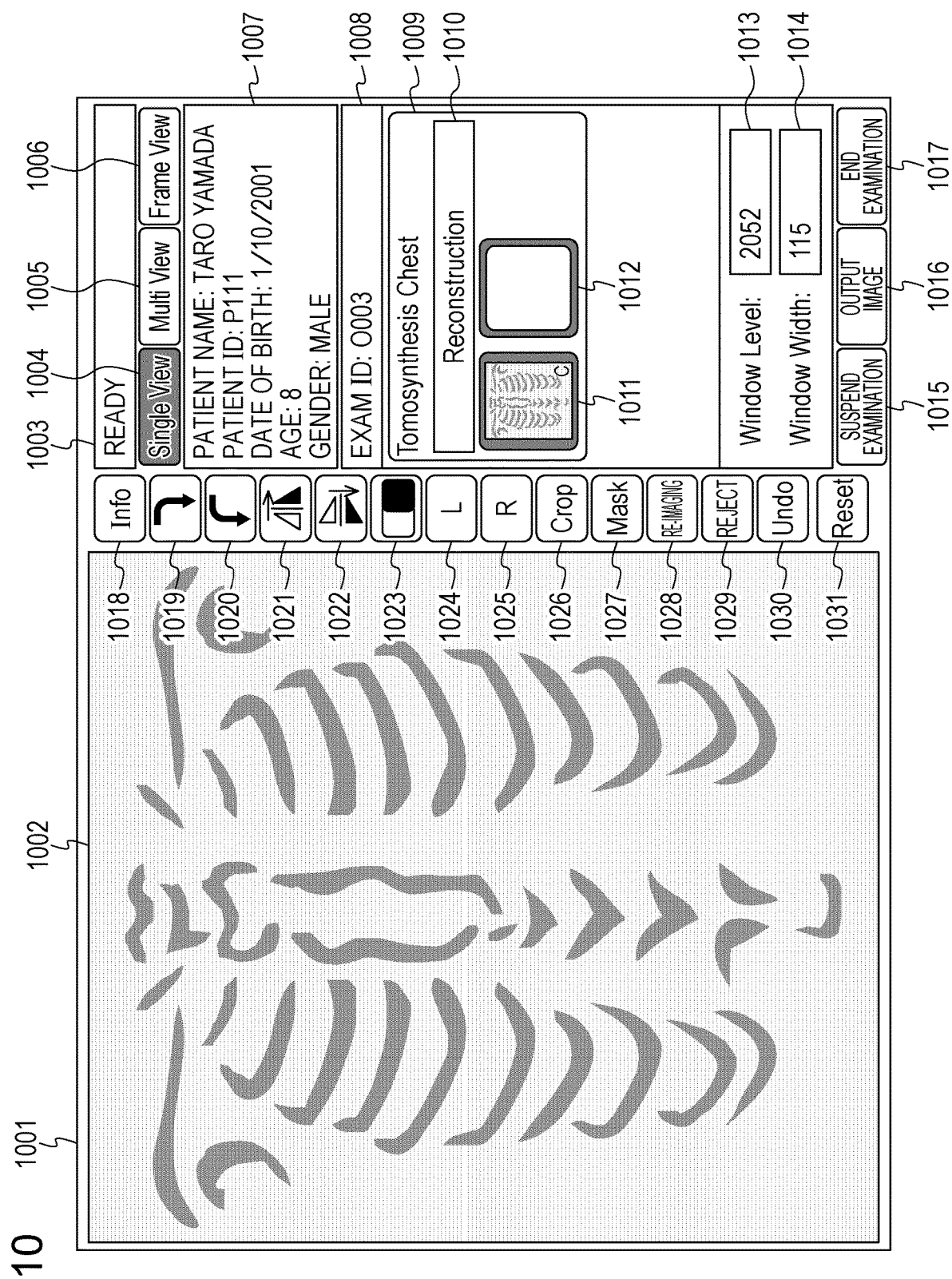
FIG. 10 is a diagram illustrating an imaging screen according to the embodiment of the present invention.

Next, an example of the imaging screen 1001 displayed in step S603 in FIG. 6 is illustrated using FIG. 10. The imaging screen 1001 is constituted by an image display portion 1002, a status display portion 1003, a single-view instruction portion 1004, a multi-view instruction portion 1005, a frame-view instruction portion 1006, a patient information display portion 1007, an examination information display portion 1008, an imaging technique display portion 1009, a reconstruction instruction portion 1010, a captured image thumbnail 1011, an intended-for-imaging thumbnail 1012, a window level editing portion 1013, a window width editing portion 1014, an examination suspension instruction portion 1015, an image output instruction portion 1016, an examination termination instruction portion 1017, an annotation display instruction portion 1018, a clockwise instruction portion 1019, a counterclockwise instruction portion 1020, a horizontal inversion instruction portion 1021, a vertical inversion instruction portion 1022, a white/black inversion instruction portion 1023, an L mark placement instruction portion 1024, an R mark placement instruction portion 1025, a cropping setting instruction portion 1026, a mask processing instruction portion 1027, a re-imaging button 1028, a reject button 1029, an undo instruction portion 1030, and a reset instruction portion 1031. The image display portion 1002 shows a preview of a captured image obtained after still-image imaging or a tomosynthesis image subjected to the reconstruction process. During moving-image imaging, captured images are displayed as previews in real time. If preview selection is switched after imaging, a captured image subjected to preview selection is displayed as a preview. In addition, patient information, examination information, irradiation conditions, and so forth are displayed as annotations in accordance with the settings. No images are displayed in the initial state immediately after the start of an examination. The status display portion 1003 is an area in which the status notified by the X-ray control unit 104 or the X-ray detector 106 is displayed using a distinct color or text to allow the operator to distinguishably identify the status. Upon receipt of a notification of a status from the X-ray control unit 104 or the X-ray detector 106 via the communication circuit 112, the imaging control unit 405 notifies the examination control unit 406 of a change of the status. The examination control unit 406 determines the displayed content in accordance with a combination of statuses of the X-ray control unit 104 or the X-ray detector 106, and transmits a status display switching instruction to the display control unit 4070. For example, if the X-ray control unit 104 is not capable of X-ray irradiation or the X-ray detector 106 is not capable of X-ray detection, "Not Ready" is displayed on the sensor status. If the X-ray control unit 104 is capable of X-ray irradiation and the X-ray detector 106 is capable of X-ray detection, "Ready" is displayed on the sensor status and the background color is changed to a color which is made easily distinguishable from that for the display of "Not Ready". The single-view instruction portion 1004 is a button for switching to a single-view mode in which one frame of an image being selected as a preview is displayed in the image display portion 1002. In the case of images of a plurality of frames, it is also possible to display a different frame or reproduce a moving image during the display of a preview in accordance with a keyboard or mouse operation. The multi-view instruction portion 1005 is a button for switching to a multi-view mode in which the image display portion 1002 is segmented into a plurality of display areas in a lattice pattern and images captured in the examination being conducted are displayed in parallel. The button is disabled and the multi-view mode is not available until two or more images are captured in the examination being conducted. The frame-view instruction portion 1006 is a button for switching to a frame-view mode in which the image display portion 1002 is segmented into a plurality of display areas in a lattice pattern and frame images of a moving image being selected as a preview are displayed in parallel. If the image being selected as a preview is not a moving image, the button is disabled and the frame-view mode is not available. The patient information display portion 1007 is an area in which patient information such as the patient's name and a patient ID is displayed. The examination information display portion 1008 shows examination information such as an examination ID or examination description. Further, imaging techniques selected in the examination are displayed side by side in the imaging technique display portion 1009. The imaging technique display portion 1009 includes the reconstruction instruction portion 1010, the captured image thumbnail 1011, and the intended-for-imaging thumbnail 1012. The imaging technique display portion 1009 shows imaging technique information such as the name of an imaging technique and all the captured image thumbnails 1011 that have been implemented. In the initial state immediately after the start of an examination, no imaging has been performed and thus no captured image thumbnails 1011 are displayed. The reconstruction instruction portion 1010 is a button for providing an instruction to execute a reconstruction process on a tomosynthesis imaging technique including the image currently being selected as a preview. The reconstruction instruction portion 1010 is not displayed for imaging techniques other than tomosynthesis, and the display area is cut out. If a plurality of tomosynthesis imaging techniques are being displayed, all the buttons other than a tomosynthesis imaging technique including the image currently being selected as a preview are disabled. An instruction is given through the reconstruction instruction portion 1010, thereby enabling reconstruction to be re-performed on a tomosynthesis imaging technique which has been subjected to a reconstruction process once. The captured image thumbnail 1011 has displayed thereon a thumbnail image corresponding to each captured image, an imaging type mark, a similarity mark 2301, and a reject mark 2701. The imaging type mark is a mark that makes the types of still-image imaging, fluoroscopic imaging, cine imaging, and tomosynthesis-image imaging distinguishable from one another. For example, cine imaging is represented by "C" and tomosynthesis-image imaging is represented by "T". However, the marks are not limited thereto, and any sign capable of distinguishing imaging types from one another may be used. Selecting the captured image thumbnail 1011 switches preview display. Further, the imaging technique display portion 1009 currently being selected as intended for the next irradiation shows the intended-for-imaging thumbnail 1012, which is displayed as blank, at a location where an additional thumbnail is to be placed when irradiation takes place next time. When the state of being selected as intended for irradiation is released, the intended-for-imaging thumbnail 1012 is made invisible. The window level editing portion 1013 and the window width editing portion 1014 are portions in which the window level and the window width of the image currently being selected as a preview are edited. Changing the values displayed in the edit boxes or dragging the mouse on the image display portion 1002 applies the editing to an image being displayed as a preview. The examination suspension instruction portion 1015 is a button for providing an instruction to suspend the examination being conducted. The examination control unit 406 performs an examination suspension process. The image output instruction portion 1016 is a button for providing an instruction to output a captured image included in the examination being conducted. A process flow when an image output instruction is given is similar to that for the image output process at the end of the examination illustrated in FIG. 7. The examination termination instruction portion 1017 is a button for providing an instruction to terminate the examination being conducted. The examination control unit 406 performs an examination termination process. The annotation display instruction portion 1018 is a button for switching the visibility of an annotation displayed in the image display portion 1002. The clockwise instruction portion 1019 is a button for allowing a captured image being displayed as a preview to rotate clockwise. The counterclockwise instruction portion 1020 is a button for allowing a captured image being displayed as a preview to rotate counterclockwise. The horizontal inversion instruction portion 1021 is a button for horizontally inverting a captured image being displayed as a preview. The vertical inversion instruction portion 1022 is a button for vertically inverting a captured image being displayed as a preview. The white/black inversion instruction portion 1023 is a button for inverting the window value of a captured image being displayed as a preview. The L mark placement instruction portion 1024 is a button for placing the laterality marker "L" on a captured image being displayed as a preview. The button is on/off switchable, where "L" is placed when the button is on and "L" is removed when the button is off. The R mark placement instruction portion 1025 is a button for placing the laterality marker "R" on a captured image being displayed as a preview. The button is on/off switchable, where "R" is placed when the button is on and "R" is removed when the button is off. The cropping setting instruction portion 1026 is a button for providing an instruction to set the cropping settings for a region of interest in a captured image being displayed as a preview. The mask processing instruction portion 1027 is a button for providing an instruction to perform mask processing on a captured image being displayed as a preview. The re-imaging button 1029 is a button for providing an instruction to perform re-imaging on an imaging technique including an image currently being selected as a preview. The term re-imaging, as used herein, refers to a process for executing a reject process on an image specified in a re-imaging instruction and newly adding the same imaging technique. The reject button 1029 is a button for providing a reject instruction for an image currently being selected as a preview. When a reject process is executed, a reject setting included in the image information is switched to ON. The undo instruction portion 1030 is a button for providing an instruction to perform undo processing to return a history of processes on an image currently being selected as a preview to a new order. The reset instruction portion 1031 is a button for providing an instruction to perform a reset process for discarding all the processes for an image currently being selected as a preview and returning the state to a state obtained immediately after imaging. The imaging screen 1001 having the configuration described above is displayed.

The display control unit 4070 causes an imaging technique for capturing a projected image group to be displayed in the imaging technique display portion 1009 (first display area) on the foregoing imaging screen 1001. In response to the capture of a projected image group corresponding to the imaging technique, a captured image thumbnail 1011 representing the projected image group is displayed in the imaging technique display portion 1009. Further, in response to the generation of a tomosynthesis image based on the projected image group, the display control unit 4070 causes a captured image thumbnail 1011 of the tomosynthesis image to be displayed in the imaging technique display portion 1009 (first display area). Doing so provides an intelligible display of imaging information and its corresponding projected image group and tomosynthesis image.

Figure 11:
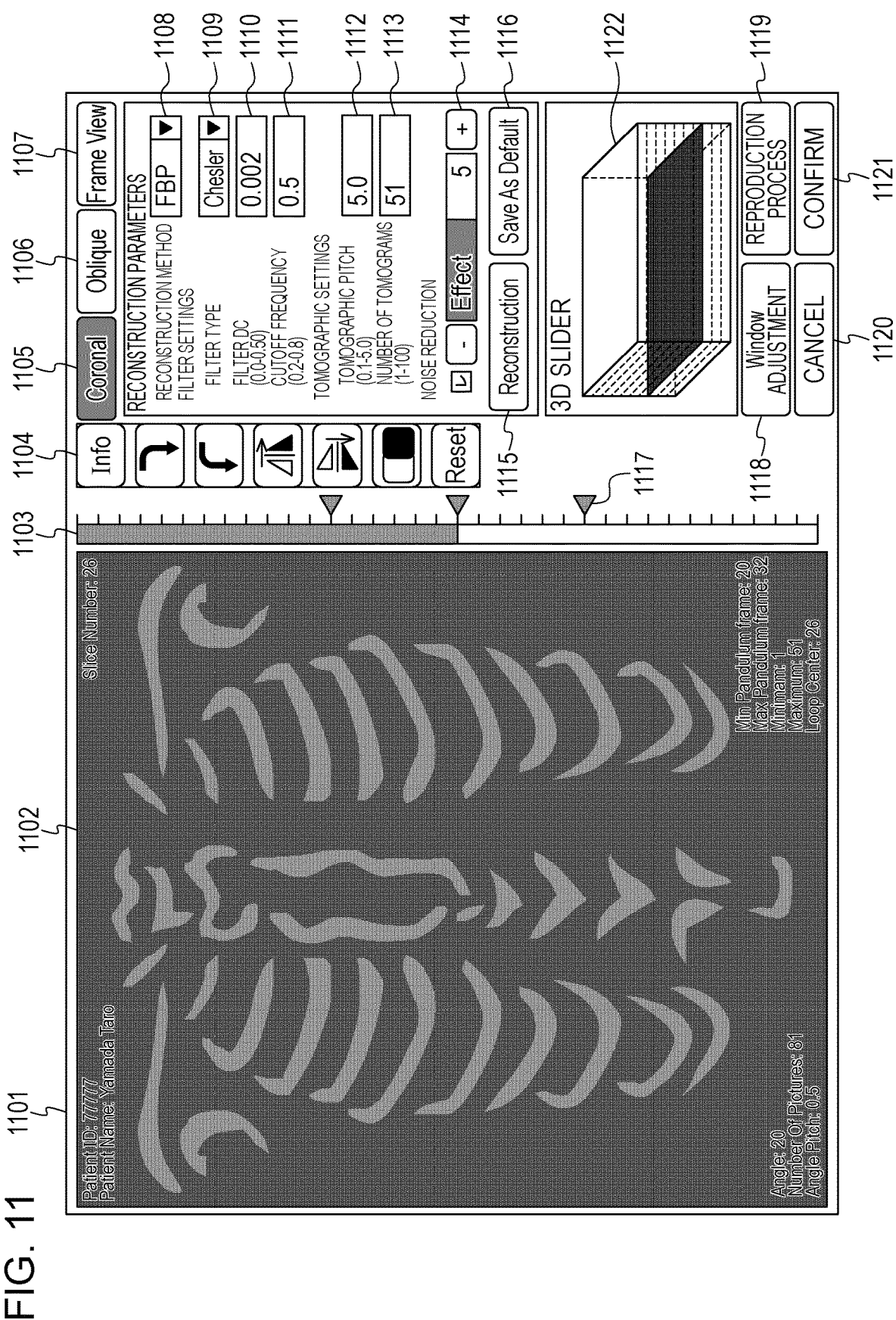
FIG. 11 is a diagram illustrating a reconstruction screen according to the embodiment of the present invention.

Next, an example of the reconstruction screen 1101 displayed in step S609 in FIG. 6 is illustrated using FIG. 11. The reconstruction screen 1101 is constituted by an image display portion 1102, a frame specifying slider 1103, an image operation toolbar 1104, a coronal cross section display instruction portion 1105, an oblique cross section display instruction portion 1106, a frame-view instruction portion 1107, a reconstruction method selection portion 1108, a reconstruction filter type selection portion 1109, a reconstruction filter DC editing portion 1110, a cutoff frequency editing portion 1111, a tomographic pitch editing portion 1112, a number-of-slice editing portion 1113, a noise reduction process editing portion 1114, a reconstruction process instruction portion 1115, a default settings instruction portion 1116, a frame reproduction range setting portion 1117, a window adjustment display instruction portion 1118, a reproduction process display instruction portion 1119, a reconstruction cancellation instruction portion 1120, a reconstruction confirmation instruction portion 1121, and a 3D slider 1122. The image display portion 1102 shows a preview of a tomosynthesis image subjected to the reconstruction process. During the ongoing reconstruction process, a progress bar notifying the user that the reconstruction process is in progress is displayed, and a tomosynthesis image is displayed at the same time as the completion of the reconstruction process. The frame specifying slider 1103 is used to check a frame image being displayed in a tomosynthesis image being displayed as a preview and to switch between frame images. At the same time as the display of a preview of the tomosynthesis image, memories for all the valid frames of the tomosynthesis image being displayed as a preview are equally displayed from the upper end to the lower end along the slider. Control is performed so that only valid frames can be specified, thereby reducing the risk of erroneous display of invalid frames. A frame having a number corresponding to a memory selected by selection or dragging across the frame specifying slider 1103 is displayed in the image display portion 1102. The image operation toolbar 1104 has arranged thereon controls for providing instructions to perform processes on the tomosynthesis image being displayed as a preview. The arranged controls are similar to 918 to 931 on the imaging screen 1001.

The coronal cross section display instruction portion 1105 is a button for providing an instruction that the tomosynthesis image displayed in the image display portion 1102 be displayed on a coronal cross section, and corresponds to a button for providing an instruction to display a first two-dimensional tomographic image. This button is made selectable in the initial state where the reconstruction screen 1101 in FIG. 11 is displayed, and is also in an on state (selected state). The oblique cross section display instruction portion 1106 is a button for providing an instruction that the tomosynthesis image displayed in the image display portion 1102 be displayed on an oblique cross section, and corresponds to a button for providing an instruction to display a second two-dimensional tomographic image.

The frame-view instruction portion 1107 is a button for switching to a frame-view mode in which the image display portion 1102 is segmented into a plurality of display areas in a lattice pattern and frame images of a tomosynthesis image being displayed as a preview are displayed in parallel. The button is disabled and frame-view display is not available during oblique cross section display. The reconstruction method selection portion 1108 is a control for selecting a reconstruction method such as the FBP (Filtered Back Projection) method, the shift-and-add method, or the iterative reconstruction method. The reconstruction filter type selection portion 1109 is a control for selecting the type of a filter to be used for the reconstruction process. The reconstruction filter DC editing portion 1110 is a control for editing the DC parameter for the filter to be used for the reconstruction process. The cutoff frequency editing portion 1111 is a control for editing the cutoff frequency of the filter to be used for the reconstruction process. The tomographic pitch editing portion 1112 is a control for editing the thickness between frames during the reconstruction process. The number-of-slice editing portion 1113 is a control for editing the total number of frames during the reconstruction process. The noise reduction process editing portion 1114 is a control for switching whether or not to apply a noise reduction process during the reconstruction process and for editing the degree of severity of the application of the noise reduction process. The reconstruction process instruction portion 1115 is a button for providing an instruction to execute a reconstruction process. Reconstruction is executed again by using a reconstruction parameter that has been input at the time when the button is pressed. In this case, the same projected images as those for the tomosynthesis image being displayed as a preview are used. The default settings instruction portion 1116 is a button for providing an instruction to change the default reconstruction parameters of the tomosynthesis imaging technique being displayed as a preview. When the button is pressed, a reconstruction parameter change notification together with the currently displayed reconstruction parameters is transmitted from the imaging control unit 405 to the examination control unit 406. The examination control unit 406 updates the reconstruction parameters of the tomosynthesis imaging technique which is the target of the reconstruction parameters, and transmits a "registration/update" process request to the imaging technique information storage unit 402. The frame reproduction range setting portion 1117 is a control for specifying a reproduction range during range-specified reciprocal reproduction. The frame reproduction range setting portion 1117 is constituted by knobs for specifying a minimum frame number, a center frame number, and a maximum frame number. Moving the respective knobs allows a range from the specified minimum frame number to the specified maximum frame number to be set as a reproduction range. The window adjustment display instruction portion 1118 is a button for switching the visibility of a window adjustment control. When the window adjustment display instruction portion 1118 is switched to ON, a window adjustment portion 1601 is displayed in the 3D slider 1122 display area.

The image processing unit 110 according to the embodiment performs an analysis process of a tomosynthesis image, and subjects a slice image generated from the tomosynthesis image, such as a coronal image or an oblique image, to tone conversion processing such as window processing. The display control unit 4070 causes the slice image subjected to the window processing to be displayed in the image display portion 1102 on the reconstruction screen 1101.

When the window adjustment display instruction portion 1118 is switched to OFF, the window adjustment portion 1601 is made invisible and the 3D slider 1122 is displayed. The reproduction process display instruction portion 1119 is a button for switching the visibility of a reproduction process control. When the reproduction process display instruction portion 1119 is switched to ON, a reproduction processing portion 2001 is displayed in the 3D slider 1122 display area. When the reproduction process display instruction portion 1119 is switched to OFF, the reproduction processing portion 1601 is made invisible and the 3D slider 1122 is displayed. The reconstruction cancellation instruction portion 1120 is a button for providing an instruction to discard the tomosynthesis image being previewed. When an instruction for canceling reconstruction is given, step S609 is completed without the storage of the tomosynthesis image and the image information, and a transition to the imaging screen 1001 occurs. On the imaging screen 1001, an image which has been previewed before the reconstruction screen is displayed is continuously selected as a preview. The reconstruction confirmation instruction portion 1121 is a button for providing an instruction to confirm the storage of the tomosynthesis image being previewed. When an instruction for confirming the storage is given, the tomosynthesis image being previewed is saved in the HDD 504. Thereafter, step S608 is completed, and a transition to the imaging screen 1001 occurs.

The 3D slider 1122 is a control for providing a pseudo-3D display of a frame of the generated tomosynthesis image and specifying a display frame. The 3D slider 1122 has displayed thereon ruled lines depicting a relative positional relationship between frames of each tomosynthesis image, and a small image is displayed at the position of the same frame number as a display frame image. Selecting a ruled line on the 3D slider 1122 or dragging the mouse can facilitate switching between display frames. As the ruled lines displayed on the 3D slider 1122, those for only valid frames of a tomosynthesis image are displayed. In addition, in association with the editing of the tomographic pitch or the number of slices, the positional relationship between frames of each tomosynthesis image subjected to the reconstruction process is displayed as a preview so as to be superimposed on the current state. This enables the operator to easily understand a change in thickness when changing the tomographic pitch or the number of slices. The reconstruction screen 1101 having the configuration described above is displayed.

Figure 12:
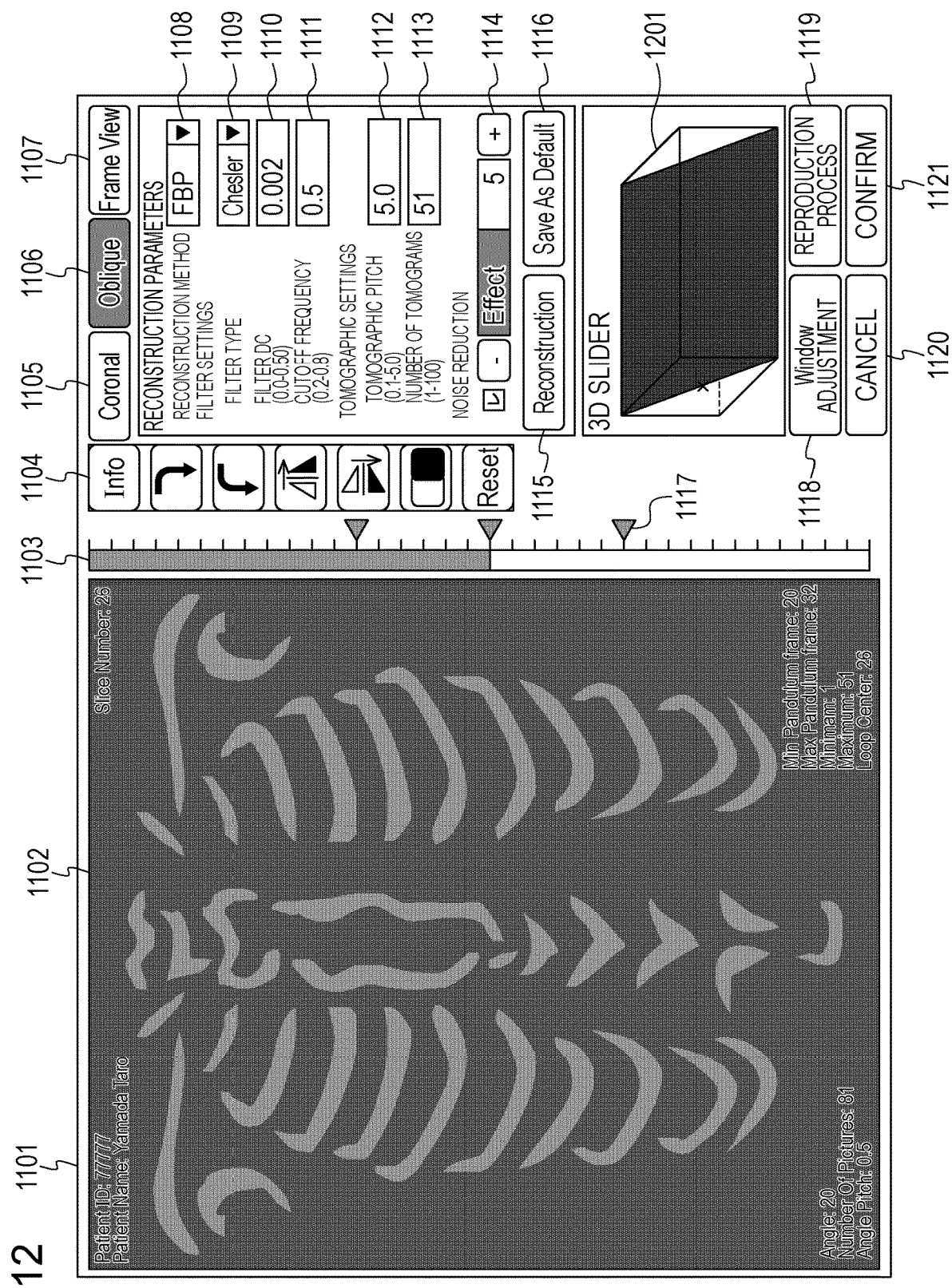
FIG. 12 is a diagram illustrating an oblique cross section display screen on the reconstruction screen according to the embodiment of the present invention.

Next, the reconstruction screen 1101 displayed in step S609 in FIG. 6 for the display of an oblique cross section is illustrated using FIG. 12. When the oblique cross section display instruction portion 1106 is pressed, the cross section of the tomosynthesis image displayed in the image display portion 1102 is switched from a coronal cross-sectional image to an oblique cross-sectional image. When the coronal cross section display instruction portion 1105 is pressed, the cross section of the tomosynthesis image displayed in the image display portion 1102 is switched from a coronal cross section to an oblique cross section. During the display of an oblique cross section, the specification of a frame by using the frame specifying slider 1103 or any reproduction instruction from the reproduction processing portion 1901 is ignored. In addition, the frame-view instruction portion 1107 is disabled, and the frame-view mode is not available. During the display of an oblique cross section, an oblique-angle editing 3D slider 1201 is displayed in place of the typical 3D slider 1122. The oblique-angle editing 3D slider 1201 is a display area in which posture information of an oblique cross-sectional image displayed in the image display portion 1102 appears. In the oblique-angle editing 3D slider 1201, a direction along an upper surface and a lower surface of an illustrated rectangular parallelepiped corresponds to the direction of a coronal cross-sectional image, and a presentation of posture information of an oblique cross-sectional image crossing the coronal cross-sectional image is provided.

Further, the oblique cross-sectional image illustrated in FIG. 12 is an image of a cross section that always extends through the isocenter. The isocenter is represented as a cross mark on a side surface of the illustrated rectangular parallelepiped. In another embodiment, the image processing unit 110 generates an oblique cross-sectional image at a position that does not pass through the isocenter, and the display control unit 4070 can cause the oblique cross-sectional image to be displayed in accordance with the operation input from the operation unit 108.

The editing of the display angle of a frame image displayed on the oblique-angle editing 3D slider 1201 results in the oblique angle being changed accordingly. In association with the oblique angle edited in the oblique-angle editing 3D slider 1201, the oblique angle of the tomosynthesis image displayed as a preview in the image display portion 1102 is also changed. The reconstruction screen 1101 having the configuration described above for the display of an oblique cross section is displayed.

<Oblique Display Limitation Process>

Here, an example of a process related to the display of a reconstruction screen from the start of irradiation for projected images, which is executed in step S608 and step S609 in FIG. 6, is illustrated using FIG. 13. The process illustrated in FIG. 13 is performed by, for example, the imaging control device 107 illustrated in FIG. 1. First, in step S1301, the irradiation switch 103 is pressed to start irradiation, and projected images are sequentially captured.

In S1302, the pressing of the irradiation switch 103 is released to terminate irradiation, and the capture of projected images is completed. Upon receipt of a projected image irradiation end notification, the imaging control unit 405 transmits an imaging interruption determination request notification to the imaging interruption determination unit 401. The imaging interruption determination request notification includes image information on the projected images, and position information.

Here, the imaging interruption determination unit 401 determines the situation in which interruption of imaging is occurring by using the image information on the projected images and the position information, and notifies the imaging control unit 405 of an imaging interruption determination result. The imaging interruption determination result includes a determination status, the determination status including "no position information", "interrupted in initial stage", "interrupted in later stage", and "completed".

In step S1303, upon receipt of the imaging interruption determination request notification, the imaging interruption determination unit 401 checks the position information. If no position information is included, the imaging interruption determination unit 401 sets the determination status to "no position information", and transmits the imaging interruption determination result to the imaging control unit 405.

If position information is included, in step S1304, the progress level measuring unit 4011 checks the imaging state. The progress level measuring unit 4011 refers to either the imaging angle included in the position information or the X-ray detector moving distance, and determines a maximum value (FIG. 3). If the maximum value is a negative value, the imaging interruption determination unit 401 determines interruption of the imaging at less than 0°, and sets the determination status to "interrupted in initial stage". If the initial position at the start of imaging begins with a positive value, the imaging interruption determination unit 401 refers to either the imaging angle included in the position information or the X-ray detector moving distance, and determines a minimum value. If the minimum value is a positive value, the imaging interruption determination unit 401 determines that the imaging has been interrupted at less than 0°, and sets the determination status to "interrupted in initial stage". Subsequently, the progress level measuring unit 4011 compares the maximum value of the imaging angle or X-ray detector moving distance with the maximum imaging angle included in the default imaging conditions or the maximum X-ray detector moving distance. If the maximum value of the position information is less than the maximum imaging angle or the maximum X-ray detector moving distance by a certain threshold value, the imaging interruption determination unit 401 determines interruption of the imaging at 0° or greater, and sets the determination status to "interrupted in later stage". If the minimum value of the imaging angle or X-ray detector moving distance is used, the minimum value is compared with the minimum imaging angle included in the default imaging conditions or the minimum X-ray detector moving distance. Thereafter, the imaging interruption determination unit 401 transmits the imaging interruption determination result to the imaging control unit 405.

Upon receipt of the imaging interruption determination result, the imaging control unit 405 checks the determination status. If the determination status indicates "no position information", "interrupted in initial stage", or "interrupted in later stage", the imaging control unit 405 transmits an imaging interruption notification to the examination control unit 406. Upon receipt of the imaging interruption notification, the examination control unit 406 updates the status of the target imaging technique information.

Then, in step S1305, the examination control unit 406 checks the status of the imaging technique information.

If the status indicates "no position information" in step S1305, then in step S1312, the examination control unit 406 displays a pop-up screen 1401 on the imaging screen 1001. When the pop-up screen 1401 is closed, the examination control unit 406 ends the process without a transition to a reconstruction screen.

If the status indicates "initial stage" in step S1305, then in step S1313, the examination control unit 406 displays a pop-up screen 1601 on the imaging screen 1001. When the pop-up screen 1601 is closed, the examination control unit 406 transmits a reconstruction prohibition notification to the display control unit 4070 without a transition to a reconstruction screen. The reconstruction transmission notification includes imaging technique information.

Then, in step S1316, upon receipt of the reconstruction prohibition notification, the display control unit 4070 transmits the reconstruction prohibition notification to the display unit 109. Upon receipt of the reconstruction prohibition notification, the display unit 109 disables the display of the reconstruction instruction portion 1010 in the imaging screen 1001, and then the process ends.

If the to-be-implemented determination status indicates "completed" in step S1305, then in step S1306, the imaging control unit 405 compares the number of acquired frames of projected images with the number of elements of position information.

If the number of acquired frames of projected images is different from the number of elements of position information in step S1306, then in step S1307, the imaging control unit 405 carries out a correction process to make the number of acquired frames of projected images and the number of elements of position information identical. At the same time, the imaging control unit 405 transmits a correction process accomplishment notification to the examination control unit 406. Upon receipt of the correction process accomplishment notification, the examination control unit 406 updates information on the presence or absence of a correction process for the target imaging technique information.

If the number of acquired frames of projected images and the number of elements of position information are identical in step S1306, no correction process is carried out.

In step S1308, the imaging control unit 405 carries out a reconstruction process. The process flow of steps S1308 to S1309 is similar to the process flow of S608 to S609 in FIG. 6. After a tomosynthesis image has been displayed on the reconstruction screen 1101, in step S1310, the examination control unit 406 checks the status of imaging technique information including the displayed tomosynthesis image.

In the way described above, even if the imaging ends in step S1302 due to the interruption of the imaging, in the situation where the imaging proceeds at 0° or greater (half or more finished), in S1308, the image processing unit 110 is caused to execute a reconstruction process on the basis of projected images obtained through the interrupted imaging. Then, a coronal image (first two-dimensional tomographic image) is displayed. In contrast, the display of an oblique image (second two-dimensional tomographic image) is prohibited, leading to less likelihood of false diagnosis.

In addition, in the way described above, even if the imaging ends in step S1302 due to the interruption of the imaging, the processes from step S1303 to step S1308 are sequentially executed, thereby enabling a reconstruction process to be started based on projected images obtained in accordance with the interrupted imaging. This enables a diagnostic image to be efficiently obtained while saving the time and labor of the operator.

Here, in another embodiment, only when the imaging ends due to the interruption of the imaging, the display control unit 4070 causes the display unit 109 to display a GUI for accepting an operation input indicating whether or not to start a reconstruction process before the image processing unit 110 executes the reconstruction process in step S1308. The GUI includes, for example, a message indicating "The imaging has been interrupted but you can perform a reconstruction process on a coronal image. Do you wish to start a reconstruction process?", and a pop-up window having an OK button and a Cancel button which can be pressed in accordance with an operation of the operation unit 108. This pop-up window is displayed superimposed on, for example, the examination screen illustrated in FIG. 10. When the input detection unit 4071 detects the pressing of the OK button in accordance with the operation input from the operation unit 108, the imaging control unit 405 causes the image processing unit 110 to start a reconstruction process in accordance with the detection. Doing so can reduce the execution of a reconstruction process unnecessary for the user, and achieve efficient execution of tomosynthesis imaging.

In step S1310, the display control unit 4070 limits the display of a two-dimensional tomographic image intersecting the detection surface of the X-ray detection unit in accordance with the degree of progress of imaging of projected images. If the status indicates "interrupted in later stage", in step S1314, the examination control unit 406 displays a pop-up screen 1601 on the reconstruction screen 1101. When the pop-up screen 1601 is closed, the examination control unit 406 transmits an oblique display prohibition notification to the display control unit 4070.

Then, in step S1317, upon receipt of the oblique display prohibition notification, the display control unit 4070 transmits the oblique display prohibition notification to the display unit 109. Upon receipt of the oblique display prohibition notification, the display unit 109 disables the display of the oblique display instruction portion 1106 on the reconstruction screen 1101, and limits the display of a two-dimensional tomographic image (second two-dimensional tomographic image, oblique image) intersecting the detection surface of the X-ray detector 106.

In the manner described above, if it is determined that the imaging has been interrupted by using the position information from the X-ray control unit 104, the display control unit 4070 performs control so that the oblique display instruction portion 1106 for providing an instruction to display an oblique image (second two-dimensional tomographic image) is not selectable. Accordingly, the display of an oblique image is prohibited. Doing so can reduce the probability that an image which is diagnostically inappropriate for the user will be displayed.

If the status does not indicate "interrupted in later stage" in step S1310, then in step S1311, the examination control unit 406 checks information on the presence or absence of a correction process for the imaging technique information.

If a correction process is present in step S1311, then in step S1315, the examination control unit 406 displays a pop-up screen 1701 on the reconstruction screen 1101. When the pop-up screen 1701 is closed, the examination control unit 406 transmits an oblique display permission notification to the display control unit 4070.

In step S1318, upon receipt of the oblique display permission notification, the display control unit 4070 transmits the oblique display permission notification to the display unit 109. Upon receipt of the oblique display permission notification, the display unit 109 enables the display of the oblique display instruction portion 1106 on the reconstruction screen 1101, and then the process ends.

In the example described above, after the image processing unit 110 has carried out a reconstruction process of three-dimensional volume data in S1308, the display control unit 4070 limits display in S1317 or the like. However, the embodiment is not limited thereto. In another exemplary embodiment, prior to the process of step S1318, the image processing unit 110 directly reconstructs a plurality of oblique images (second two-dimensional tomographic images) from projected images. This allows oblique images to be directly reconstructed from projected images, and can improve image quality. On the other hand, if the process proceeds to step S1314, the oblique image generation process is not performed by the control of the imaging control unit 405. By doing so, no generation process is performed for unnecessary oblique images, leading to efficient processing.

An example of the pop-up screen 1401 displayed on the reconstruction screen 1101 when it is judged in step S1312 in FIG. 13 that there is no notification of position information is illustrated using FIG. 14(a). The pop-up screen 1401 is displayed on the imaging screen 1001. The pop-up screen 1401 shows a message indicating that reconstruction is not available since there is no notification of position information, and an OK button 1402. When the OK button 1402 is pressed, the pop-up screen 1401 is closed, making an operation available on the imaging screen 1001. The pop-up screen 1401 having the configuration described above is displayed. Note that position information may possibly be transmitted later with a delay. Accordingly, the display of the reconstruction process instruction portion 1010 is enabled, and, if a notification of position information has been received at the time of pressing, reconstruction is carried out. If no notification of position information has been received at the time of pressing, the pop-up screen 1401 is displayed again.

An example of a pop-up screen 1403 displayed on the reconstruction screen 1101 when it is judged in step S1313 in FIG. 13 that the capture of projected images has been interrupted at less than 0° is illustrated using FIG. 14(b). The pop-up screen 1403 is displayed on the imaging screen 1001. The pop-up screen 1403 shows a message indicating that reconstruction is not available since the imaging has been interrupted, and an OK button 1404. When the OK button 1404 is pressed, the pop-up screen 1401 is closed, making an operation available on the imaging screen 1001. In addition, for an imaging technique for which the capture of projected images has been interrupted at less than 0°, the reconstruction process instruction portion 1010 is disabled, and it is not possible to execute reconstruction. For example, displaying a cross mark 1405 over the reconstruction process instruction portion 1010 enables the disablement of the reconstruction process instruction portion 1010 to be more clearly presented.

Figure 15:
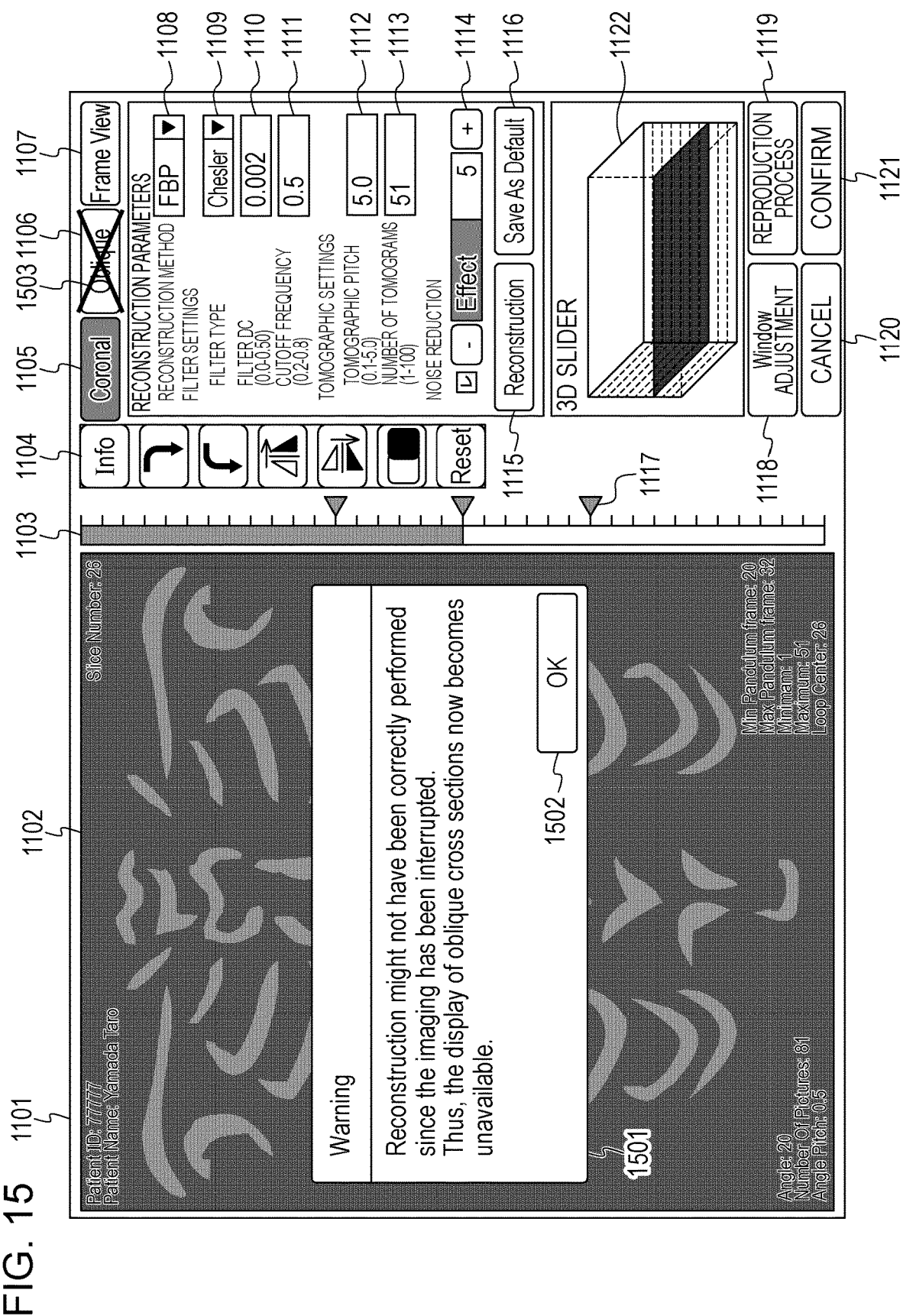
FIG. 15 is a diagram illustrating the reconstruction screen according to the embodiment of the present invention in a case where imaging is interrupted at 0° or greater.

Here, an example of a pop-up screen 1501 displayed on the reconstruction screen 1101 when the capture of projected images has been interrupted at 0° or greater in step S1314 in FIG. 13 is illustrated using FIG. 15. The pop-up screen 1501 is displayed on the reconstruction screen 1101. The pop-up screen 1501 shows a message indicating that reconstruction might not have been correctly performed since the imaging has been interrupted and that the display of oblique cross sections now becomes unavailable, and an OK button 1502. When the OK button 1502 is pressed, the pop-up screen 1501 is closed. In addition, if the capture of projected images has been interrupted at 0° or greater, the oblique cross section display instruction portion 1106 is disabled, making the display of an oblique cross section unavailable. For example, displaying a cross mark 1503 over the oblique cross section display instruction portion 1106 enables the disablement of the oblique cross section display instruction portion 1106 to be more clearly identified.

As in FIG. 14(b) and FIG. 15 described above, the display control unit 4070 causes a warning to be displayed at the time of the interruption of imaging, allowing it to be clarified that the imaging has been interrupted before the imaging of a predetermined range has been completed. In addition, as in FIG. 15, the display control unit 4070 causes a different warning to be displayed in accordance with the level of progress of imaging or the degree of advancement, allowing the user to readily recognize that a different process has been performed in accordance with the degree of advancement.

In another embodiment, even if it is determined in step S1310 that an interruption has occurred in the situation of imaging at 0° or greater, the oblique cross section display button is not disabled. This implies that whether an image can be used for diagnosis or not is deferred to the judgment of a person who is responsible for diagnosis, and the display control unit 4070 causes the display unit 109 to display an oblique image based on an X-ray projected image obtained by exposing the person being examined to X-rays. In this case, the display control unit 4070 performs display control to, when displaying an oblique image, also display an indication of a diagnostically unsuitable image. For example, the indication of a diagnostically unsuitable image is, for example, a message indicating "The quality of reconstructed images might be affected as a result of the interruption of the desired imaging operation", and, in addition, the display control unit 4070 causes an oblique image to be displayed. Alternatively, in a case where an oblique image of a certain posture is output to outside as a DICOM image, the image processing unit 110 embeds the text message described above into the image as image data. This can lead to less likelihood of false diagnosis because such an image may be misinterpreted as an image captured through a correct procedure.

In another embodiment, for example, the following situation is considered. Settings are made such that projected images obtained at irradiation positions from −30° to +30° are captured. It is assumed that, because of the interruption of imaging, only projected images from −30° to +10° have been successfully obtained. In this case, it is considered that quality equal to or more than that for reconstructed images based on projected images obtained at irradiation positions from at least −10° to +10° is assured. In addition, in a case where projected images are obtained by imaging over a range of ±30°, it is assumed that the intersection angle of an oblique image can be varied up to ±30°. In a case where projected images are obtained by imaging over a range of ±10°, it is assumed that the intersection angle of an oblique image can be varied up to ±10°. In this case, the display control unit 4070 performs control so that an oblique image based on projected images obtained through the interrupted imaging described above has an intersection angle which is variable over a range of ±10°.

Accordingly, in the manner described above, if imaging is interrupted midway under a first imaging condition, this situation is handled similarly to that for a second imaging condition which at least provides equal or higher image quality based on projected images obtained before interruption and based on position information. Specifically, the display control unit 4070 causes the display of oblique images over a range similar to that when imaging is performed under the second imaging condition.

By doing so, even if imaging is interrupted, obtained X-ray projected images can be effectively utilized as long as image quality is assured.

In the embodiment described above, the communication circuit 112 of the imaging control device 107 transmits driving conditions and also transmits irradiation conditions for the X-ray generation unit 102. However, the embodiment is not limited thereto. For example, irradiation conditions for the X-ray generation unit may be directly input through an operation unit (not illustrated) of the X-ray control unit 10, and the communication circuit 112 may receive the input irradiation conditions serving as setting conditions and irradiation conditions serving as execution information used for the actual imaging.

Examples of the reconstruction algorithm for the image processing unit 110 may also include the iterative reconstruction method in addition to the FBP method (Filtered Back Projection) and the shift-and-add method.

While the emission of pulsed X-rays has been described in the embodiment described above, this is not to be taken in a limiting sense. Alternatively, X-rays may be continuously emitted, and the X-ray detector may detect the X-rays to obtain projected images. In this case, the positions of the X-ray generation unit 102 and the X-ray detector 106 differ between at the start of X-ray irradiation and at the end of X-ray irradiation in terms of units of projected images. In this case, it may be sufficient to perform a reconstruction process by using a positional relationship obtained at a certain timing from the start of X-ray irradiation to the end of X-ray irradiation as geometric information for which the projected images have been captured.

Figure 16:
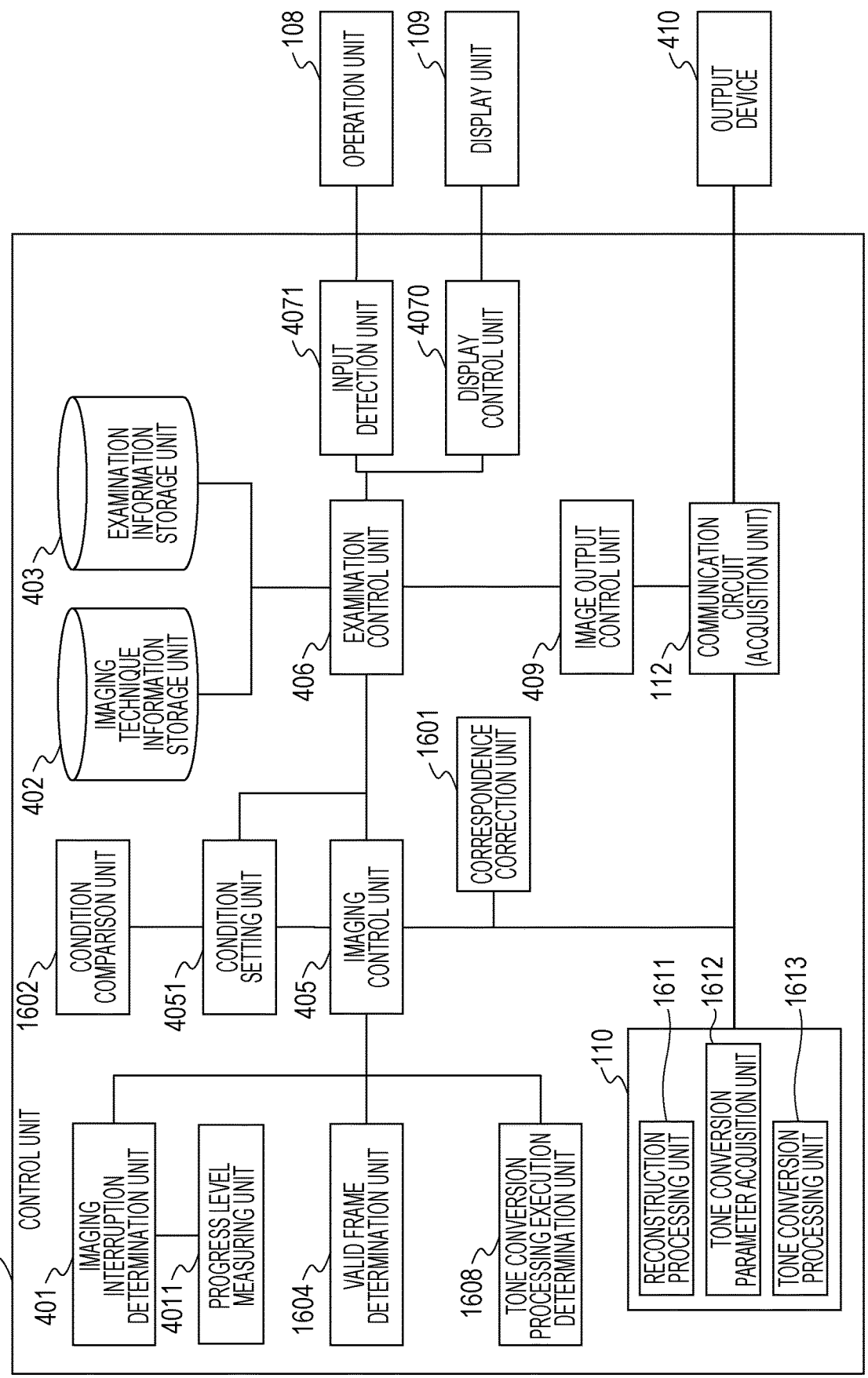
FIG. 16 is a diagram illustrating the configuration of an imaging control device 107 according to another embodiment of the present invention.
Figure 19:
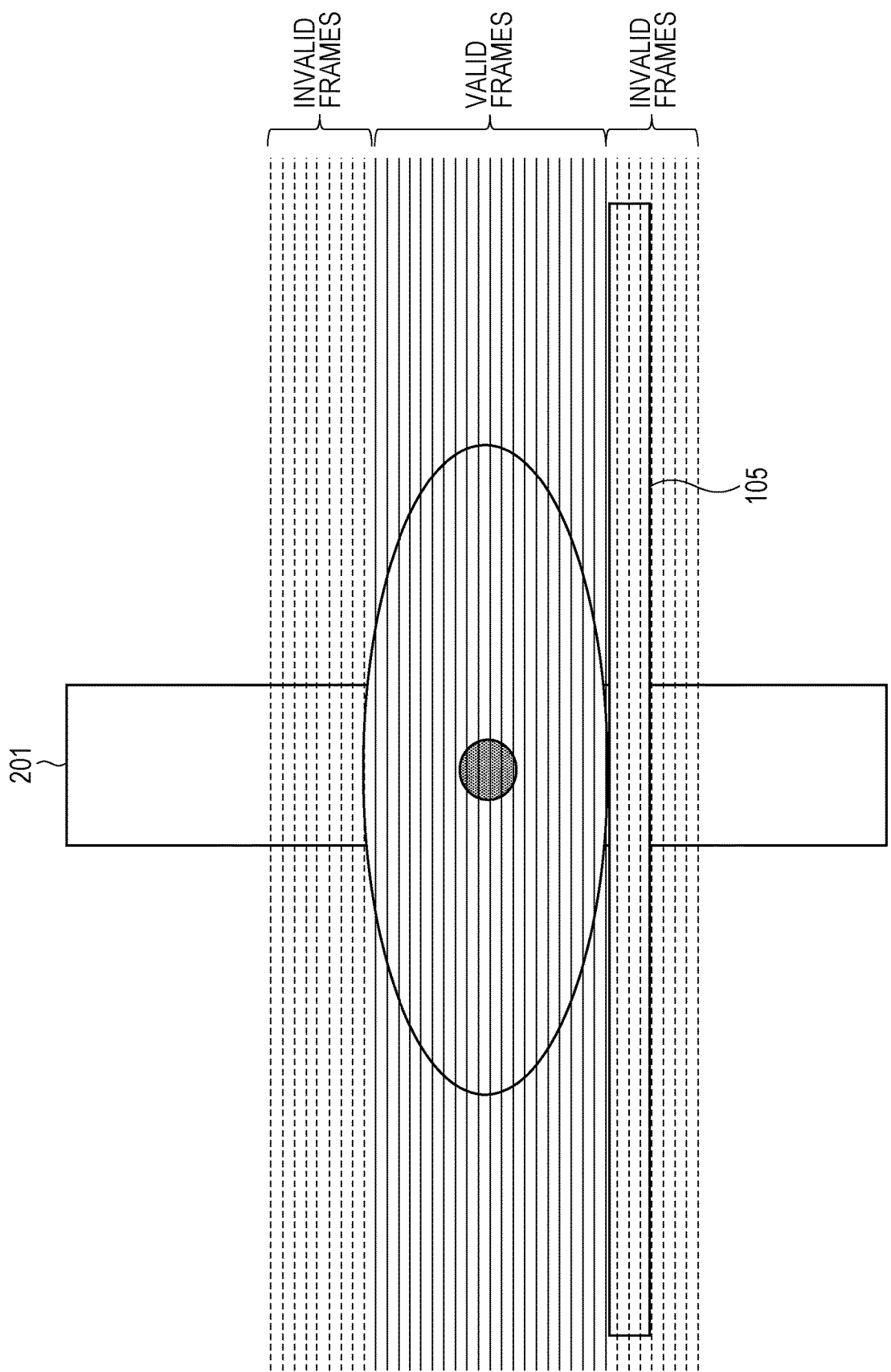
FIG. 19 is a diagram illustrating valid frames and invalid frames in a tomosynthesis image.
Figure 21:
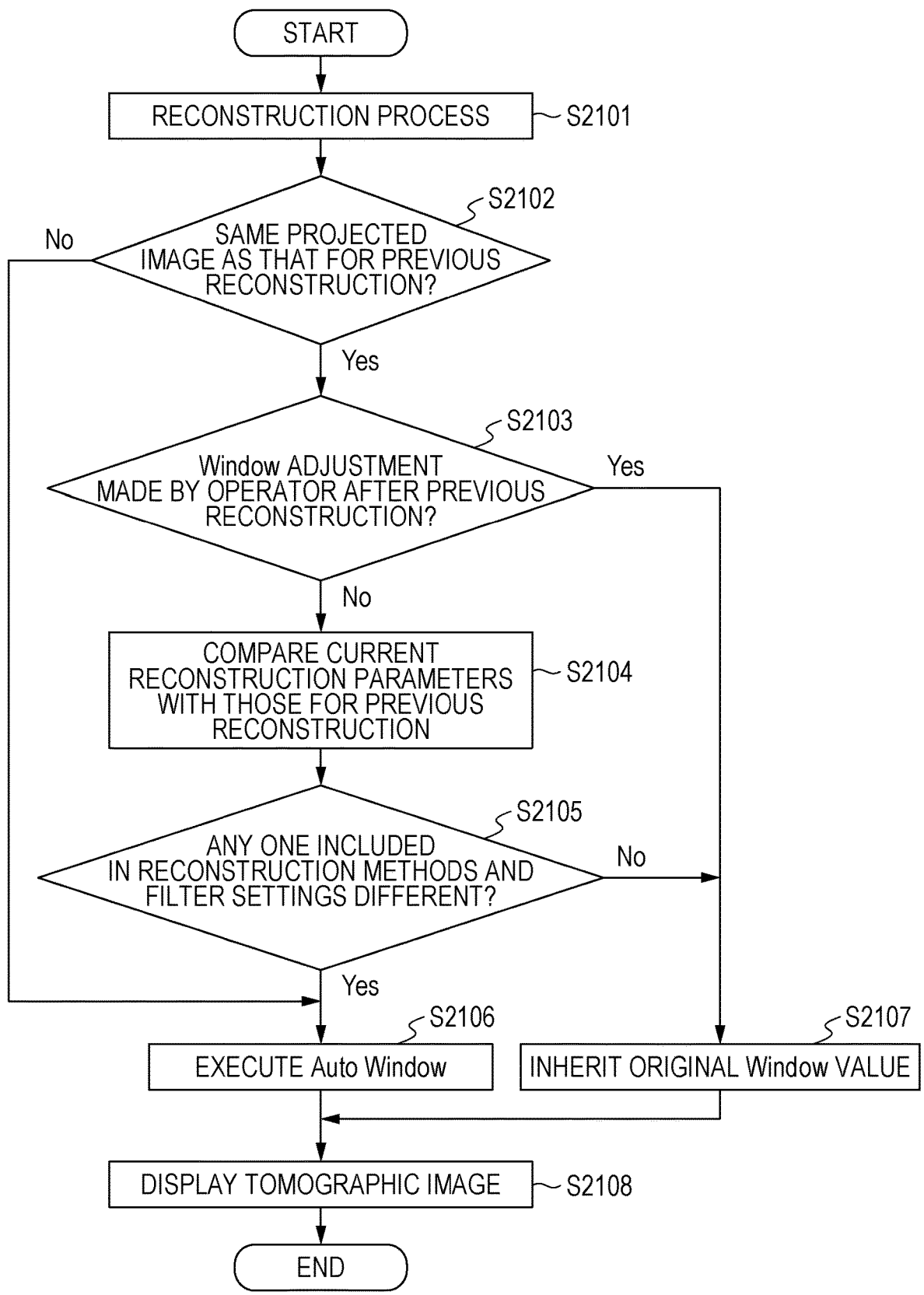
FIG. 21 is a diagram illustrating a process flow related to window processing according to the embodiment of the present invention from an execution of a reconstruction process until a tomosynthesis image is displayed.
Figure 23:
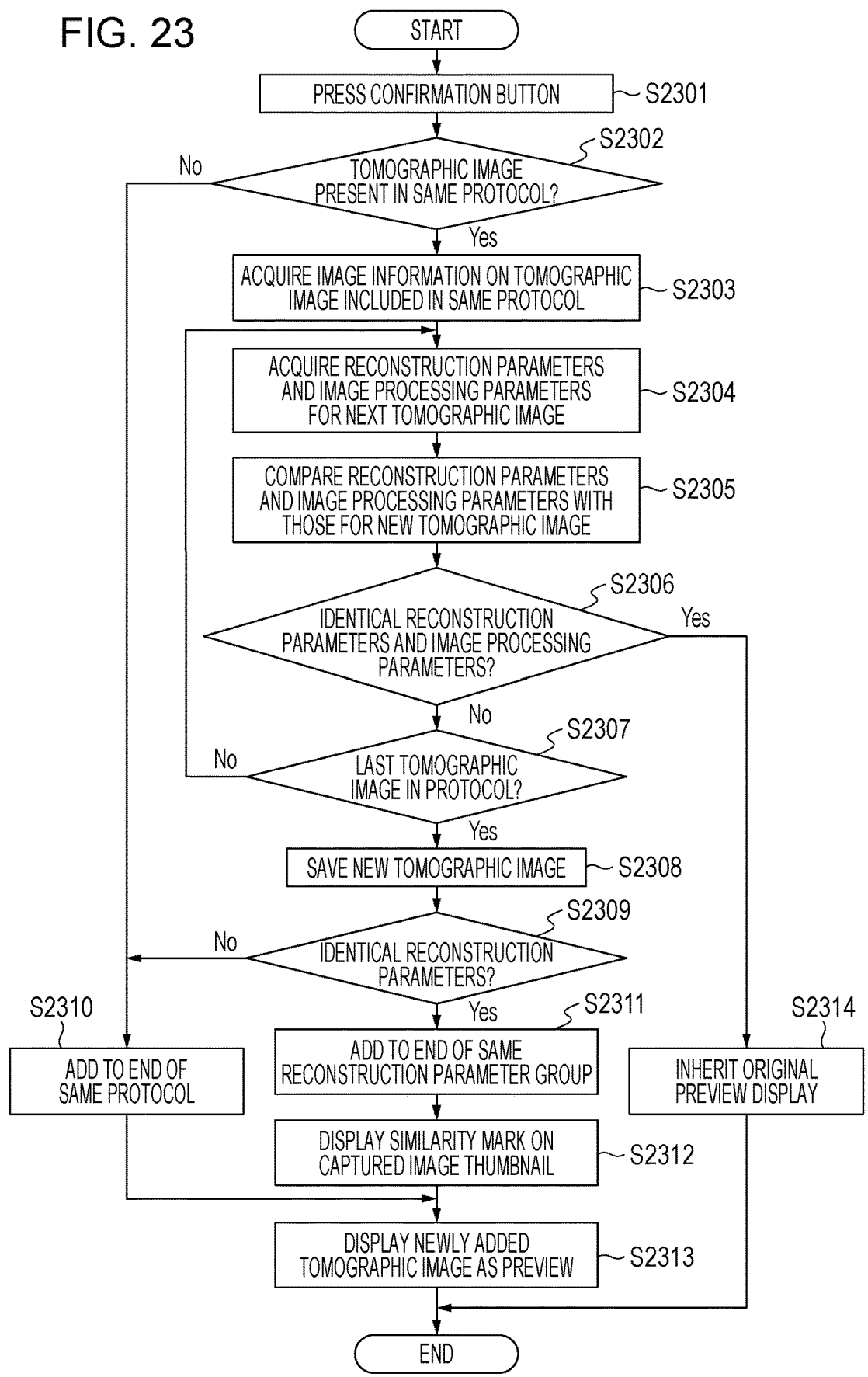
FIG. 23 is a diagram illustrating a process flow according to the embodiment of the present invention from the confirmation of reconstruction until an image is displayed as a preview.
Figure 25:
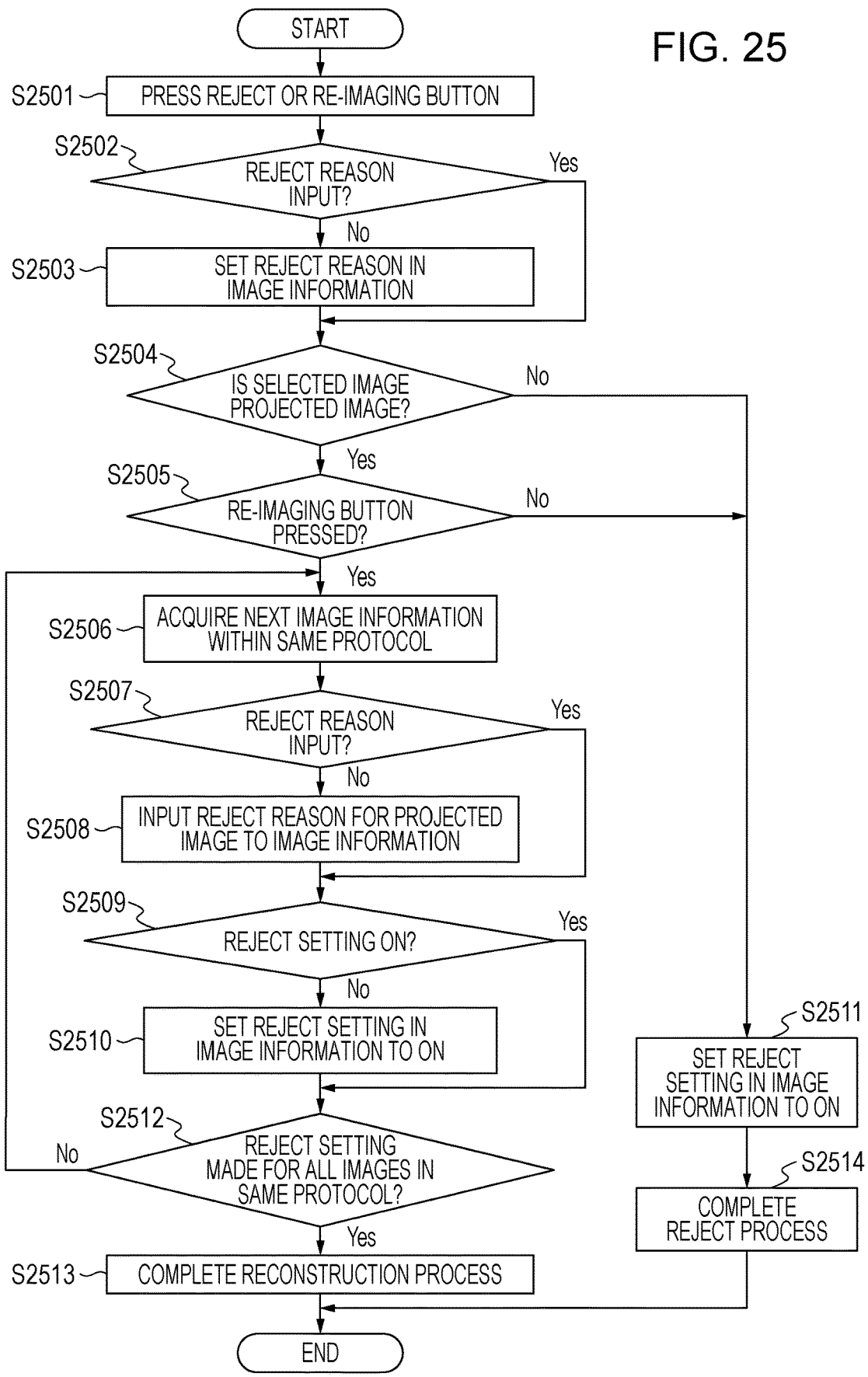
FIG. 25 is a diagram illustrating a process flow according to the embodiment of the present invention from the start of reject and reconstruction processes until a reject setting is performed.

In the embodiment described above, the imaging control device 107 illustrated in FIG. 4 or FIG. 16 is configured to execute the oblique display control illustrated in S1317 and S1318 in FIG. 13, the correction process and a notification thereof illustrated in S1307 and S1315, the valid frame determination illustrated in FIG. 19, the processes illustrated in FIG. 21, FIG. 23, and FIG. 25, and so forth. However, the embodiment is not limited thereto. For example, an image processing device or an image management device, such as the PACS 115 or the viewer 116 illustrated in FIG. 1, may be configured to execute the processes according to the embodiment described above. The processes are executed by the imaging control device, enabling the X-ray imaging system 101 to make detailed studies and providing efficient imaging. Accordingly, repetitions of imaging can be reduced and efficient X-ray imaging can be achieved.

An imaging control device 107 according to a different embodiment of the present invention will be described with reference to FIG. 16. The elements assigned numerals similar to the numerals illustrated in FIG. 4 have configurations and functions similar to those in FIG. 16 unless otherwise stated. The imaging control device 107 according to this embodiment further includes a correspondence correction unit 1601, a condition comparison unit 1602, a valid frame determination unit 1604, and a tone conversion processing execution determination unit 1608. Additionally, the image processing unit 110 includes a reconstruction processing unit 1611, a tone conversion parameter acquisition unit 1612, and a tone conversion processing unit 1613. The image processing unit 110 and the communication circuit 112 are incorporated in the control unit 111. For example, the image processing unit 110 is implemented by the CPU 501 illustrated in FIG. 5. Note that, for example, in the image processing unit 110, only the reconstruction processing unit 1611 may be implemented by a circuit separate from the control unit 111, for example, by a dedicated GPU. Further, the communication circuit 112 is not designed to be connected to the control unit 111, and is a circuit block formed integrally with the control unit 111.

The reconstruction processing unit 1611 of the image processing unit 110 reconstructs a tomosynthesis image on the basis of a plurality of projected images and position information such as an irradiation direction. For reconstruction, various reconstruction conditions, including reconstruction methods such as the FBP and the iterative reconstruction method, filter types such as the Lamp filter, the Shepp & Logan filter, and the Chesler filter, filter settings such as a filter DC and a cutoff frequency, tomographic settings such as a tomographic pitch, the number of tomograms, and a reconstruction range, and a parameter for a noise reduction process, are set. A reconstruction process is performed based on these setting parameters.

The tone conversion parameter acquisition unit 1612 acquires parameters or tone conversion conditions for performing tone conversion processing of a tomosynthesis image. The tone conversion conditions include, for example, a window level and a window width for determining a tone. For example, the tone conversion parameter acquisition unit 1612 analyzes a histogram of tomographic images at the isocenter position of the tomosynthesis image to acquire the parameters of the window level and the window width. In another case, the condition setting unit 4051 generates setting information in accordance with the operation input from the operation unit 108, and the tone conversion conditions are input to the image processing unit 110 through the imaging control unit 405. In this case, the tone conversion parameter acquisition unit 1612 acquires the input tone conversion conditions. The tone conversion parameter acquisition unit 1612 inputs the acquired tone conversion conditions to the tone conversion processing unit 1613.

The tone conversion processing unit 1613 performs tone conversion processing on the tomosynthesis image by using the obtained tone conversion conditions. For example, the tone conversion processing unit 1613 performs tone conversion processing on a two-dimensional tomographic image obtained based on the tomosynthesis image.

As described above, the image processing unit 110 generates a tomosynthesis image in accordance with a plurality of projected images and set process conditions such as reconstruction conditions and tone conversion conditions.

The correspondence correction unit 1601 corrects a correspondence relationship between a set of pieces of position information on the X-ray detector 106 and the X-ray generation unit 102, which is obtained from the X-ray control unit 104 via the communication circuit 112, and a set of projected images obtained from the X-ray detector 106 via the communication circuit. If the projected images and the pieces of position information are not in one-to-one correspondence for the reasons such as a mismatch between the number of projected images and the number of pieces of position information and missed timing due to a device error or depending on the specifications, the correspondence correction unit 1601 performs a process of performing correction by finding an appropriate pair. This allows the generation of a reconstructed image without wasting projected images, and contributes to a reduction in the radiation exposure of the object. The processing result of the correspondence correction unit 1601 is output to the imaging control unit 405, and the display control unit 4070 causes a message corresponding to the processing result to be displayed. The details of the correspondence correction process will be described below with reference to FIG. 17 and FIG. 18.

The valid frame determination unit 1604 determines an invalid image area in accordance with the position information on the X-ray generation unit 102 and the X-ray detector 106 obtained from the X-ray generation apparatus through the communication circuit 112. The invalid image area corresponds to, for example, an area outside the object or an area away from the X-ray generation unit 102 more than from the detection surface of the X-ray detector 106, which is computationally obtained. The display control unit 4070 causes the display unit 109 to display the tomosynthesis image obtained in accordance with the determination result. This enables a tomosynthesis image to be displayed while taking into account an invalid image area. The details of the display process that takes into account an invalid image area will be described below using FIG. 19 and FIG. 20.

The tone conversion processing execution determination unit 1608 determines whether or not to execute tone conversion processing of the tomosynthesis image, in accordance with the settings of the reconstruction conditions or process conditions. In this case, if the condition setting unit 4051 sets reconstruction conditions and tone conversion conditions, the tone conversion processing execution determination unit 1608 compares the conditions before and after the change, and determines whether or not a setting has been made to change the conditions. If a change has been made, the imaging control unit 405 controls whether or not to use the tone conversion conditions after the change for tone conversion processing on a tomosynthesis image reconstructed under the reconstruction conditions after the change. Here, if the reconstruction method has been changed, the tone conversion processing conditions after the change are not used. The tone conversion parameter acquisition unit 1612 analyzes a tomosynthesis image reconstructed using the reconstruction method after the change and acquires tone conversion conditions, and the tone conversion processing unit 1613 performs tone conversion processing.

Accordingly, appropriate image processing in accordance with a change in conditions can be executed. The details of the control as to whether to execute tone conversion processing will be described below with reference to FIG. 21 and FIG. 22.

The condition comparison unit 1602 compares a variety of process conditions set by the condition setting unit 4051, and outputs the comparison result to the imaging control unit 405. The imaging control unit 405 controls the processes performed by the display control unit 4070 and the image processing unit 110 in accordance with the processing result of the condition comparison unit 1602.

The condition comparison unit 1602 contributes to additional display control of a captured image thumbnail 1011 that is an icon indicating a tomosynthesis image displayed on the imaging screen 1001 illustrated in FIG. 10 or the like. The condition comparison unit 1602 compares the process conditions set by the condition setting unit 4051 with the process conditions for the tomosynthesis image already generated by the image processing unit 110. The display control unit 4070 controls whether or not to display a new icon corresponding to the set process conditions, in accordance with the comparison result. This can facilitate comparison of a plurality of tomosynthesis images while suppressing an unnecessary increase in icons. The details of the additional display control of an icon will be described below with reference to FIG. 23 and FIG. 24.

The data described above includes data of a projected image group constituted by a plurality of projected images or data of a tomosynthesis image obtained on the basis of the projected image group. The condition setting unit 4051 sets at least one of the data of the tomosynthesis image or the data of the projected image group as a reject. The reject setting functions as the setting of output conditions. The image output control unit 409 limits the transmission of the data set as a reject to the external device. In response to the setting of the data of the projected image group as a reject, the condition setting unit 4051 sets, as a reject, data of a tomosynthesis image generated based on the projected image group. Accordingly, if it is determined that the projected image group is not appropriate for the user as a diagnostic target, data of a tomosynthesis image obtained based on the inappropriate projected image group is also set as a reject, which can reduce the probability of inappropriate data being output to outside. The details of the reject process will be described below using FIGS. 25 to 28.

Any one or any combination of the correspondence correction process described above, the display process taking into account an invalid image area, the control as to whether to execute tone conversion processing, the additional display control of an icon, and the reject process may be configured to be executable. These processes may also be independently executed without being combined with the oblique display limitation process illustrated in the example described above.

The advantages of the processes according to the foregoing embodiment will be described. Tomosynthesis imaging which enables reconstruction of an arbitrary tomographic image requires involves a plurality of frames to be captured from the object in a single session for capturing projected images. Thus, several seconds are required as an imaging period of time from the start to the end of imaging. This may cause irradiation to be interrupted without the completion of the desired imaging due to a motion of the object or an operational error. In this case, even if reconstruction is successful, a tomosynthesis image will probably not be generated with the desired accuracy. The same applies to the display of an oblique cross section. In interrupted imaging, complete prohibition of reconstruction may cause waste of even images which can be used for reconstruction, leading to increased radiation exposure of the object. In contrast, if a tomosynthesis image is displayed in a normal way through the reconstruction from projected images obtained in the interrupted imaging, it will be difficult to recognize that the tomosynthesis image may have been generated with accuracy different from that for the desired image.

The embodiment described above enables a reconstruction process to be performed as much as possible by effectively using captured images in accordance with the situation even if the imaging has been interrupted. In addition, an available process is distinguishably controlled in accordance with the situation in which interruption of imaging is occurring, leading to less likelihood of false diagnosis by an operator. It is also possible to judge the availability of reconstruction and the availability of the display of an oblique cross section in accordance with the situation in which interruption of imaging is occurring, preventing an increase in the radiation exposure of the object without readily wasting captured images. In addition, an operator is notified of the content of control based on the situation in which interruption of imaging is occurring, so that the operator can recognize the difference between the interruption and the completion of imaging, leading to less likelihood of false diagnosis.

The imaging control unit 405 of the imaging control device 107 having the configuration illustrated in FIG. 16 performs the process of step S609 in FIG. 6 described above, so that the imaging control unit 405 determines, as valid frames, only a region including the object within a tomosynthesis image frame group by using the reconstruction parameters and the position information (FIG. 19). Accordingly, invalid frames are controlled so as not to be stored, preventing an unnecessary frame image from being displayed as a preview and making it possible to save the storage capacity for the storage of images. Upon receipt of the reconstruction completion notification, the examination control unit 406 generates new tomosynthesis image information, and receives the input of the tomosynthesis image, the reconstruction parameters, and the image processing parameters, which are included in the reconstruction completion notification. Thereafter, the examination control unit 406 adds the newly generated tomosynthesis image information to an imaging technique for which reconstruction has been completed within the imaging technique information included in the examination-scheduled-to-be-conducted information. At the same time, the examination control unit 406 transmits the reconstruction completion notification to the display control unit 4070. Upon receipt of the reconstruction completion notification, the display control unit 4070 transmits the reconstruction completion notification to the display unit 109. Upon receipt of the reconstruction completion notification, the display unit 109 makes the progress bar being displayed in the image display portion 1002 invisible. Then, the display unit 109 displays the tomosynthesis image as a preview in the image display portion 1002, and updates a display annotation. On the reconstruction screen 1101, reconstruction is re-performed on the tomosynthesis image by editing the window processing, reproduction process, or reconstruction parameters. In this case, in the present invention, in a case where reconstruction is re-performed, the imaging control unit 405 refers to the content of the edited reconstruction parameters, and determines whether or not the availability of execution of auto-window processing immediately after reconstruction (FIG. 21). Accordingly, auto-window processing is executed only when necessary for the execution of reconstruction, enabling the display of a tomosynthesis image subjected to the optimum window processing always desired by the operator. Thereafter, upon acceptance of a reconstruction confirmation instruction, the operation unit 108 transmits the reconstruction confirmation notification to the input detection unit 4071. Upon receipt of the reconstruction confirmation notification, the input detection unit 4071 transmits the reconstruction confirmation notification to the examination control unit 406. Upon receipt of the reconstruction confirmation notification, the examination control unit 406 saves the tomosynthesis image. In this case, in the present invention, the examination control unit 406 compares the tomosynthesis image for which reconstruction has been confirmed with the tomosynthesis image which are already present in the imaging technique information in terms of the reconstruction parameters and the image processing parameters, and judges whether or not the tomosynthesis image can be saved (FIG. 23). This can prevent a plurality of completely identical tomosynthesis images from being saved. At the same time as this, when tomosynthesis images are displayed in parallel on the imaging screen 1001, the issue of an effect of the arrangement of identical tomosynthesis images on medical interpretation can be addressed.

<Correspondence Correction Process>

Figure 17:
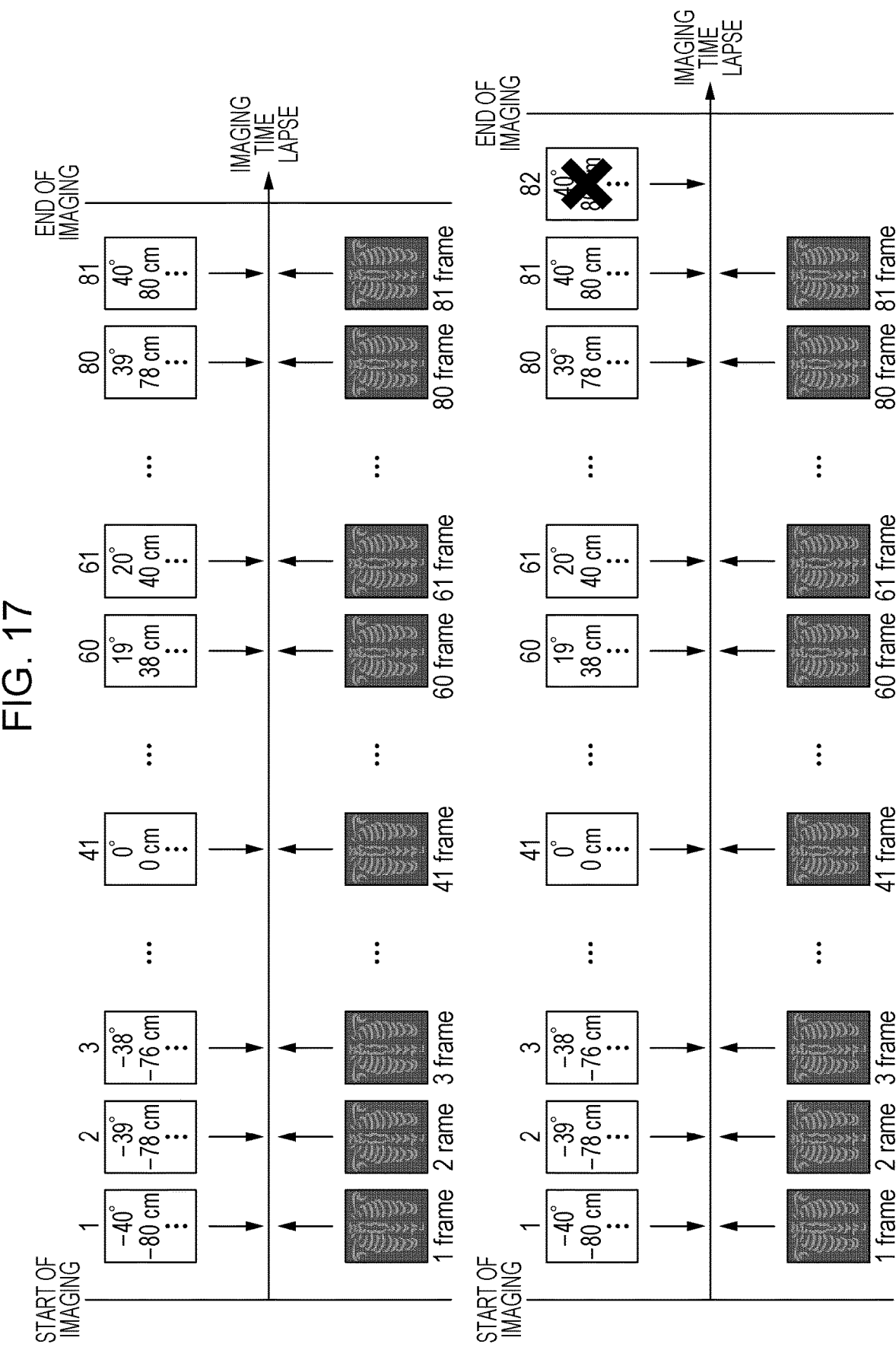
FIG. 17 is a diagram illustrating an example in a case where a discrepancy occurs between the number of projected image frames and the number of pieces of position information.

The details of the correspondence correction process will be described hereinafter with reference to FIG. 17 and FIG. 18.

The process of the correspondence correction unit 1601 will be described with reference to FIG. 17. This process is another embodiment of the correction process in step S1307 in FIG. 13. FIG. 17 illustrates an example in which a discrepancy occurs between the number of projected image frames and the number of pieces of position information. In general, when projected images are captured, as illustrated in FIG. 17, the X-ray control unit 104 and the X-ray detector 106 notify the imaging control device 107 of position information which is synchronized with the reading of image data over a period from the start of imaging to the end of imaging. Thus, no discrepancy occurs between the number of frames of projected images and the number of pieces of position information. However, due to reasons such as an operational control error of the apparatus, as illustrated in FIG. 17, there may be a discrepancy with the number of frames of projected images. FIG. 17 illustrates, by way of example, the case where the number of pieces of position information is larger than expected, and all the patterns of discrepancies between the number of frames of projected images and the number of pieces of position information are included. In this case, there is a problem in that a reconstruction process with a discrepancy between the number of frames of projected images and the number of pieces of position information may cause an error. Thus, as in FIG. 17, if there is a discrepancy between the number of frames of projected images and the notified number of pieces of position information, a correction process for making the number of frames of projected images and the notified number of pieces of position information match each other is performed to make reconstruction available, in which state a reconstruction process is executed. The correction process illustrated here may be the following method. Each of the pieces of image information on the projected image frames and each of the pieces of and position information have recorded therein a time at which the corresponding information was acquired, a projected image frame and a piece of position information having the same recorded time are paired, and the remaining information is discarded. Alternatively, a method may be used in which projected image frames and pieces of position information are sequentially paired one by one from the beginning and the final remaining information is discarded. Alternatively, a method may be used in which projected image frames and pieces of position information are sequentially paired one by one from the end and the final remaining information is discarded. Alternatively, a method may be used in which the position information with an imaging angle of 0° or the position information with an X-ray detector moving distance of 0 is aligned with the center of the projected image frames, the projected image frames and the pieces of position information are sequentially paired one by one toward the beginning and end from the aligned position, and the final remaining information is discarded. Alternatively, a method may be used in which if the number of pieces of position information is smaller than the number of projected image frames, position information corresponding to the remaining projected image frame is calculated from the notified position information group and is added. The correction process described above enables a reconstruction process to be executed with accuracy maintained even if there arises a problem that is not intended by the operator, such as a discrepancy between the number of frames of projected images and the number of pieces of position information.

Figure 18:
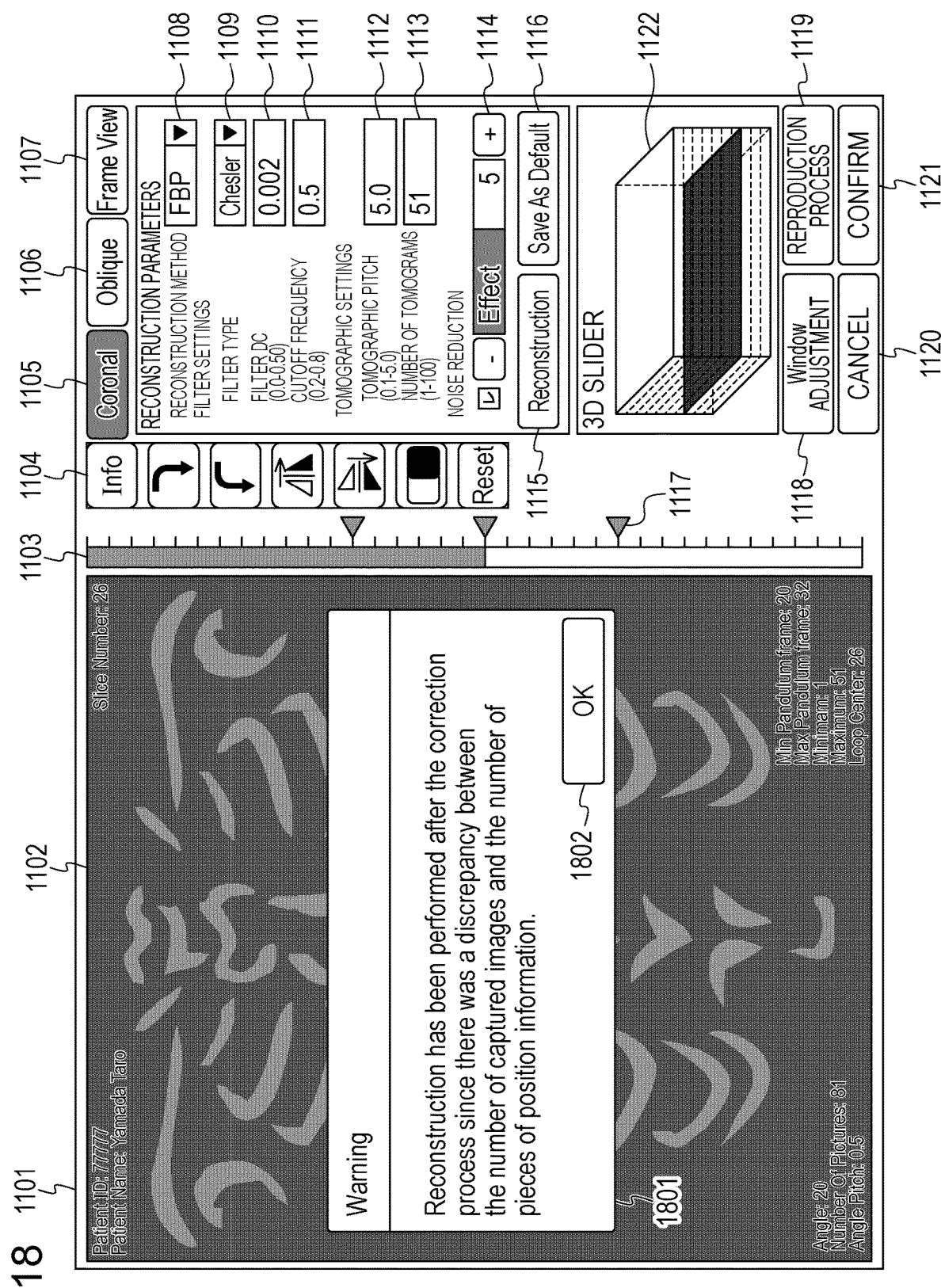
FIG. 18 is a diagram illustrating the reconstruction process screen according to the embodiment of the present invention in a case where a correction process is executed.

Here, an example of a pop-up screen 1801 displayed on the reconstruction screen 1101 when the correction process is carried out in step S1315 in FIG. 13 is illustrated using FIG. 18. The pop-up screen 1801 is displayed on the reconstruction screen 1101. The pop-up screen 1801 shows a message indicating that a correction process has been carried out, and an OK button 1702. When the OK button 1802 is pressed, the pop-up screen 1801 is closed. The pop-up screen 1801 having the configuration described above is displayed.

<Display Process Taking into Account Invalid Image Area>

In the following, the details of a display process taking into account an invalid image area will be described with reference to FIG. 19 and FIG. 20.

FIG. 19 illustrates an example of valid frames in the present invention. As illustrated in FIG. 19, tomosynthesis images in a region where the object is included are referred to as valid frames, and the other tomosynthesis images are referred to as invalid frames. Accordingly, a tomosynthesis image in which the object is not included is controlled so that no invalid frames are displayed, enabling only the valid frames to be displayed as previews. Thus, diagnostic accuracy is improved. In addition, the reproduction process does not involve the need to successively specify ranges only for valid frames and reproduce the valid frames, achieving smooth work flow. Furthermore, control is performed to save only the valid frames, providing efficient storage capacity. In the following, the details of the valid frame determination process will be provided. In the valid frame determination process, position information notified when a projected image is captured is used (FIG. 3). Upon receipt of a reconstruction completion notification from the image processing unit 110, the imaging control unit 405 transmits a valid frame determination request notification to the valid frame determination unit 1604. The valid frame determination request notification includes reconstruction parameters and position information. Upon receipt of the valid frame determination request notification, the valid frame determination unit 1604 carries out a valid frame determination process. The valid frame determination process illustrated here is separated into a lower valid frame determination process for determining a valid frame in the downward direction with respect to the isocenter, and an upper valid frame determination process for determining a valid frame in the upward direction. The lower valid frame determination process may be a method for making frames above the imaging table 105 valid in accordance with the following equation.

The number of lower valid frames $x$=isocenter-to-table-top distance/slice pitch Alternatively, a method for making image frames included in a distance corresponding to a certain threshold value from the isocenter valid may be used. In this case, the threshold value may be fixed or editable. Alternatively, a method for making a number of image frames corresponding to a certain number of slices from the isocenter valid may be used. In this case, the number of slices set as valid frames may be fixed or editable. In contrast, the upper valid frame determination process may be a method for making image frames included in the X-ray-source-to-object distance valid in accordance with the following equation.

The number of lower valid frames $x$=X-ray-source-to-object distance/slice pitch Alternatively, a method for making image frames included in a distance corresponding to a certain threshold value from the isocenter valid may be used. In this case, the threshold value may be fixed or editable. Alternatively, a method for making a number of image frames corresponding to a certain number of slices from the isocenter valid may be used. In this case, the number of slices set as valid frames may be fixed or editable. Alternatively, a method for setting image frames included in the X-ray-source-to-object distance as valid frames may be used. Alternatively, a method for setting image frames included in the same distance as the isocenter-to-table-top distance as valid frames may be used.

When the valid frame determination process described above ends, the valid frame determination unit 1604 transmits a valid frame determination notification to the imaging control unit 405. The valid frame determination notification includes a sequence of valid frame numbers. Upon receipt of the valid frame determination notification, the imaging control unit 405 inputs image information on the tomosynthesis image to the valid frame determination notification, and transmits the valid frame determination notification to the examination control unit 406. Upon receipt of the valid frame determination notification, the examination control unit 406 inputs valid frame information to imaging technique information in the held examination-scheduled-to-be-conducted information. Thereafter, the examination control unit 406 saves only valid frame image data of the tomosynthesis image. Further, the examination control unit 406 transmits a valid frame display notification to an input/output control unit 407. The valid frame display notification includes the image information on the tomosynthesis image, and the sequence of valid frame numbers. Upon receipt of the valid frame display notification, the input/output control unit 407 transmits the valid frame display notification to the display unit 109. Upon receipt of the valid frame display notification, the display unit 109 displays only the valid frames when displaying the target tomosynthesis image as a preview and reproducing and displaying the target tomosynthesis image.

In the example described above, the valid frame determination unit 1604 determines valid frames, but is not limited thereto. In another embodiment, invalid frames are determined. As described above, a range within which the object is not present, for example, a tomographic image at a position away from the object more than from the detection surface of the X-ray detection unit among a plurality of tomographic images, that is, frames located in a region below the table top, is determined as invalid frames. Alternatively, if the isocenter position is specified on the object, a region closer to the X-ray generation unit 102 from the isocenter position than a predetermined distance is designated as an area outside the object, and tomographic images located in the region are determined as invalid frames. By doing so, a result obtained by removing unnecessary image information can be presented to the user. In addition, the display control unit 4070 removes image data determined to be an invalid frame, and causes the result to be displayed on the display unit 109. This makes it easy to check whether appropriate imaging is ongoing, and can provide an image suitable for diagnosis.

Here, an example of the reconstruction screen 1101 showing a reproduction processing portion 2001 displayed in step S609 in FIG. 6 is illustrated using FIG. 20. In FIG. 20, the frame specifying slider 1103, which is an example of a slider display indicating the respective positions of a plurality of tomographic images (slices, frame images), is displayed under the control of the display control unit 4070. The display control unit 4070 causes a first region where the plurality of tomographic images are displayed to be displayed, and also causes the frame specifying slider 1103 for selecting one of the plurality of tomographic images to be displayed along the first region. The slider display is not limited to the frame specifying slider 1103 and also includes the 3D slider 1122. In the example in FIG. 20, the 3D slider 1122 is invisible. The display control unit 4070 may perform control to display the 3D slider 1122.

In the slider display, the display control unit 4070 associates individual positions on the slider display with a plurality of tomographic images, and specifies each position of the slider so that a tomographic image corresponding to the position can be selected. The display control unit 4070 causes the selected tomographic image to be displayed in the image display portion 1102. The tomographic images at positions the most away from the isocenter among a plurality of tomographic images determined by the valid frame determination unit 1604 to be valid are associated with the positions of the upper and lower ends of the slider bar. The display control unit 4070 associates, for example, the tomographic image of the valid frame the closest to the X-ray generation unit 102 with the position of the upper end, and the tomographic image of the valid frame the farthest from the X-ray generation unit 102, for example, the tomographic image in the closest proximity to the surface of the top of the imaging table 105, with the position of the lower end. Doing so allows the display control unit 4070 to display a tomosynthesis image while removing tomographic images that are not valid frames, or an invalid image area, to be displayed, which can help appropriately make a diagnosis.

Here, for example, the condition setting unit 4051 is capable of setting the existence range of the object or the value of the thickness. The set existence range of the object is used as the display range of a tomographic image by the display control unit 4070. In addition, the valid frame determination unit 1604 determines a frame image located within the existence range as a valid frame, and the display control unit 4070 sets the valid frame as a display target. In another example, furthermore, the set existence range of the object is used as the generation range of a tomosynthesis image by the reconstruction processing unit 1611, and a tomosynthesis image is subjected to a reconstruction process within the generation range, enabling the reconstruction process to be performed within an appropriate range, leading to a reduction in processing load. For example, the existence range or generation range described above is two-dimensionally displayed by the frame specifying slider 1103 or is three-dimensionally displayed by the 3D slider 1122, which can appropriately help the operator.

In another exemplary embodiment, it is also possible to determine the existence range or generation range described above in accordance with projected images and position information on the projected images. For example, the imaging control unit 405 determines the existence range of the object on the basis of the pixel values of a reconstructed tomosynthesis image. Alternatively, similar processing can also be performed based on the projected images. Doing so enables a tomographic image to be generated or displayed within an appropriate range without forcing the operator to input object thickness information and so forth.

In the slider display described above, the upper portion of the screen is associated with a tomographic image close to the X-ray generation unit 102 and the lower portion of the screen is associated with a tomographic image away from the X-ray generation unit in order to support the actual imaging system. However, this does not apply when the imaging system is arranged in a different way. For example, in a case where tomosynthesis imaging is performed with the object in a standing position, tomographic images may be arranged in the horizontal direction for association. In this case, for example, the frame specifying slider 1103 may be displayed along a lower or upper side of the image display portion 1102.

In the slider display described above, furthermore, the frame reproduction range setting portion 1117 including a plurality of marks indicating the reproduction range of a frame is assigned by the display control unit 4070. The marks can be arranged at arbitrary positions corresponding to tomographic images in accordance with the operation input from the operation unit 108. The marks include, for example, a first mark indicating the start point of the range, a second mark indicating the end point of the range, and a third mark that is arranged always between the first and second marks. The display control unit 4070 moves the third mark, thereby moving the first mark and the second mark in association with the movement of the third mark with the distance between the third mark and the first mark and the distance between the third mark and the second mark maintained. Accordingly, the reproduction range can be changed.

In addition, the display control unit 4070 causes a plurality of tomographic images to be continuously displayed in sequence within the range defined by the plurality of marks in accordance with an instruction based on the operation input to the reproduction processing portion 2001 serving as a GUI described below with reference to FIG. 22(b). This enables the valid range to be automatically and continuously displayed, and the user is able to concentrate on checking an image without performing an operation. In addition, the reproduction range described above is specified for a valid frame. Accordingly, a valid frame can be selectively reproduced and displayed.

The display control unit 4070 causes the initial position of the third mark to be displayed as a position corresponding to the tomographic image at the isocenter position. This enables the user to understand the isocenter position on the basis of the initial position of the third mark. Note that the display control unit 4070 is also capable of causing the isocenter position to be displayed separately from the third mark. For example, as in the 3D slider 1201 illustrated in FIG. 12, the isocenter position is represented by a cross mark.

When the reproduction process instruction portion 1119 is pressed on the reconstruction screen 1101, the 3D slider 1122 becomes invisible. The reproduction processing portion 2001 is then displayed in the same display area as that of the 3D slider 1122. The reproduction processing portion 2001 is used to perform a reproduction process on a frame image group of a tomosynthesis image being displayed as a preview. The reproduction processing portion 2001 is constituted by a loop reproduction instruction portion 2002, a reciprocal reproduction instruction portion 2003, a range-specified reciprocal reproduction instruction portion 2004, a frame rate editing portion 2005, a reverse reproduction instruction portion 2006, a frame-by-frame backward instruction portion 2007, a reproduction stop instruction portion 2008, a frame-by-frame forward instruction portion 2009, and a reproduction instruction portion 2010. The loop reproduction instruction portion 2002 is a button for selecting "loop reproduction" as a reproduction method. The reciprocal reproduction instruction portion 2003 is a button for selecting, as a reproduction method, "reciprocal reproduction" for reciprocally reproducing the first frame and the last frame among all the frames. The range-specified reciprocal reproduction instruction portion 2004 is a button for selecting "range-specified reciprocal reproduction" for reciprocally reproducing a minimum frame and a maximum frame within a range set by the frame reproduction range setting portion 1117. The frame rate editing portion 2005 is a control for editing the reproduction frame rate. The set frame rate value is displayed near the control. The reverse reproduction instruction portion 2006 is a button for providing an instruction to start "reverse reproduction" for performing reproduction in the direction from the last frame toward the first frame. When the reverse reproduction instruction portion 2006 is pressed, reverse reproduction is executed using the currently selected reproduction method. The frame-by-frame backward instruction portion 2007 is a button for providing an instruction to switch the frame image to be displayed as a preview to the immediately preceding frame image. The display reproduction stop instruction portion 2008 is a button for providing an instruction to stop reproduction. The button is disabled during the stop of reproduction. The frame-by-frame forward instruction portion 2009 is a button for providing an instruction to switch the frame image to be displayed as a preview to the immediately subsequent frame image. The reproduction instruction portion 2010 is a button for providing an instruction to start "reproduction" for performing reproduction in the direction from the first frame toward the last frame. When the reproduction instruction portion 2010 is pressed, reproduction is executed using the currently selected reproduction method. In the case of reverse reproduction and reproduction, only the valid frames are reproduced and displayed. For a tomosynthesis image frame which can be specified by a frame-by-frame forward or frame-by-frame backward operation, similarly, only the valid frames can be specified. The reconstruction screen 1101 showing the reproduction processing portion 2001 having the configuration described above is displayed. The configuration and display form of the reproduction processing portion 2001 in the present invention are not limited thereto.

In the embodiment, both a process for determining a valid or invalid image area from a tomosynthesis image generated in advance and a process for determining a valid or invalid image area in accordance with position information or the like in advance before a tomosynthesis image is generated are also included. In the case of determination in advance before the generation of a tomosynthesis image, first of all, it is convenient to control setting information for setting a generation range. The condition setting unit 4051 sets at least one condition among the generation pitch of a plurality of tomographic images, the number of tomographic images generated, and the generation range of a tomosynthesis image. In this case, in response to one of the conditions being set, the condition setting unit 4051 limits the range over which the other conditions can be set. For example, the generation pitch is set to a certain value. In this case, if too many tomographic images are captured, the imaging range becomes too large. Thus, an upper limit is imposed on the number of captured images as far as a threshold value related to the object thickness is not exceeded. Alternatively, the generation range described above is provided with a cap in advance. In addition, the generation range is controlled so as to be set within a range above the table top. Doing so can reduce the probability that an inappropriate generation range may be set by the operator, and enables an appropriate tomosynthesis image to be generated.

<Control as to Whether to Execute Tone Conversion Processing>

Next, a process flow related to window processing from an execution of a reconstruction process in step S609 in FIG. 6 until a tomosynthesis image is displayed is illustrated using FIG. 21. In the illustrated process, first, the reconstruction processing unit 1611 reconstructs a first tomosynthesis image from the plurality of projected images in accordance with the reconstruction conditions (the previous reconstruction in step S2102). The tone conversion parameter acquisition unit 1612 acquires tone conversion conditions on the basis of the reconstructed tomosynthesis image. In this state, the condition setting unit 4051 is capable of setting reconstruction conditions or tone conversion conditions in accordance with the operation input to the operation unit 108. The settings described above are executed, and process flows when the process conditions described above are changed and not changed are illustrated in steps after step S2101. When the settings of the reconstruction conditions are changed, the reconstruction processing unit 1611 reconstructs a second tomosynthesis image in accordance with the reconstruction conditions after the change. Then, the imaging control unit 4051 controls whether or not to execute, for the second tomosynthesis image, tone conversion processing (auto-window processing) using tone conversion conditions obtained through the analysis process of the tone conversion parameter acquisition unit 1612 in accordance with the second tomosynthesis image.

When the condition setting unit 4051 changes the reconstruction conditions and the tone conversion conditions, the imaging control unit 405 controls whether or not to use the tone conversion conditions after the change for tone conversion processing for a tomosynthesis image reconstructed in accordance with the reconstruction conditions after the change. In a different aspect, the imaging control unit 405 controls whether or not to execute tone conversion processing on a tomosynthesis image, which is reconstructed in accordance with the reconstruction conditions after the change, using the tone conversion conditions obtained through the analysis process of the tone conversion parameter acquisition unit on the basis of the tomosynthesis image.

First, in step S2101, a reconstruction process is carried out. In the present invention, the reconstruction process can be executed not only immediately after the capture of projected images described above but also when the reconstruction process instruction portion 1010 on the imaging screen 1001 is pressed and when the reconstruction process instruction portion 1115 on the reconstruction screen 1101 is pressed. Upon receipt of an instruction for the reconstruction process from the reconstruction process instruction portion 1010 on the imaging screen 1001 or the reconstruction process instruction portion 1115 on the reconstruction screen 1101, the operation unit 108 transmits a reconstruction request notification to the input/output control unit 407. Upon receipt of the reconstruction request notification, the input/output control unit 407 transmits the reconstruction request notification to the examination control unit 406. In this case, if an instruction has been received through the reconstruction process instruction portion 1115 on the reconstruction screen 1101, the input/output control unit 407 receives reconstruction parameters input to the reconstruction screen 1101 being displayed from the display unit 109, and inputs the reconstruction parameters to the reconstruction request notification before transmitting the reconstruction request notification. Upon receipt of the reconstruction request notification, the examination control unit 406 inputs preview-selection image information and image data to the reconstruction request notification, and then transmits the reconstruction request notification to the imaging control unit 405. In this case, regardless of the imaging type of preview-selection image, a projected image of an imaging technique including the preview-selection image is input as image data. This enables a reconstruction process to be started in any case. In addition, the imaging control unit 405 checks whether or not the reconstruction request notification received from the examination control unit 406 includes reconstruction parameters. If no reconstruction parameters are included, the imaging control unit 405 receives the input of default reconstruction parameters in the imaging technique information. The flow from when the imaging control unit 405 transmits a reconstruction request notification to the image processing unit 110 until a reconstruction process is executed is similar to that of step S608 to step S609 in FIG. 6. At the same time of transmitting a reconstruction request notification to the image processing unit 110, the imaging control unit 405 transmits an auto-window execution determination notification request to the tone conversion processing execution determination unit 1608. The auto-window execution determination request notification includes image information on projected images, reconstruction parameters, and window adjustment execution information obtained after the previous reconstruction process. The tone conversion processing execution determination unit 1608 holds image information on projected images and reconstruction parameters for which the previous reconstruction process has been executed.

In step S2102, in accordance with receipt of the auto-window execution determination request notification, the tone conversion processing execution determination unit 1608 compares the projected images subjected to the reconstruction process with the projected images used for the previously executed reconstruction process, and determines whether or not both images are identical. If both images are different, the tone conversion processing execution determination unit 1608 sets the auto-window processing execution availability to "available", and then transmits an auto-window execution determination notification to the imaging control unit 405. The auto-window execution determination notification includes the auto-window processing execution availability.

If both images are identical, in step S2103, the tone conversion processing execution determination unit 1608 checks whether or not the operator has performed window adjustment after the execution of the previous reconstruction process. The tone conversion processing execution determination unit 1608 checks the window adjustment execution information obtained after the previous reconstruction process. If the operator has executed window adjustment, the tone conversion processing execution determination unit 1608 sets the auto-window processing execution availability to "unavailable". Thereafter, the tone conversion processing execution determination unit 1608 transmits the auto-window execution determination notification to the imaging control unit 405.

Here, the imaging control unit 405 controls whether or not to use the tone conversion conditions after the change in accordance with whether or not a tomosynthesis image based on the reconstruction conditions and tone conversion processing conditions before the change has been generated. That is, if no tomosynthesis image based on a projected image group corresponding to the same imaging technique has been generated, auto-window processing based on the analysis process of the tone conversion parameter acquisition unit 1612 is executed. This process implements, for example, automatic control for executing auto-window processing in step S2102 and step S2106 in accordance with the completion of the capture of projected images.

If the tomosynthesis image has been generated, further through the process subsequent to step S2103, in step S2107, tone conversion processing that inherits the previous window values (the tone conversion conditions after the change) is executed on a tomosynthesis image reconstructed under the reconstruction conditions after the change. This enables appropriate control of the generation of a tomosynthesis image.

If the operator has executed window adjustment, the tone conversion processing execution determination unit 1608 performs a process from step S2104 to check the content of the change of the reconstruction conditions. The tone conversion processing execution determination unit 1608 compares the reconstruction parameters used for the execution of the previous reconstruction with the reconstruction parameters included in the auto-window execution determination notification request, in terms of the parameter values of the reconstruction method, the filter type, the filter DC, the cutoff frequency, and the noise reduction process. The reconstruction parameters illustrated here include the respective values of the portions from the reconstruction method selection portion 1108 to the noise reduction process editing portion 1114 on the reconstruction screen 1101.

Then, in step S2105, the tone conversion processing execution determination unit 1608 checks the comparison results for all the acquired parameter values. As a result, if even one parameter differs, the tone conversion processing execution determination unit 1608 sets the auto-window processing execution availability to "available". If the values of all the parameters are identical, the tone conversion processing execution determination unit 1608 sets the auto-window processing execution availability to "unavailable". Thereafter, the tone conversion processing execution determination unit 1608 transmits an auto-window execution determination notification to the imaging control unit 405. Upon receipt of the auto-window execution determination notification, the imaging control unit 405 checks the auto-window processing execution availability. If the auto-window processing execution availability indicates "available", the imaging control unit 405 transmits an auto-window processing request notification to the image processing unit 110. The auto-window processing request notification includes image data and image information on a tomosynthesis image to be subjected to auto-window processing. If the auto-window processing execution availability indicates "unavailable", the imaging control unit 405 transmits a window processing request notification to the image processing unit 110. The window processing request notification includes image data and image information on a tomosynthesis image to be subjected to auto-window processing.

Upon receipt of the auto-window processing request notification, in step S2106, the image processing unit 110 executes auto-window processing on the target tomosynthesis image data. Thereafter, the image processing unit 110 inputs the values of the window level and the window width calculated in the auto-window procedure to the image information, and then transmits a window processing result notification to the imaging control unit 405.

Upon receipt of the window processing request notification, in step S2107, the image processing unit 110 executes window processing on the target tomosynthesis image data using the values of the window level and the window width input to the image information. Thereafter, the image processing unit 110 transmits a window processing result notification to the imaging control unit 405.

Then, in step S2108, the generated tomosynthesis image is displayed. Upon receipt of both the reconstruction completion notification and the window processing notification from the image processing unit 110, the imaging control unit 405 transmits a reconstruction completion notification to the examination control unit 406. Thereafter, the examination control unit 406 adds the newly generated tomosynthesis image information to an imaging technique for which reconstruction has been completed within the imaging technique information included in the examination-scheduled-to-be-conducted information. At the same time, the examination control unit 406 transmits the reconstruction completion notification to the input/output control unit 407. Upon receipt of the reconstruction completion notification, the input/output control unit 407 transmits a reconstruction completion notification to the display unit 109. Upon receipt of the reconstruction completion notification, the display unit 109 makes the progress bar being displayed in the image display portion 1002 invisible. Then, the display unit 109 displays the tomosynthesis image as a preview in the image display portion 1002, and updates a display annotation.

Through the process described above, in the present invention, when a reconstruction process is executed, it is possible to determine the availability of the execution of auto-window processing in accordance with the content of the edited reconstruction parameters. This enables auto-window processing to be executed and a tomosynthesis image to be displayed with the optimum density when a new tomosynthesis image is generated or in the case of a reconstruction process which involves changes in density. In addition, if the operator has performed editing to the desired window values or in the case of an image construction process which does not involve changes in density, the window values are inherited, thereby achieving the advantage of it being possible to display a tomosynthesis image in a state that is always suitable for medical interpretation.

In a different aspect, the tone conversion parameter acquisition unit 1612 acquires a first tone conversion condition, and the condition setting unit 4051 sets a second tone conversion condition different from the first tone conversion condition and also sets a second reconstruction condition different from a first reconstruction condition set in advance. In this situation, the imaging control unit 405 controls which of the first tone conversion condition and the second tone conversion condition to use for tone conversion processing to be performed on a tomosynthesis image reconstructed in accordance with the second reconstruction condition, in accordance with the first reconstruction condition and the second reconstruction condition. By doing so, even if the operator has actively set tone conversion conditions (second tone conversion condition), a process based on a tone conversion condition (first tone conversion condition) different from the tone conversion conditions is performed in accordance with the situation, enabling an appropriate tomosynthesis image to be obtained in accordance with the situation.

In another embodiment, the imaging control unit 405 performs the following process if one of the reconstruction conditions, for example, the reconstruction method, the filter settings, and the noise processing parameter, has been changed. That is, the imaging control unit 405 causes tone conversion processing to be executed in accordance with tone conversion conditions obtained through the analysis process of the tone conversion parameter acquisition unit 1612 from a tomosynthesis image reconstructed in accordance with the reconstruction method after the change. Accordingly, if the reconstruction parameters have been changed, it is judged that it is inappropriate to use the window processing conditions set by the reference to a tomosynthesis image reconstructed under the reconstruction conditions before the change, and auto-window processing is executed.

In another embodiment, the reconstruction method, the filter settings, and the noise processing parameter in the reconstruction conditions are not changed but the reconstruction pitch, the number of reconstructed images, or the reconstruction range has been changed. In this case, the imaging control unit 405 causes the tone conversion processing unit 1613 to execute tone conversion processing in accordance with the tone conversion conditions after the change. Unless the reconstruction method or the like is changed, an obtained image is considered to be substantially similar to an image before the change. Accordingly, tone conversion processing is performed using tone conversion conditions input by the operator actively operating the operation unit 108, enabling a tomosynthesis image to be displayed with the tone desired by the operator. In this case, furthermore, the imaging control unit 405 performs control not to cause the tone conversion parameter acquisition unit 1612 to execute an analysis process for acquiring tone conversion conditions in accordance with the content of the change of the reconstruction conditions, thereby achieving efficient processing.

In another embodiment, after automatic generation control of the first tomosynthesis image described above and the process for generating a second tomosynthesis image, in accordance with the operation input, the imaging control unit 405 causes the reconstruction of a tomosynthesis image based on a plurality of projected images described above to be re-executed in accordance with the operation input. For example, the condition setting unit 4051 changes the setting of process conditions such as reconstruction conditions or tone conversion conditions, as appropriate, to generate a different tomosynthesis image, resulting in a tomosynthesis image more suitable for diagnosis being obtained.

In addition, in a case where a different reconstruction method (second reconstruction method) is set by the condition setting unit 4051 after the automatic control described above, even if the condition setting unit 4051 has set a different tone conversion condition, a tomosynthesis image obtained through the reconstruction re-executed in step S2107 is subjected to tone conversion processing based on the first tone conversion condition.

Here, an example of the reconstruction screen 1101 showing a window adjustment portion 2201 displayed in step S609 in FIG. 6 is illustrated using FIG. 22. When the window adjustment display instruction portion 1118 is pressed on the reconstruction screen 1101, the 3D slider 1122 becomes invisible. Then, the window adjustment display unit 2201 is displayed in the same display area as that of the 3D slider 1122. The window adjustment portion 2201 is a control for adjusting window values for a tomosynthesis image being displayed as a preview. The window adjustment portion 2201 is constituted by a window level editing portion 2202, a window width editing portion 2203, an auto-window processing instruction portion 2204, and a window value reset instruction portion 2205. The window level editing portion 2202 is a control for editing the window level for the tomosynthesis image being displayed as a preview. Changing the value displayed in the edit box or dragging the mouse on the image display portion 1102 applies the editing to the image being displayed as a preview. The window width editing portion 2203 is a control for editing the window width for the tomosynthesis image being displayed as a preview. Changing the value displayed in the edit box or dragging the mouse on the image display portion 1102 applies the editing to the image being displayed as a preview. The auto-window processing instruction portion 2204 is a button for providing an instruction to perform auto-window processing to calculate the optimum values of the window level and the window width for the image data by using the image processing unit 110 and to automatically apply the values to the tomosynthesis image currently being selected as a preview. When the button is pressed, the frame image being displayed as a preview is subjected to an auto-window processing. The window value reset instruction portion 2205 is a button for providing an instruction to perform a window value reset process for returning the values of the window level and the window width to the initial values immediately after reconstruction. The reconstruction screen 1101 showing the window adjustment portion 2201 having the configuration described above is displayed. The configuration and display form of the window adjustment portion 2201 in the present invention are not limited thereto.

In a different aspect, in the exemplary embodiment described above, the imaging control unit 405 automatically performs a reconstruction process and auto-window processing in accordance with the completion of the capture of projected images, and performs control to cause the display unit to display the tomosynthesis image subjected to the auto-window processing. That is, the reconstruction processing unit 1611 starts the reconstruction of a tomosynthesis image in accordance with the capture of projected images under the control of the imaging control unit 405. The tone conversion parameter acquisition unit 1612 starts an analysis process for the tomosynthesis image in accordance with the completion of the reconstruction, and acquires tone conversion conditions. The tone conversion processing unit 1613 executes tone conversion processing in accordance with the completion of the reconstruction and the completion of the analysis process. The automatic control described above can reduce operation input, and enables the imaging apparatus to efficiently obtain a tomosynthesis image. In a case where the image processing unit 110 is to generate slice images from the tomosynthesis image serving as three-dimensional volume data and to perform tone conversion processing, the slice images may be subjected to an analysis process and tone conversion processing in parallel to the sequential generation of the slice images by using the image processing unit 110. In this case, for example, it is effective that a slice image be generated from the isocenter position and the slice image at the isocenter position be analyzed to obtain tone conversion conditions.

The advantages of the processes according to the embodiment described above will be described. In a case where auto-window processing is to be executed automatically, for example, window values edited on purpose may be changed by a user as desired, which would cause an increase in time and labor for an operator to re-edit the window values. Accordingly, in a process according to one embodiment, in the reconstruction and display of a tomosynthesis image, the auto-window execution availability is judged in accordance with the reconstruction parameters used for the previous reconstruction and the content of the editing of the window values, thereby reducing the load imposed on the operator due to the window adjustment. In addition, in the reconstruction and display of a tomosynthesis image, the auto-window execution availability is judged in accordance with the reconstruction parameters used for the previous reconstruction and the content of the editing of the window values. This enables a tomosynthesis image to be displayed with the window values desired by the operator. In addition, the load imposed on an operator involved in window adjustment can be reduced.

<Additional Display Control of Icon>

Next, a process flow from the confirmation of reconstruction in step S609 in FIG. 6 until an image is displayed as a preview is illustrated using FIG. 23. Here, the examination control unit 406 controls, in accordance with set process conditions and the process conditions corresponding to a tomosynthesis image already generated by the image processing unit 110, whether or not to cause the display unit to display a new icon corresponding to the set process conditions. This can reduce the probability of any redundant icon being displayed, and allows a user to easily select a tomosynthesis image suitable for diagnosis.

Additional display control of an icon according to one embodiment will be described. First, in step S2301, upon acceptance of a reconstruction confirmation instruction, the operation unit 108 transmits a reconstruction confirmation notification to the input/output control unit 407. The reconstruction confirmation notification includes image information. Upon receipt of the reconstruction confirmation notification, the input/output control unit 407 transmits the reconstruction confirmation notification to the examination control unit 406.

Then, in step S2302, upon receipt of the reconstruction confirmation notification, the examination control unit 406 checks whether the tomosynthesis image is present in the same tomosynthesis imaging technique. If the tomosynthesis image is not present in the same tomosynthesis imaging technique in step S2302, the examination control unit 406 saves the tomosynthesis image. The condition comparison unit 1602 determines whether or not at least any one of the set process conditions matches the corresponding one of the process conditions corresponding to a tomosynthesis image already generated by the image processing unit 110.

Then, in step S2310, a new captured image thumbnail 1011 is added to the imaging technique display portion 1009 on the imaging screen 1001. The examination control unit 406 transmits a thumbnail image addition notification to the input/output control unit 407. The thumbnail image addition notification includes thumbnail image data, imaging technique information, thumbnail addition position information, and a similar group number. The thumbnail addition position information described here represents a number for judging where a thumbnail is to be added in the imaging technique display portion 1009 in which items are to be added. The similar group number described here is a number that identifies a similar group to which the tomosynthesis image belongs in an imaging technique. In step S2310, the examination control unit 406 inputs the bottommost number in the imaging technique to thumbnail addition position information. Further, the examination control unit 406 inputs a new, unused number in the imaging technique as a similar group number. Upon receipt of the thumbnail image addition notification, the input/output control unit 407 transmits the thumbnail image addition notification to the display unit 109. Upon receipt of the thumbnail image addition notification, the display unit 109 displays an additional thumbnail image at a designated location in accordance with the imaging technique information and the thumbnail addition position information. Thereafter, the display unit 109 transmits a thumbnail image addition completion notification to the input/output control unit 407. The thumbnail image addition completion notification includes image information. Upon receipt of the thumbnail image addition completion notification, the input/output control unit 407 transmits the thumbnail image addition completion notification to the examination control unit 406. Then, in step S2313, the newly added tomosynthesis image is displayed as a preview. Upon receipt of the thumbnail image addition completion notification to the examination control unit 406, a process for displaying the newly added tomosynthesis image as a preview is executed. Then, the process ends. If the tomosynthesis image is present in the same tomosynthesis imaging technique in step S2302, then in step S2303, the examination control unit 406 acquires image information on all the tomosynthesis images present in the same tomosynthesis imaging technique. Then, in step S2304, the examination control unit 406 acquires a piece of image information from the acquired tomosynthesis image information group. Then, in step S2305, the examination control unit 406 compares the acquired tomosynthesis image information with tomosynthesis image information for which reconstruction has been confirmed in terms of all the parameter values included in the reconstruction parameters and the image processing parameters. Then, in step S2306, if both pieces of tomosynthesis image information are identical in terms of all the parameters, the examination control unit 406 does not save a tomographic image for which reconstruction has been confirmed.

Then, in step S2314, the examination control unit 406 inherits the image displayed as a preview before the execution of the reconstruction process, and then the process ends. In the manner described above, if a tomosynthesis image generated under process conditions that are identical to the set process conditions is present, the examination control unit 406 is configured not to execute a tomosynthesis image generation process based on the set process conditions or icon addition control. This can prevent an increase in the number of unnecessary icons.

If both pieces of tomosynthesis image information are different in terms of all the parameters in step S2306, then in step S2307, the examination control unit 406 checks whether comparison has been made for all the tomosynthesis images. If there is any tomosynthesis image for which no comparison process has been made in step S2307, the process returns to step S2304 and the processes up to step S2307 are repeatedly performed. If a comparison process has been performed for all the tomosynthesis images in step S2307, the examination control unit 406 judges that a tomosynthesis image for which reconstruction has been confirmed is not present in the imaging technique. Then, in step S2308, the examination control unit 406 saves the tomosynthesis image for which reconstruction has been confirmed.

Then, in step S2309, the examination control unit 406 checks whether a tomosynthesis image having the same image processing parameter is present in the same imaging technique as that of the saved tomosynthesis image. If a tomosynthesis image having the same image processing parameter is not present in step S2309, the examination control unit 406 executes the process after step S2310 described above. If a tomosynthesis image having the same image processing parameter is present in step S2309, the examination control unit 406 acquires the similar group number and thumbnail addition position information of the tomosynthesis image at the bottommost position among a tomosynthesis image information group having the same image processing parameter.

Then, in step S2311, the examination control unit 406 adds a new captured image thumbnail 1011 to the imaging technique display portion 1009 on the imaging screen 1001. The examination control unit 406 transmits a thumbnail image addition notification to the input/output control unit 407. In step S2311, the examination control unit 406 inputs the respective values acquired in step S2309 to the thumbnail addition position information and the similar group number. Upon receipt of the thumbnail image addition notification, the input/output control unit 407 transmits the thumbnail image addition notification to the display unit 109. Upon receipt of the thumbnail image addition notification, the display unit 109 additionally displays the captured image thumbnail 1011 at a designated location in accordance with the imaging technique information and the thumbnail addition position information. The display unit 109 further displays in the newly added captured image thumbnail 1011 a similarity mark corresponding to the similar group number. Thereafter, the display unit 109 transmits a thumbnail image addition completion notification to the input/output control unit 407. The thumbnail image addition completion notification includes image information. Upon receipt of the thumbnail image addition completion notification, the input/output control unit 407 transmits the thumbnail image addition completion notification to the examination control unit 406. Then, in step S2313, the newly added tomosynthesis image is displayed as a preview. Upon receipt of the thumbnail image addition completion notification to the examination control unit 406, a process for displaying the newly added tomosynthesis image as a preview is executed. Then, the process ends.

In the process described above, if reconstruction conditions different from the reconstruction conditions corresponding to a tomosynthesis image already generated by the image processing unit 110 have been set, the display control unit 4070 causes the display unit to display a new icon corresponding to the set reconstruction conditions (S2310). Specifically, the display control unit 4070 causes the captured image thumbnail 1011 that is an icon corresponding to the new reconstruction conditions to be added to a display area of the imaging technique display portion 1009. The captured image thumbnail 1011 is selectable in accordance with the operation input of the operation unit 108, and, in accordance with selection, the display control unit 4070 causes a tomosynthesis image corresponding to the captured image thumbnail 1011 to be displayed. In the manner described above, the generation of a new icon allows a user to easily compare a plurality of tomosynthesis images.

This is not to be taken in a limiting sense. In another exemplary embodiment, a situation is considered in which the condition setting unit 4051 sets image processing conditions such as reconstruction conditions and tone conversion conditions of a tomosynthesis image in accordance with a confirmation button 1211 being pressed in step S2301. In this situation, the following process is performed if the same reconstruction conditions as the reconstruction conditions corresponding to a tomosynthesis image already generated by the image processing unit 110 have been generated and if different image processing conditions have been set. In this case, the display control unit 4070 causes the display unit to display a new icon corresponding to the set process conditions. This enables a user to easily compare a plurality of pieces of tomosynthesis image data having different image processing conditions by using single-view display in FIG. 24(a) or multi-view display in FIG. 24(b). Accordingly, more appropriate image processing conditions can be specified.

In this case, furthermore, that is, in a case where the same reconstruction conditions as the reconstruction conditions corresponding to an already generated tomosynthesis image and different image processing conditions have been set, an image processing unit 110 according to one exemplary embodiment is configured to generate a new tomosynthesis image. Specifically, a plurality of tomosynthesis images having different image processing conditions and having the same reconstruction conditions are saved in memory regions reserved at different positions on a memory. Doing so can increase the speed of the display process of a tomosynthesis image, and can facilitate easier comparison.

In another exemplary embodiment, in a case where the same reconstruction conditions as the reconstruction conditions corresponding to an already generated tomosynthesis image and different image processing conditions have been set, the following process is executed. That is, the examination control unit 406 is configured to save the tomosynthesis image and the plurality of image processing conditions in the examination information storage unit 403 in association with each other without generating a new tomosynthesis image. The saved tomosynthesis image may be an image that has been processed under one image processing condition among a plurality of image processing conditions. The use of an image that has not been processed under any image processing condition may result in the later image processing being simple. In accordance with the user selecting a captured image thumbnail 1011, the image processing unit 110 performs image processing on the saved tomosynthesis image in accordance with the image processing conditions corresponding to the thumbnail 1011 selected for the tomosynthesis image. The tomosynthesis image subjected to the image processing is displayed in the image display portion 1102 or the like by the display control unit 4070. Alternatively, as in the exemplary embodiment described above, each of a plurality of captured image thumbnails 1011 corresponding to tomosynthesis images is constituted by an image subjected to image processing under the corresponding image processing conditions, enabling images to be compared by using the captured image thumbnails 1011.

Image processing conditions for a tomosynthesis image corresponding to each of the thumbnail images 1011 described above can be optionally changed by the condition setting unit 4051 in accordance with the operation input of the operation unit 108. In addition, an operation input corresponding to an instruction for returning the changed image processing conditions to the image processing conditions before the change is defined, and the input detection unit 4071 detects this input, thus making it possible to easily return the changed image processing to the original one. The operation input corresponding to an instruction for returning to the image processing conditions before the change may be, for example, an input for selecting a button on the screen, or may be an input for pressing any button on the keyboard.

Figure 24:
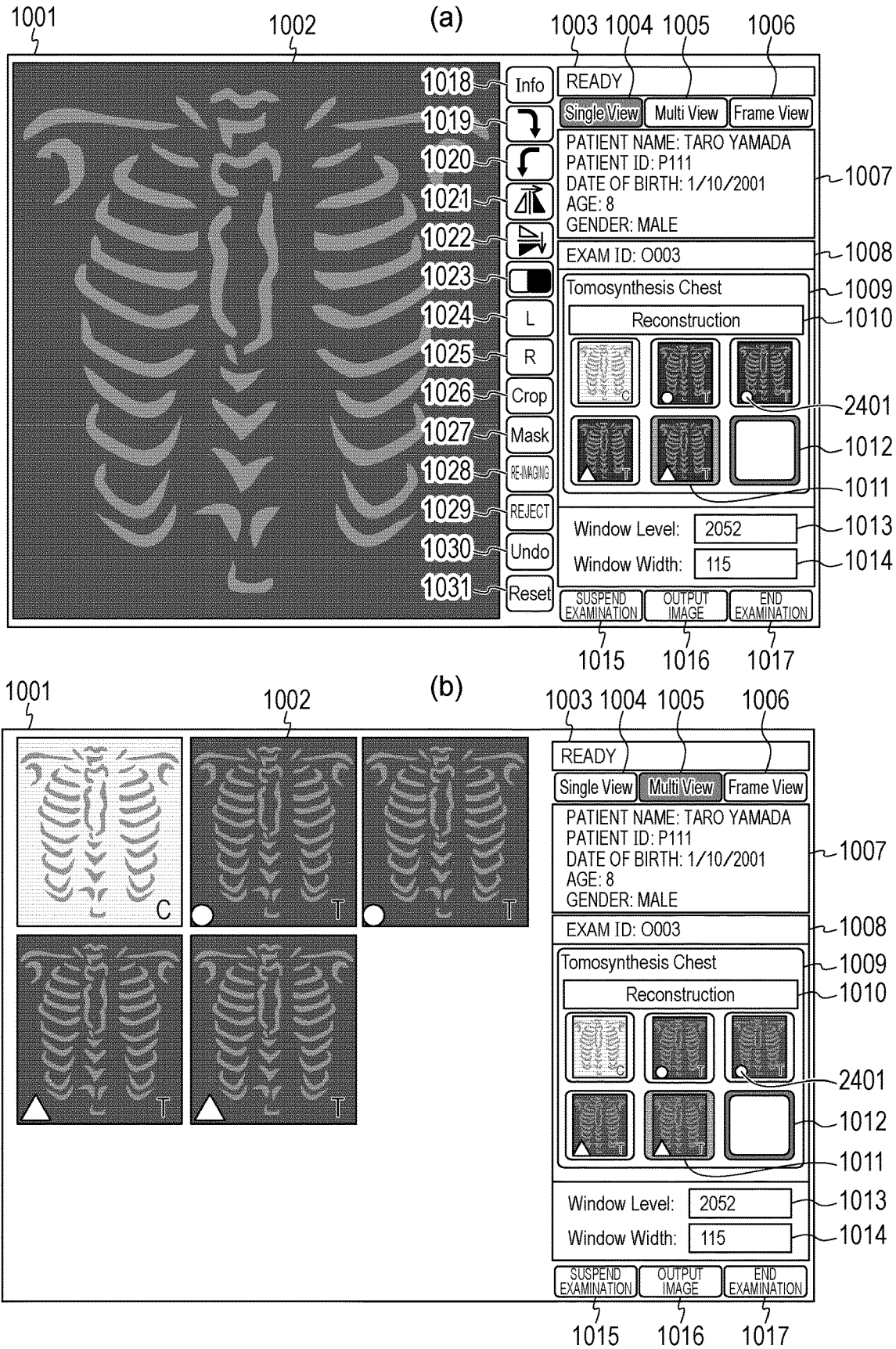
FIG. 24 includes diagrams illustrating a single-view display screen and a multi-view display screen on the imaging screen according to the embodiment of the present invention.

Here, an example of the single-view display and multi-view display of the imaging screen 1001 when the tomosynthesis image displayed in step S2312 and step S2313 in FIG. 23 is selected as a preview is illustrated using FIG. 24. Captured image thumbnails 1011 respectively corresponding to projected images and a tomosynthesis image for which an addition instruction has been given are displayed in the imaging technique display portion 1009 for the tomosynthesis imaging technique. Further, each of the captured image thumbnails 1011 of images obtained by tomosynthesis imaging has displayed thereon a similarity mark 2401. The form of the similarity mark is not limited so long as each group of similar tomosynthesis images is distinguishable from the other groups. While the single-view instruction portion 1004 is selected, the image display portion 1002 provides a single-view display illustrated in FIG. 24(a). While the multi-view instruction portion 1005 is selected, the image display portion 1002 provides a multi-view display illustrated in FIG. 24(b). In the multi-view display, X-ray images or tomosynthesis images corresponding to all the captured image thumbnails 1011 included in the examination being conducted are displayed in parallel in the image display portion 1002. Each of the images displayed in parallel has displayed thereon an imaging type mark, a similarity mark 2401, and a reject mark 2701. As in the present invention, parallel display of images in each similar group enables the operator to easily compare and refer to a plurality of tomosynthesis images, making an improvement in diagnostic accuracy feasible.

As in FIG. 24(a) and FIG. 24(b) described above, the display control unit 4070 assigns an identical mark to a plurality of icons corresponding to the same or similar reconstruction conditions for the captured image thumbnails 1011 or tomosynthesis images in the multi-view display. This can facilitate the identification of tomosynthesis images corresponding to the same reconstruction conditions.

It is assumed here that the display control unit 4070 assigns an identical mark to icons for images not only under the same reconstruction conditions but also under reconstruction conditions for which only some of the parameters are changed. For example, if the reconstruction method and the like are the same and only the reconstruction pitch, the number of tomographic images, or the generation range of a tomosynthesis image is changed or the noise reduction parameter is changed by only a small amount, the examination control unit 406 determines that the reconstruction conditions are similar.

Additionally, the display control unit 4070 may take a variety of forms of display by group. For example, tomosynthesis images included in the same or similar reconstruction conditions are displayed side by side in a row. Alternatively, tomosynthesis images included in the same or similar reconstruction conditions are surrounded by a frame. Such display of a plurality of icons grouped by each of the reconstruction conditions facilitates comparison between reconstruction conditions or comparison of image processing conditions under the same reconstruction conditions.

In another example, furthermore, the grouping described above can be selectively performed based on a variety of kinds of information. For example, the display control unit 4070 performs the following operation. In response to any one of the reconstruction conditions and the image processing conditions being selected in accordance with the operation input to the operation unit 108, the display control unit 4070 performs grouping by the selected one condition, and provides display in the above-described form indicating grouping.

In another embodiment, furthermore, the condition setting unit 4051 is capable of performing a setting of a reject for each group for which the reconstruction conditions or image processing conditions described above are identical. Selecting such a group on the imaging screen 1001 and pressing the reject button 1029 allow tomosynthesis images included in the group to be collectively set as rejects, and facilitate the operation.

As in FIG. 24(*a*) described above, a GUI (1013, 1014) for performing window adjustment for image processing may be displayed on the imaging screen 1001, but is not limited thereto. That is, the display control unit 4070 is configured to display window adjustment only on the reconstruction screen 1101 so that image processing conditions are adjusted through the reconstruction screen 1101, which is displayed so as to be switchable with the imaging screen 1001. The display control unit 4070 does not provide the display on the imaging screen 1001. Furthermore, the examination control unit 406 is capable of performing a display setting to set whether or not it is possible to make a change to the image processing conditions for a tomosynthesis image generated under the set image processing conditions through the first screen on the imaging screen 1001 in accordance with the operation input of the operation unit. This can make the image processing executable as appropriate in accordance with the situation.

Here, consideration is further given of a case where the examination control unit 406 performs a setting so that a change in image processing is not available on the imaging screen 1001. If the same reconstruction conditions as the reconstruction conditions corresponding to a tomosynthesis image already generated by the image processing unit 110 and different image processing conditions are set, the display control unit 4070 causes the display unit to display a new icon corresponding to the set process conditions. In this case, image processing is executed through the reconstruction screen 1101. Accordingly, a new captured image thumbnail 1011 is displayed, enabling tomosynthesis images to be compared by different image processing conditions.

In addition to this, for example, in a case where the examination control unit 406 has performed a setting so that a change in image processing is available on the imaging screen 1001, if the same reconstruction conditions as the reconstruction conditions corresponding to a tomosynthesis image already generated by the image processing unit 110 and different image processing conditions are set, the following process is executed. That is, the display control unit 4070 does not cause the display unit to display a new icon corresponding to the set process conditions. This implies that, if a change in image processing is available on the imaging screen 1001, no new captured image thumbnail 1011 is generated. In this case, the image processing conditions are adjusted by using the GUI displayed on the imaging screen 1001, such as the window level editing portion 1013 and the window width editing portion 1014. This provides the advantage of reducing the number of captured image thumbnails 1011 and facilitating comparison.

In another embodiment, the examination control unit 406 controls whether or not the image processing unit 110 generates a new tomosynthesis image in accordance with information on the slice pitch included in the set process conditions. For example, consideration is given to the case where the set process conditions include a first reconstruction method, a first slice pitch value, and a first number of slices. In this case, furthermore, a tomosynthesis image corresponding to process conditions including the first reconstruction method, the first slice pitch value, and a second number of slices larger than the first number of slices has already been generated. In this case, the following process is executed. That is, the examination control unit 406 does not generate a tomosynthesis image based on the set process conditions. In the manner described above, if a setting is made to obtain a tomosynthesis image having the same reconstruction method, the same slice pitch, and a small number of slices, a tomosynthesis image including the tomosynthesis image described above as a subset has already been generated. Thus, a process for generating a new tomosynthesis image is not performed or no captured image thumbnail is added to the imaging screen 1001. This can reduce the generation of an unnecessary tomosynthesis image, and can also facilitate comparison between tomosynthesis images.

In the example described above, a process for comparing a plurality of tomosynthesis images generated from one projected image group has been described, but is not limited thereto. For example, for the comparison of a plurality of tomosynthesis images generated from a plurality of projected image groups, processes such as icon addition control and display by group may be executed.

The advantages of the above-described processes according to the embodiment will be described. In a case where the number of slices and the slice pitch are specified for the reconstruction of a tomosynthesis image, the target is mainly a microsclere in the orthopedic region or a lesion region in the body, and it is generally difficult to check the thickness of the region of interest. For this reason, it is difficult to decide on the accurate slice pitch and the accurate number of slices. Consequently, a sufficient number of slices are specified to ensure that a tomosynthesis image is reconstructed so that the region of interest is included in a frame group of the tomosynthesis image. In this case, it is probable that the reconstructed tomosynthesis image includes an image not including information on the region of interest. Such an image frame not including the region of interest is displayed side by side with an image frame including the region of interest, which may affect the accuracy of medical interpretation. In addition, an unnecessary image frame is also saved, causing a problem in that an amount of the storage capacity is uselessly consumed. Meanwhile, in a case where an operator selects and saves only a necessary frame of a tomosynthesis image from among frames of reconstructed tomosynthesis images, it is necessary to check all the reconstructed tomosynthesis images on a frame-by-frame basis. According to one of the embodiments described above, a tomosynthesis image not including information on the region of interest among the reconstructed tomosynthesis images is not saved, enabling only a necessary frame image to be displayed. This can improve diagnostic accuracy and provide efficient use of the storage capacity. In addition, when tomosynthesis images are reconstructed, a tomosynthesis image frame not including information on the region of interest is automatically identified and controlled, thereby reducing the load imposed on the operator. Furthermore, an unnecessary frame not including the region of interest is selected from among reconstructed tomosynthesis image frames without requiring any operation performed by the operator, enabling efficient use of the storage capacity and enabling a reduction in the load imposed on the operator.

The advantages of the processes according to the embodiment described above will be described. In a case where a plurality of reconstruction processes are performed from the same projected image, storage of all the reconstructed tomosynthesis images requires a large storage region. Alternatively, in the case of the same reconstruction parameters or image processing parameters as those of an already reconstructed tomosynthesis image, the same image may occupy a plurality of display areas when saved and displayed in parallel. This may affect the accuracy of image-based diagnosis or the efficiency of medical interpretation. In addition, recording of images in the order in which the images were reconstructed may hinder comparison because tomosynthesis images reconstructed under the same conditions may not be displayed in adjacent locations depending on the order of reconstruction.

In the embodiment described above, the registration of tomosynthesis images having different reconstruction parameters or image processing parameters among the reconstructed tomosynthesis images can improve the accuracy of image-based diagnosis and provide efficient use of the storage capacity. In addition, in the registration of tomosynthesis images, tomosynthesis images having the same reconstruction parameters are added in a consecutive order, thereby facilitating comparison and display. Furthermore, only tomosynthesis images having different reconstruction parameters or image processing parameters are displayed with similar images adjacent, thereby facilitating image-based diagnosis. Moreover, storage of only one set of tomosynthesis images having the same reconstruction parameters or image processing parameters can provide efficient use of the storage capacity.

<Reject Process>

Next, a process flow from when the start of reject and reconstruction processes in step S610 in FIG. 6 until a reject setting is performed is illustrated using FIG. 25.

In step S2501, a reject or re-imaging button is pressed. When a reject instruction is given, the operation unit 108 transmits a reject notification to the input/output control unit 407. When a re-imaging instruction is given, the operation unit 108 transmits a re-imaging notification to the input/output control unit 407. The reject notification and the re-imaging notification include selected image information. Upon receipt of the reject notification, the input/output control unit 407 transmits the reject notification to the examination control unit 406. When a re-imaging instruction is given, the input/output control unit 407 transmits a re-imaging notification to the examination control unit 406.

In step S2502, upon receipt of the reject notification or the re-imaging notification, the examination control unit 406 acquires selected image information from the imaging technique information included in the examination-scheduled-to-be-conducted information, and determines whether or not a reject reason has been input.

If no reject reason has been input, in step S2503, the examination control unit 406 sets a reject reason in accordance with the operation input from the operation unit 108. The examination control unit 406 transmits a reject reason input screen transition notification to the input/output control unit 407. Upon receipt of the reject reason input screen transition notification, the input/output control unit 407 transmits the reject reason input screen transition notification to the display unit 109. Upon receipt of the reject reason input screen transition notification, the display unit 109 displays a reject reason input screen. Thereafter, upon receipt of a reject reason confirmation instruction in response to, for example, a confirmation button 2605 being pressed, the operation unit 108 transmits a reject reason input notification to the input/output control unit 407. The reject reason input notification includes image information intended to be a reject and a confirmed reject reason. Upon receipt of the reject reason input notification, the input/output control unit 407 transmits the reject reason input notification to the examination control unit 406. At the same time, the input/output control unit 407 transmits a reject reason input completion notification to the display unit 109. Upon receipt of the reject reason input completion notification, the display unit 109 closes the reject reason input screen. Information on the reject reason is output to the condition setting unit 4051.

Upon receipt of a reject reason cancellation instruction, the operation unit 108 transmits a reject reason cancellation notification to the input/output control unit 407. Upon receipt of the reject reason cancellation notification, the input/output control unit 407 transmits the reject reason cancellation notification to the examination control unit 406. At the same time, the input/output control unit 407 transmits a reject reason input completion notification to the display unit 109. Upon receipt of the reject reason input completion notification, the display unit 109 closes the reject reason input screen. If no reject reason is input, the condition setting unit 4051 may perform control so as not to perform a reject setting. This enables the management of a reject with an explicit statement of grounds therefor. The reject reason may not necessarily be input, and the condition setting unit 4051 may be able to set a reject for data without requiring a reason for the reject.

In step S2504, the examination control unit 406 checks the imaging type of the image intended to be a reject. The term imaging type, as used herein, refers to either data of a projected image group or data of a tomosynthesis image. Data intended to be a reject is determined by using the captured image thumbnail 1011 selected on the imaging screen 1001 through an operation input when either the re-imaging button 1028 or the reject button 1029 is pressed.

If the data intended to be a reject indicates an image other than a projected image, for example, a tomosynthesis image, in step S2504, then in step S2511, the condition setting unit 4051 sets the reject setting in the image information on the target image to ON. For example, upon receipt of the reject reason input notification, the condition setting unit 4051 acquires image information intended to be the reject from the imaging technique information included in the examination-scheduled-to-be-conducted information, and saves the data in the examination information storage unit 403 in association with a flag indicating a reject and information on the reject reason. The flag takes the value 1 when indicating a reject, or the value 0 when indicating not a reject. Accordingly, the data is set as a reject.

Thus, in step S2514, the reject process is completed, and then the process ends.

If the imaging type indicates a projected image in step S2504, then in step S2505, the examination control unit 406 checks whether the instructed process indicates a reject instruction (first instruction) or a re-imaging instruction (second instruction).

If a reject instruction is given in step S2505, then in step S2511, the examination control unit 406 sets the reject setting in the image information on the target image to ON.

Thus, in step S2514, the reject process is completed, and then the process ends.

If a re-imaging instruction is given in step S2505, the examination control unit 406 acquires all the pieces of image information included in imaging technique information including the target projected image from the held examination-scheduled-to-be-conducted information.

Then, in step S2506, the examination control unit 406 acquires a piece of image information from the acquired pieces of image information.

Then, in step S2507, the examination control unit 406 checks whether or not the reject reason in the acquired image information has been input. If the reject reason has not been input, the process proceeds to step S2508 and the examination control unit 406 inputs the reject reason for the target projected image to the reject reason in the acquired image information. The details of this process are similar to those of step S2503 described above.

Then, in step S2509, the examination control unit 406 checks the reject setting in the acquired image information.

If the reject setting is OFF, in step S2510, the condition setting unit 4051 sets the reject setting in the acquired image information to ON.

In step S2511, the examination control unit 406 checks whether the reject setting is ON for all the pieces of image information. If there is any image information in which the reject setting is OFF, the process returns to step S2506 and the processes up to step S2512 are repeatedly performed.

If the reject setting has been made for all the pieces of image information, in step S2513, the condition setting unit 4051 newly generates imaging information corresponding to the projected image, and sets the imaging information in the examination information as new imaging information. The display control unit 4070 causes the display unit to display the new imaging information. Thus, the re-imaging process is completed, and then the process ends.

Through the process steps described above, if a re-imaging instruction is given for a projected image on which a tomosynthesis image is based, projected image and tomosynthesis images obtained based on the projected images are synchronously subjected to reject setting and reject reason input. This can reduce a time-consuming operation of performing a reject process on the images one by one. In addition, if a reject reason has already been input through the execution of another reject process, a higher priority is placed on the previously input reject reason, thereby addressing a problem that a necessary reject reason may be overwritten due to the re-imaging process. On the other hand, a reject process is performed only on a selected image, which can support a use case in which a plurality of tomosynthesis images are generated and images other than necessary images are handled as rejects. In FIG. 25, if an instruction for performing a reject process on a projected image is given, only a projected image is subjected to a reject process. However, if an instruction for performing a reject process on a projected image is given in a way similar to that for a re-imaging process, the demand in which other images are also handled as rejects accordingly could presumably be expected. Such a demand can be easily met by, in the present invention, omitting the process in step S2505 for judging whether or not an instruction for performing a re-imaging process has been given.

In a process according to another embodiment, even if the reject button 1029 is pressed instead of the re-imaging button 1028, the following process is executed. That is, in response to data of a projected image group being set as a reject, the condition setting unit 4051 sets, as a reject, the data of a tomosynthesis image generated based on the projected image group. Accordingly, if it is determined that a projected image is inappropriate as a diagnostic image, regardless of whether or not a re-imaging setting is performed, a tomosynthesis image corresponding to the inappropriate projected image group is determined to be inappropriate, and is set as a reject. This process can reduce the problem that an inappropriate tomosynthesis image is output to outside and is used for diagnosis.

In contrast, even if the data of the tomosynthesis image is set as a reject while the data of the projected image group is not set as a reject, the condition setting unit 4051 does not set the data of the projected image group as a reject. Tomosynthesis images for which diagnostic use is determined to be inappropriate in accordance with the reconstruction conditions and other process conditions can be individually set as rejects, which can mitigate the problem in that an inappropriate tomosynthesis image is used for diagnosis.

Figure 26:
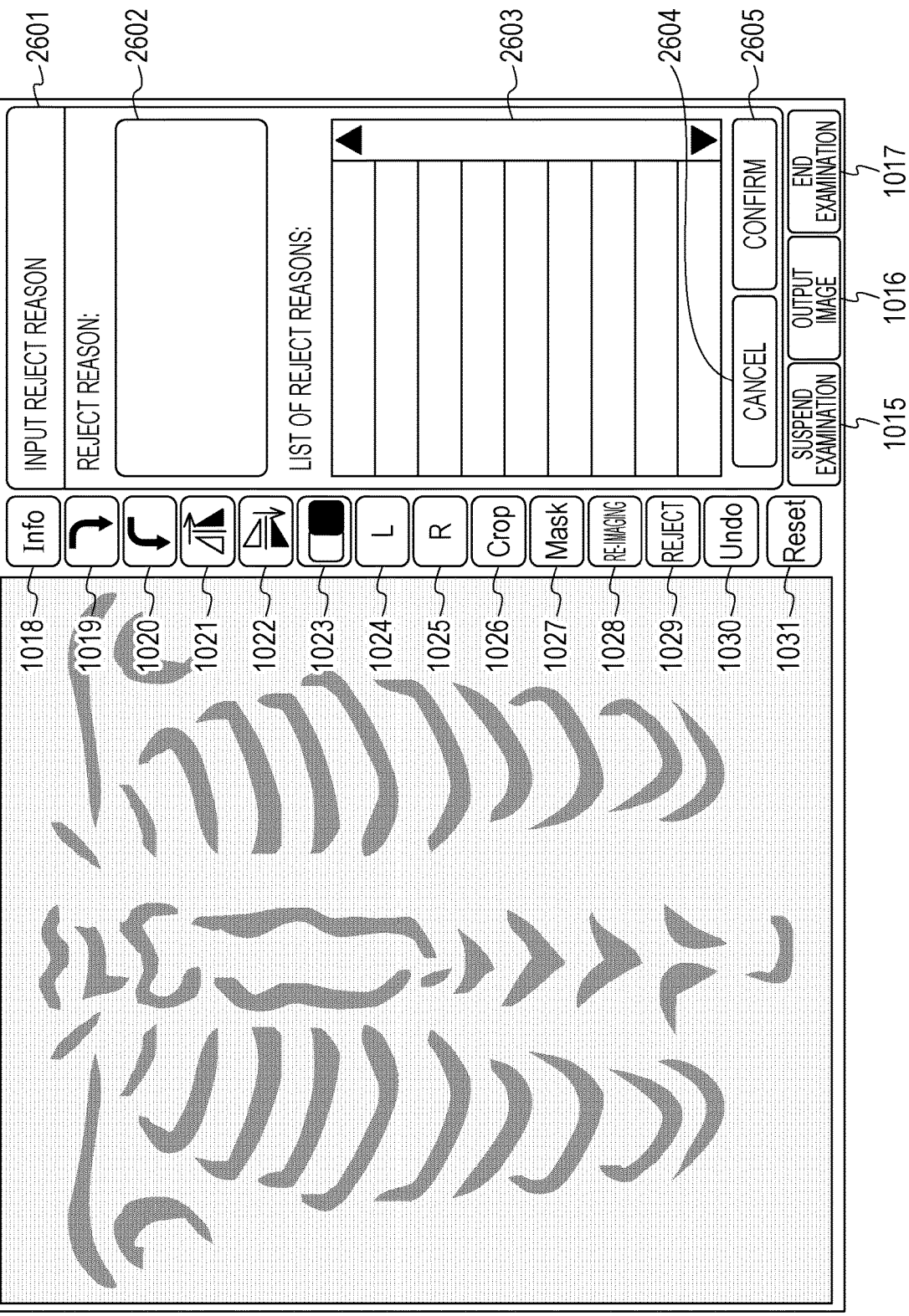
FIG. 26 is a diagram illustrating a reject reason input screen according to the embodiment of the present invention.

Here, an example of a reject reason input screen 2601 displayed in step S2503 in FIG. 25 is illustrated using FIG. 26. The reject input screen 2601 is displayed in a pop-up window on the imaging screen 1001 in an area that does not overlap the image display portion 1002. The reject input screen 2601 is a screen displayed when the re-imaging button 1028 or the reject button 1029 is pressed through an operation input while there is a captured image thumbnail 1011 that is in a selected state on the imaging screen 1001 illustrated in FIG. 10 or FIG. 24. Each of the captured image thumbnails 1011 is clicked through an operation input to the operation unit 108, thereby entering into the selected state. In the control of bringing one of the captured image thumbnails 1011 into the selected state, for example, the input of a click on the captured image thumbnail 1011 is detected by the input detection unit 4071, thereby allowing the examination control unit 406 to set the captured image thumbnail 1011 to the selected state. In this regard, the examination control unit 406 functions as a selection unit that selects at least one of the data of the projected image group and the data of the tomosynthesis image.

The reject button 1029 is a button (first button) for allowing the condition setting unit 4051 to execute a reject setting. The re-imaging button 1028 is a button (second button) for executing a re-imaging setting to set imaging information for executing re-imaging for the data selected by the condition setting unit 4051. In accordance with the re-imaging button being pressed, the condition setting unit 4051 executes a reject setting to set at least one of the data of the tomosynthesis image or the data of the projected image group as a reject. In addition to this, the condition setting unit 4051 executes a re-imaging setting to set imaging information for executing re-imaging for the data.

If a reject setting is made, the display control unit 4070 causes the captured image thumbnails 1011 indicating the data of the tomosynthesis image and the data of the projected image group to be displayed. In addition to this, the display control unit 4070 causes a mark indicating whether or not the corresponding image has been set as a reject by the condition setting unit 4051 to be displayed superimposed on each of the captured image thumbnails 1011. This allows each of the captured image thumbnails 1011 to intelligibly show whether or not the corresponding data is a reject. The display in FIG. 26 is not to be taken in a limiting sense, and the display control unit 4070 causes a mark (x) for an image when set as a reject or a circle (○) for an image not set as a reject to be displayed superimposed on each of the captured image thumbnails 1011. In the manner described above, a mark indicating whether or not the corresponding data has been set as a reject is displayed superimposed on each of the captured image thumbnails 1011, allowing intelligible showing of whether a reject has occurred or not.

In an imaging control device 107 according to one embodiment, in a case where, as in the imaging screen 1001 in FIG. 10, a captured image thumbnail 1011 corresponding to a projected image group is in the selected state, the display control unit 4070 causes both the reject button 1029 and the re-imaging button 1028 to be displayed. This enables the operator to select whether the projected image group is simply regarded as a reject or is regarded as a reject and then subjected to re-imaging, enabling output control and re-imaging to be easily executed in accordance with the situation.

Figure 28:
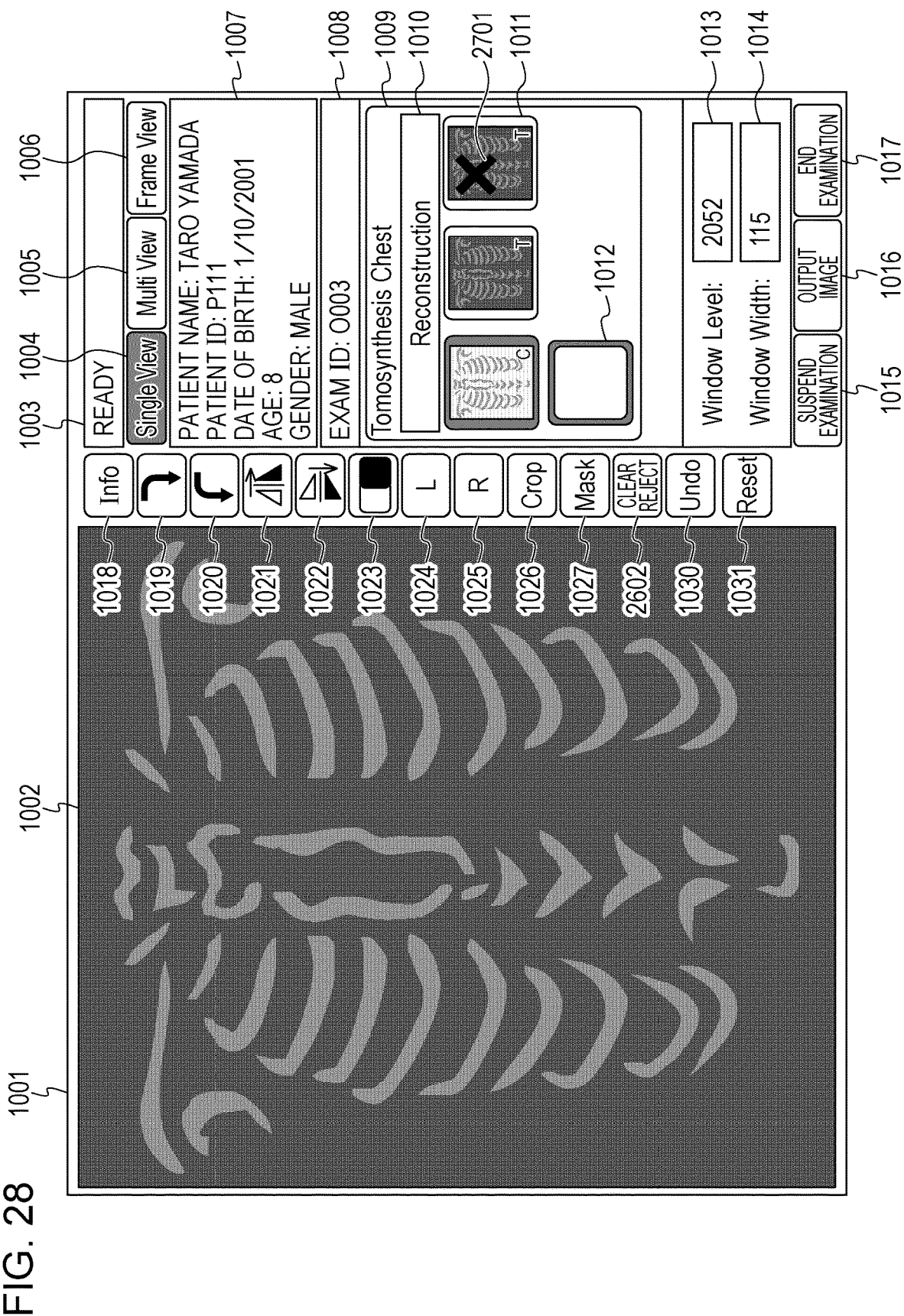
FIG. 28 is a diagram illustrating the imaging screen according to the embodiment of the present invention when a reject process is completed.

In contrast, as illustrated in FIG. 28, in a case where a captured image thumbnail 1011 corresponding to a tomosynthesis image is in the selected state, the display control unit 4070 makes the re-imaging button 1028 invisible. The reason for this is as follows. Since a tomosynthesis image obtained by reconstruction does not exactly have a concept of re-imaging, this point is clearly stated. Doing so enables the display control unit 4070 and the examination control unit 406 that controls the display control unit 4070 to execute control in which the execution of re-imaging setting is not permitted for a tomosynthesis image while the execution of re-imaging setting is permitted only for a projected image group. This is not to be taken in a limiting sense, and the examination control unit 406 may also cause the re-imaging button 1028 to be displayed when either of a tomosynthesis image and a projected image group is selected. Instead, the examination control unit 406 can perform control so that even if the re-imaging button 1028 is pressed, the corresponding process is not executed. Additionally, a similar purpose can be achieved by the display control unit 4070 causing the re-imaging button 1028 to be displayed as unselectable in a case where the data of the tomosynthesis image is in the selected state.

In another embodiment, in response to the re-imaging button 1028 being pressed while a tomosynthesis image is selected, the condition setting unit 4051 is configured to execute re-imaging for the tomosynthesis image. In this case, the condition setting unit 4051 generates new imaging information, and associates the new imaging information with the same examination information as the original imaging information. The new imaging information is displayed as, for example, an imaging technique display portion 1009b in FIG. 27, in parallel with an original imaging technique display portion 1009a by the display control unit 4070. Here, for the new imaging information, the condition setting unit 4051 makes the process conditions (reconstruction conditions and image processing conditions) for the tomosynthesis image identical to the process conditions for a tomosynthesis image that is in the selected state when the re-imaging is set. The new imaging information is also set to be identical to the imaging information (imaging technique information displayed in the imaging technique display portion 1009a) corresponding to the tomosynthesis image that is in the selected state described above. Doing so enables imaging to be efficiently re-executed in a case where, for example, the imaging has failed due to a motion of the object. The condition setting unit 4051 is also capable of changing the driving conditions included in the new imaging information (imaging technique), the irradiation conditions, and the image processing conditions for recursive processing or other processing to be performed on a projected image in accordance with the operation input of the operation unit 108. This can provide re-imaging to be executed in order to address an insufficient number of projected images or inappropriate irradiation conditions.

By doing so, in response to the irradiation switch 103 being pressed while new imaging information is selected, the imaging control unit 405 causes a projected image group corresponding to the new imaging information to be captured. In accordance with the completion of the capture of the projected image group, the imaging control unit 405 causes the image processing unit 110 to start a tomosynthesis image generation process, that is, a reconstruction process and tone conversion processing. In this case, the reconstruction processing unit 1611 executes a reconstruction process and tone conversion processing in accordance with the process conditions described above. Thus, the imaging control unit 405 performs control so that an analysis process is not executed by the tone conversion parameter acquisition unit 1612. By doing so, if the process conditions for tomosynthesis images are appropriate, re-imaging based on one of the tomosynthesis images can be executed for more appropriate imaging of projected images, which is efficient.

The reject button 1029 and the re-imaging button 1028 described above are displayed on the imaging screen 1001 together with the captured image thumbnails 1011 that are indications indicating the data of the tomosynthesis image and the data of the projected image group. This enables the operator to perform a reject setting and input a reject reason while viewing a preview of an image for the reject setting and the input of the reject reason, achieving the advantage of making it easy to study the reject reason.

The reject reason input screen 2601 is constituted by a reject reason input portion 2602, a reject reason selection portion 2603, a cancellation instruction portion 2604, and a confirmation instruction portion 2605. The reject reason input portion 2602 is a control for inputting a reject reason. The reject reason selection portion 2603 is a control for displaying reject reasons registered in the control unit 111 in list form. When a reject reason is selected from the list, the selected reject reason is input to the reject reason input portion 2602. As reject reasons, reject reasons confirmed through system settings in advance and confirmed through the reject reason input screen 2601 in the past are registered. The cancellation instruction portion 2604 is a button for providing an instruction to discard an input reject reason. In accordance with a cancellation instruction, the content of the input reject reason is discarded and the reject reason input screen 2601 is closed. The screen confirmation instruction portion 2605 is a button for providing an instruction to confirm a reject reason. In accordance with a confirmation instruction, the content of an input reject reason is confirmed and the reject reason input screen 2601 is closed. The reject reason input screen 2601 having the configuration described above is displayed.

When the content of an input reject reason is confirmed, the condition setting unit 4051 sets, as a reject, the data corresponding to the captured image thumbnail 1011 that is in the selected state.

Figure 27:
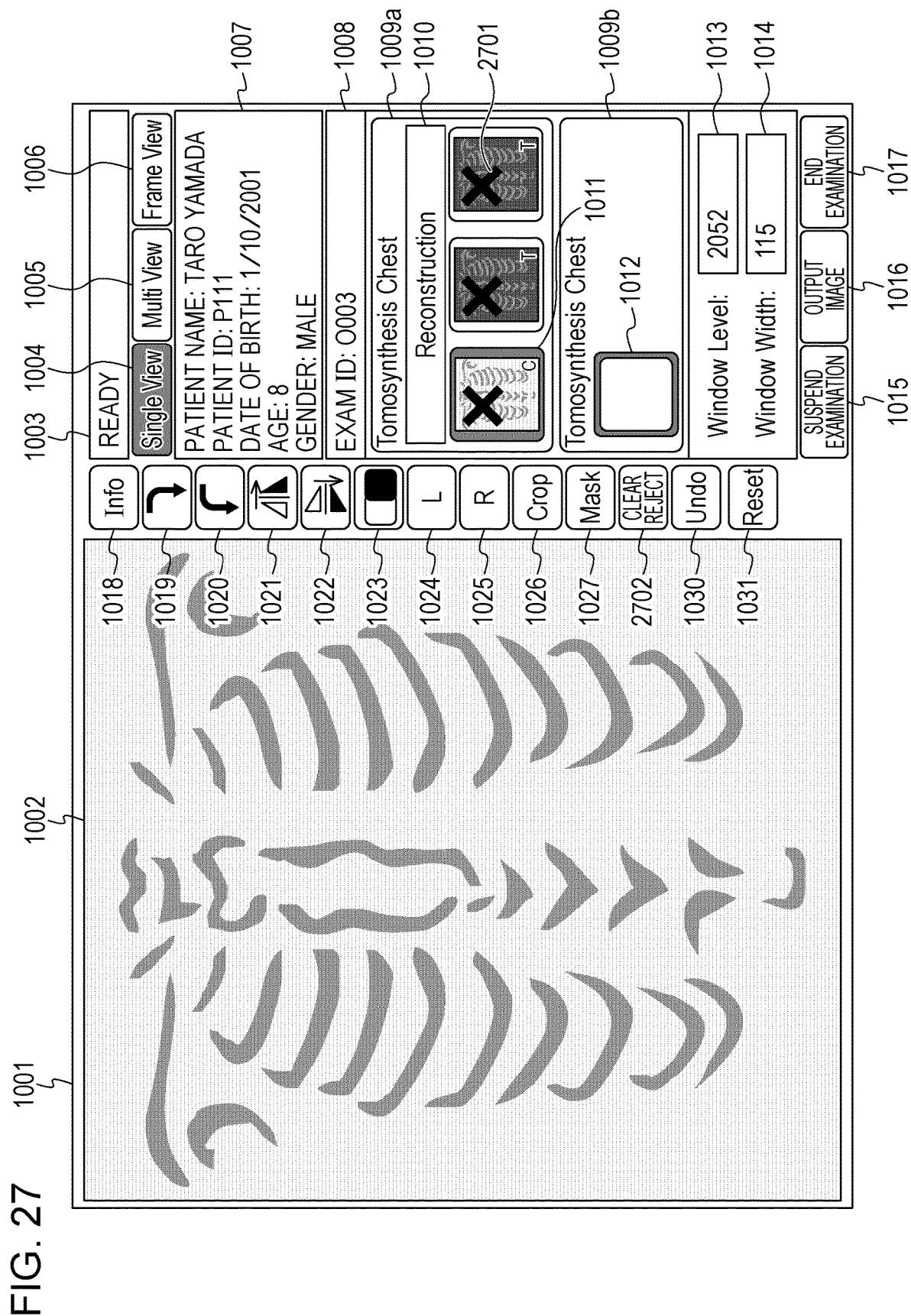
FIG. 27 is a diagram illustrating the imaging screen according to the embodiment of the present invention when a re-imaging process is completed.

Here, an example of the imaging screen 1001 displayed when the re-imaging process for a tomosynthesis imaging technique is completed in step S2513 in FIG. 25 is illustrated using FIG. 27. When the re-imaging process for the tomosynthesis imaging technique is completed, the reject marks 2701 are respectively displayed on all the captured image thumbnails 1011 included in the imaging technique display portion 1009a for the tomosynthesis imaging technique for which the re-imaging process has been executed. The form of the reject marks 2701 is not limited so long as it is possible to recognize a reject state. In addition, the same imaging technique display portion 1009b as the tomosynthesis imaging technique for which the re-imaging process has been executed is added immediately below the imaging technique display portion 1009a. Thereafter, the imaging technique display 1009b is selected as intended for the next imaging, and the intended-for-imaging thumbnail 1012 is displayed in the imaging technique display 1009b. Further, in a case where a captured image thumbnail 1011 of a projected image included in the tomosynthesis imaging technique for which re-imaging has been executed is selected as a preview, the re-imaging button 1029 becomes invisible and the display area is cut out from the display. Further, in a case where a captured image thumbnail 1011 for which the reject process has been executed is displayed as a preview, the reject button 1029 becomes invisible and a reject clearance instruction portion 2702 is displayed in the same display area as that of the reject button 1029. The reject clearance instruction portion 2702 is a button for providing an instruction to clear the setting of the reject for the image subjected to the reject setting, which is currently being selected as a preview. When the reject process is canceled, the reject setting included in the image information is switched to OFF. The imaging screen 1001 having the configuration described above is displayed.

Here, an example of the imaging screen 1001 displayed when the reject process is completed in step S2514 in FIG. 25 is illustrated using FIG. 28. When the reject process is completed, the reject mark 2701 is displayed only on the captured image thumbnail 1011 of the image for which the reject process has been executed. The imaging screen 1001 having the configuration described above is displayed.

Additionally, in addition to the embodiments described above, for example, if one or a plurality of tomosynthesis images are present in first imaging information displayed in the imaging technique display portion 1009a, the display control unit 4070 executes the following process. That is, in response to all the tomosynthesis images being set as rejects, the display control unit 4070 is configured to display at least either a warning or an indication asking whether or not to execute the reconstruction of a new tomosynthesis image. Since tomosynthesis imaging is originally performed in order to obtain a tomosynthesis image, if all the generated tomosynthesis images are regarded as rejects, it is considered that the intended purpose of the imaging is not achieved. Accordingly, as described above, the display of a warning or a GUI for prompting re-imaging can help perform tomosynthesis imaging as appropriate. In the example described above, the setting of all the tomosynthesis images as rejects is used as a trigger, but is not limited thereto. For example, in a case where there are three tomosynthesis images, a specified number of tomosynthesis images or more, for example, two or more tomosynthesis images, may be set as rejects. Alternatively, each time one tomosynthesis image is set as a reject, the display described above may be provided.

In addition, taking it into account that a projected image group or tomosynthesis image group includes a plurality of images, the condition setting unit 4051 is capable of setting some of the projected images included in the projected image group as rejects (executing a first setting). Alternatively, the condition setting unit 4051 is capable of setting some of a plurality of slice images included in a tomosynthesis image as rejects (executing a second setting). For example, if only some projected images have a problem due to a motion of the body or any other effect, such projected images are set as rejects, thereby contributing to the generation of a more appropriate tomosynthesis image. In addition, if some slice images of a tomosynthesis image are inappropriate, such projected images are set as rejects, which can support more accurate diagnosis.

In response to the first setting described above being performed, the reconstruction processing unit 1611 executes a reconstruction process based on projected images except for some projected images for which the first setting has been made. By doing so, if an inappropriate projected image is found, a tomosynthesis image on which the effect of the inappropriate projected image is eliminated is automatically generated, which can provide efficient support for imaging. Similarly to the example described above, if there is a tomosynthesis image reconstructed by using the projected images set as rejects, the condition setting unit 4051 sets the image as a reject, thereby preventing an inappropriate tomosynthesis image from being used for diagnosis. In addition, the image processing unit 110 prohibits the generation of an oblique image in a direction with respect to the direction of irradiation for the projected images, or the display control unit 4070 performs control to prohibit the display of the oblique image. For example, projected images with an irradiation direction of −25 degrees to −20 degrees are set as rejects. In this case, a range smaller than −20 degrees is eliminated from a display range of oblique images, yielding a range of ±20 degrees, or only a range of −25 degrees to −20 degrees is eliminated.

In another exemplary embodiment, instead of immediately generating a tomosynthesis image or performing a reject setting in accordance with some projected images being set as rejects, the reconstruction processing unit 1611 defers the judgment to the operator. In accordance with the first setting being performed, the display control unit 4070 enables the display of a GUI for providing an instruction as to whether or not to execute a reconstruction process based on a projected image group in which some projected images have been set as rejects, or a message which recommends the execution of the reconstruction process. Alternatively, a message indicating that a tomosynthesis image based on the projected image group in which some projected images have been set as rejects is present can be displayed. Any combination of them can also be displayed. Doing so can prevent an unnecessary reconstruction process or reject process from being performed, and can improve imaging efficiency.

The advantages of processes according to one of the embodiments described above will be described. In a case where a plurality of tomosynthesis images are reconstructed from the same projected image, if the original projected image is subjected to a reject process, the tomosynthesis images can probably be regarded as rejects in most cases. This probability is higher when a re-imaging instruction for re-performing imaging is given. Thus, if a projected image is subjected to a reject process later, it may be time and labor consuming to further execute a reject process on other tomosynthesis images one by one. Further, if it is required that a reject reason be input when a reject process is executed, it is also necessary to input a reject reason for each image. Accordingly, a reject process is easily executed for a tomosynthesis imaging technique and the ON/OFF setting of the image output is enabled, thereby reducing the load imposed on the operator. Meanwhile, as described above, a reject process is associated with ON/OFF of the image external output target. This enables a reject process to be individually performed on an image simply judged not to have to be output to outside in addition to an image for which imaging or reconstruction has failed, in which case control can be performed so that, in response to a reject process being performed on one image, other images are also subjected to a reject process accordingly.

<Other Embodiments>

In the example described above, an embodiment of an X-ray imaging system has been illustrated, but is not limited thereto. Devices capable of tomosynthesis imaging or tomographic imaging, such as MRI, PET, and SPECT, or an image management device or an image processing device that handles images from such devices may implement the present invention.

As an alternative, any combination of the embodiments described above is also included in embodiments of the present invention. Alternatively, in a case where the processes described above are executed in cooperation of a program with hardware, the program or a storage medium storing the same is also included in an embodiment of the present invention. An embodiment of a program is implemented by a program for the processes described above, and by storing the program in a storage unit, loading the program onto a RAM by using a CPU of an electronic calculator or a computer, and executing instructions included in the program by using the CPU.

In respect of the additional display control of an icon described with reference to FIGS. 23 and 24, in another embodiment, even when the conditions for creating a new icon described above are satisfied, it is possible to switch between a setting for immediately creating an icon and a setting for not immediately creating an icon but creating or displaying an icon after, for example, the authentication of a user. Information indicating such settings is stored in a memory of the imaging control device 107 by the control unit 111. Such settings can be changed through the operation input of the operation unit 108.

In a case where the setting for not immediately creating an icon is made, before step S2310 and S2311 in FIG. 23, the display control unit 4070 causes the display of a window for selecting, through an operation input, whether or not to cause the display unit to display a new icon representing a tomographic image based on changed or set conditions. This window shows a first icon or button used to accept an operation input for display, and a second icon or button used to accept an operation input for not display, together with a message asking the user about selection. If an operation input for the first icon is made, the display control unit 4070 executes an icon addition display process corresponding to step S2310 or S2311. If an operation input for the second icon is made, the processes of steps S2310 and S2311 to S2313 are not performed. Doing so can provide user-desired control for icon display.

In another embodiment, the case of displaying an icon, the case of displaying a newly added icon instead of one icon selected by the user, and the case of adding no icons may be switched over. Such switching is enabled by a setting for displaying a newly added icon instead of one icon selected by the user, and, while this setting is made, the display control unit 4070 causes a new icon to be displayed instead of a selected single icon in accordance with the operation input to the operation unit 108 by the user. In another example, furthermore, the window described above shows a third icon or button used to accept an operation input for the display of a newly added icon instead of one icon selected by the user. In accordance with the operation input for the third icon and an operation input for selecting the one icon corresponding to a thumbnail, the display control unit 4070 causes a new icon to be displayed instead of the selected single icon. In this embodiment, in a case where a set of tomographic images before the change is not necessary, such as in the case where the reconstruction conditions or image processing conditions have been finely corrected, no unnecessary thumbnail is displayed, which can facilitate the management of reconstructed tomographic images. However, even if conditions are finely corrected, a tomographic image before the change and a tomographic image after the change are used for diagnoses for different purposes, which is useful for the transfer of both tomographic images to the PACS 115.

In another embodiment, even if it is determined in step S2306 that the reconstruction parameters and the image processing parameters are identical, as described above, a GUI for prompting the user to select whether or not to add an icon is displayed. This function is useful for the separate management of, for example, a tomographic image to be transferred to the PACS 115, a tomographic image to be transferred to the printer 117, and a tomographic image to be transferred to a workstation (not illustrated). For example, one conceivable case is that different ranges are cropped from tomographic images obtained under the same conditions, and are output.

In another embodiment, in a case where the same reconstruction conditions as those for an already reconstructed tomographic image have been set, a confirmation button 1121 is prevented from being pressed. This process is executed by performing the processes of steps S2302 to S2309 in accordance with the reconstruction conditions displayed in FIG. 22 before the confirmation button 1121 is pressed. This can reduce the reconstruction of an unnecessary tomographic image or the display of a thumbnail.

Figure 29:
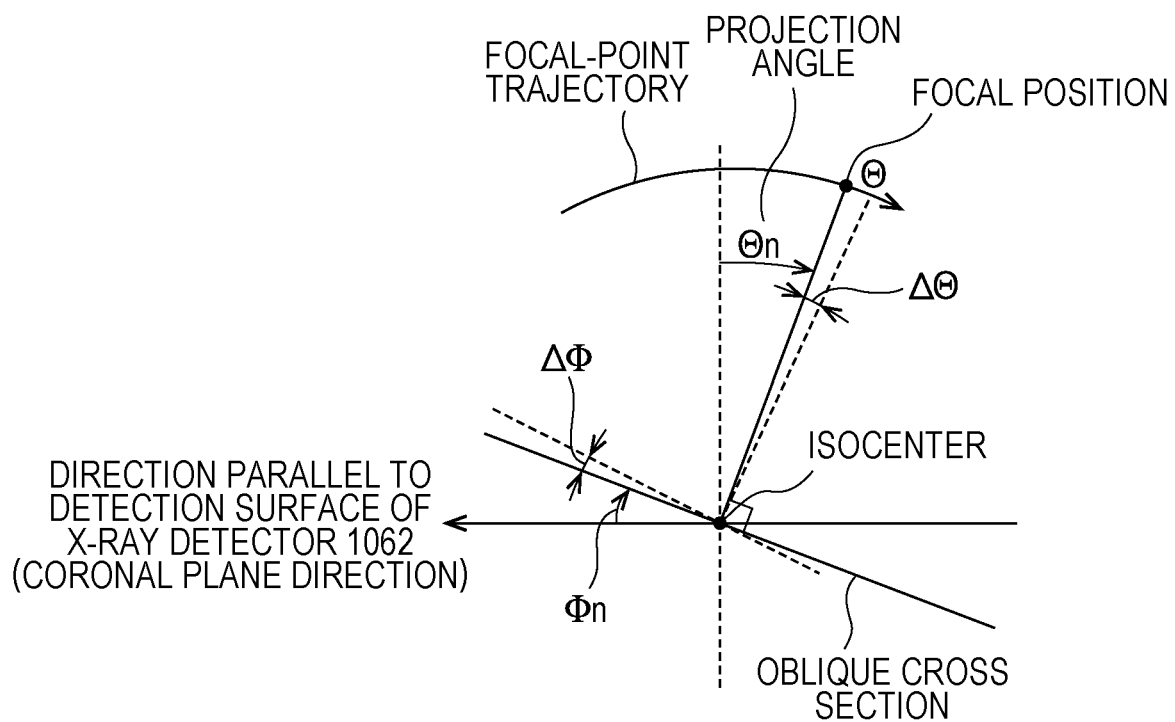
FIG. 29 is a diagram illustrating an example relationship between projection angles of projected images and oblique cross sections according to an embodiment.

Another embodiment will be described with reference to FIG. 29. The control unit 111 controls an angle interval $\Delta\Phi$ of oblique cross-sectional images O which are adjacent for the display of oblique cross-sectional images on the basis of an interval $\Delta\Theta$ of projection angles at which projected images P are captured (in the imaging system in FIG. 2, angles from $-XX$ deg. to $+XX$ deg.). Consideration is given to the case where, while the projection angle is changed over a range from the projection angle $-XX$ deg. to the projection angle $+XX$ deg., X-ray irradiation is performed N times to obtain N projected images P. The difference between the projection angle $\Theta n$ for the n-th ($n<N-1$) X-ray irradiation and the projection angle $\Theta n+1$ for the (n+1)-th X-ray irradiation is defined as $\Delta\Theta$. $\Delta\Theta$ may be constant regardless of n, or may be different for each n. Even if $\Delta\Theta$ is controlled to be constant regardless of n, resulting projected images may not exactly match due to any error caused by a motor and the like. For example, variations with errors less than or equal to 5% of $\Delta\Theta$ may be handled as identical.

The value of $\Delta\Theta$ may be calculated based on $\Theta n$. The value of $\Theta n$ is acquired from the X-ray control unit 104 or the movement mechanism control unit 1063 as geometric information for each projected image. Alternatively, the value of $\Delta\Theta$ may be directly acquired from the X-ray control unit 104 or the movement mechanism control unit 1063.

In one embodiment, if $\Delta\Theta$ is constant, the angle interval of oblique cross-sectional images is given by $\Delta\Phi=\Delta\Theta$, and serves as an angle interval over which oblique cross sections are sequentially displayed. For example, the mouse cursor is placed over the 3D slider in FIG. 12 or the 3D slider is selected to be in focus. In this case, it is assumed that an oblique cross-sectional image On oriented at an angle of $\Phi n$ with respect to the coronal plane (the detection surface of the X-ray detector) is being displayed. In this state, the up-arrow key on the keyboard is pressed once, thereby displaying an oblique cross-sectional image On+1 with an angle $\Phi n+1$ with respect to the coronal plane, which is given by $\Phi n+1-$ Φn=ΔΦ=ΔΘ. In this case, desirably, Φn=Θn. By doing so, the oblique image ○ is an image of a cross section in an irradiation direction Θ which is the normal direction, resulting in an increase in the quality of the oblique image. Even if Φn=Θn is not satisfied, reducing Δ of Φn=Θn±Δ to 25 percent or less of ΔΘ can reduce the difference between Φn and Θn, achieving the advantage of improving image quality compared to the case of exceeding 25%. Even if ΔΘ is not constant, making ΔΘn and ΔΦn identical or reducing the difference between Φn and Θn can improve image quality.

In another embodiment, the control unit 111 causes the display of an oblique image of a cross section not passing through the isocenter. While an image of a cross section not passing through the isocenter provides improved quality for a tomosynthesis image, in some cases, a cross-sectional image passing through the isocenter may not necessarily be an image suitable for observation since the operator may wish to observe a fracture at a specific position in a specific direction, for example. For example, if a setting for displaying an oblique image of a cross section not passing through the isocenter is made, the display control unit 111 causes such an oblique image to be displayed, whereas if a setting for displaying an oblique image of a cross section not passing through the isocenter is not made, the display control unit 111 does not cause such an oblique image to be displayed. The setting information is stored in the memory of the imaging control device 107, and can be changed by a user in accordance with an operation through the operation unit 108. For an oblique image of a cross section not passing through the isocenter, which is displayed when a setting for displaying an oblique image of a cross section not passing through the isocenter is made, as described in the embodiment described above, the angle Φ with respect to the coronal plane is set to be equal to any of the projection angles θ of the projected images P, whereby the image quality can be guaranteed to some extent.

In another embodiment, consideration is given to the case where some of a plurality of projected images are designated as rejects. In this case, the control unit 111 controls image processing on the basis of position information corresponding to projected images set as rejects. For example, consideration is given to the case where, while the projection angle is changed over a range from the projection angle −XX deg. to the projection angle +XX deg., X-ray irradiation is performed N times to obtain N projected images Pn (n≤N). For example, a projected image at or around the lower limit or upper limit of the projection angle, such as any of P1 to P3 or any of PN-2 to PN, is designated as a reject. In this case, the image processing unit 110 performs reconstruction by using (N-6) projected images in total, namely, P4 to PN-3. In this case, similar consideration to the case where the range of projection angles is initially narrowed to a small range may apply. That is, this tomosynthesis is similar to that in which the X-ray generation unit performs imaging while being moved over a range of θ4 to θN-3, where θ4 denotes the projection angle for P4 and θN-3 denotes the projection angle for PN-3.

In the manner described above, even if some of a plurality of projected images are designated as rejects, a reconstructed image is not regarded as a reject and reconstruction is re-performed by using projected images that are not rejects, which can provide effective use of data obtained through X-ray irradiation.

Needless to say, as mentioned in the exemplary embodiment described above, the display of oblique cross-sectional images is limited on the basis of the projection angles. Accordingly, if the display of an intended oblique cross-sectional image is not available, re-imaging is performed. Here, for example, a certain oblique cross-sectional image is designated as an image for PACS transfer. In this case, if some projected images of a projected image group that is data on which the oblique cross-sectional image is based are designated as rejects and the display of the oblique cross-sectional image is limited, three-dimensional volume data (tomographic images) including the oblique cross-sectional image may be set as a reject in accordance with the projected images of the projected image group being designated as rejects. Alternatively, in accordance with the projected images of the projected image group being designated as rejects, the display control unit 4070 may cause the display of a dialog asking the user whether or not the three-dimensional volume data (tomographic images) is regarded as a reject, so that the designation of a reject is deferred to the operation input of the user. If there is an operation input indicating that the three-dimensional volume data is designated as a reject, the control unit 110 designates the three-dimensional volume data as a reject and cancels the designation of the oblique cross-sectional image as that for PACS transfer. Alternatively, the cancellation of PACS transfer may be deferred to the operation input of the user. If there is no operation input indicating that the three-dimensional volume data is designated as a reject, the control unit 110 does not designate the three-dimensional volume data as a reject nor does the control unit 110 cancel the PACS transfer designation. The oblique cross-sectional image is output to the PACS 115 through the communication circuit 112.

In the manner described above, if some of projected images are designated as rejects, whether or not a reconstructed tomographic image is also regarded as a reject accordingly is deferred to the operation input of the user, thereby executing the user-desired processing and reducing the labor for operation input. In addition, since the designation as PACS transfer can also be canceled along with reject designation, the labor for the processing can be reduced.

Consideration is now given to the case where a projected image PN' has been designated as a reject, where N' is an integer satisfying N'=N/2. In this case, a projected image obtained by X-rays emitted from the X-ray generation unit 102 at a position almost immediately above the isocenter or at the position with a projection angle of approximately 0° is not able to be used for reconstruction. In this case, the image processing unit 110 does not re-perform reconstruction of a tomographic image since image quality is not sufficiently guaranteed.

In another embodiment, there is no significant problem if only one projected image at a projection angle of 0° is not able to be used for reconstruction, and accordingly the image processing unit 110 performs reconstruction by using projected images except for the projected image designated as rejects, which can provide effective use of data obtained by X-ray imaging. In this case, the image processing unit 110 is configured to perform reconstruction if, for example, the number of available projected images does not exceed M that is a threshold value, and not to perform reconstruction if M is exceeded.

In the manner described above, the control unit 111 controls whether or not to perform reconstruction in accordance with position information on the projected images designated as rejects, the projection angle, or the number of projected images, or a combination of them. This prevents the reconstruction of a tomographic image whose image quality is not guaranteed while providing effective use of data obtained by X-ray irradiation, leading to less likelihood of false diagnosis.

In the example described above, a description has been given of the case where projected images are designated as "rejects". In the exemplary embodiment described above, by way of example, the term "reject" refers to, but is not limited to, failed imaging, which is decided on through the operation input of the user. For example, similar processing may also be performed on, an image determined as a defective image by the image processing unit 110.

As an alternative, in step S608 described above, the display control unit 4070 causes the display unit 109 to sequentially display projected images upon sequentially receiving the projected images during the capture of projected images. This enables the user to make sure that successively captured projected images have no problem during imaging. In accordance with the completion of the capture of projected images in step S608, the image processing unit 110 executes a reconstruction process. In accordance with the completion of the reconstruction, the display control unit 4070 displays a tomosynthesis image obtained through the reconstruction on the display unit 109. The series of processes described above is controlled by the imaging control unit 405. Accordingly, a reconstruction process is performed in accordance with the completion of the capture of projected images, enabling a quick check of tomosynthesis images.

In the manner described above, the display of projected images during the capture of projected images helps the user easily check a problem regarding the capture of projected images. Quick display of a tomosynthesis image after the completion of the capture of projected images helps the user easily make sure that there is no problem in reconstruction. This facilitates checking whether or not re-imaging is necessary on the basis of both projected images and a reconstructed image.

In the embodiment described above, for example, the functions of the imaging control device 107 may be distributed to a plurality of devices capable of communicating with each other, thereby implementing the functions of the imaging control device 107 as a control system. For example, the functions of the image processing unit 110 may be provided for an external server, by way of example. The external server may be located in a control room or an imaging room where an X-ray imaging system for performing tomosynthesis imaging is installed, and may be connected via a dedicated LAN. The external server may also be located in the hospital, and may perform communication over a LAN in the hospital. Alternatively, the external server may be located in a data center or the like outside the hospital either locally or overseas, and data may be exchanged via secure communication methods such as VPN.

The present invention is not limited to the embodiments described above, and a variety of changes and modifications can be made without departing from the spirit and scope of the present invention. Therefore, to apprise the public of the scope of the present invention, the following claims are provided.

This application claims the benefit of Japanese Patent Application No. 2013-127975 filed Jun. 18, 2013, which is hereby incorporated by reference herein in its entirety.

The invention claimed is:

1. A control device for controlling tomosynthesis imaging for obtaining a tomosynthesis image from a projected image group captured by irradiating an object with X-rays from a plurality of different angles by using an X-ray generation unit and an X-ray detection unit, the control device comprising:
    one or more processors which, by executing instructions, cause the control device to function as:
    a setting unit that sets at least one of projected images of the projected image group as a reject,
    wherein the setting unit sets the tomosynthesis image generated by reconstruction using the projected image group including the at least one of the projected images set as the reject, as a reject;
    a communication circuit that transmits at least either of a tomosynthesis image and the projected image group to an external device;
    an output control unit for limiting transmission of data set as a reject to the external device; and
    a display control unit that causes an indication indicating each of the tomosynthesis image and the projected image group to be displayed and further causes a mark indicating whether or not the corresponding at least one of the projected images has been set as a reject by the setting unit to be superimposed on the indication,
    wherein the display control unit causes an indication corresponding to the at least one of the projected images set as a reject by the setting unit to have superimposed thereon a mark indicating that the at least one of the projected images has been set as a reject,
    wherein
    the display control unit causes first imaging information for capturing a projected image group to be displayed in a first display area, and, in response to the projected image group corresponding to the first imaging information being captured, causes a thumbnail image indicating the projected image group to be displayed in the first display area, and
    in response to a tomosynthesis image based on the projected image group being generated, the display control unit causes a thumbnail image of the tomosynthesis image to be displayed in the first display area.

2. The control device according to claim 1, wherein the setting unit executes a reject setting to set at least one of the tomosynthesis image or the projected image group as a reject, and a re-imaging setting to set imaging information for executing re-imaging for the tomosynthesis image or the projected image group.

3. The control device according to claim 2, wherein the one or more processors which, by executing the instructions, further cause the control device to function as a control unit that performs control so that execution of the re-imaging setting is permitted for the projected image group and execution of the re-imaging setting is not permitted for the tomosynthesis image.

4. The control device according to claim 1, wherein the one or more processors which, by executing the instructions, further cause the control device to function as:
    a selection unit that selects a process condition of a tomosynthesis image corresponding to the first imaging information; and
    an image processing unit that processes, in response to the selection, a tomosynthesis image corresponding to second imaging information different from the first imaging information in accordance with the selected process condition.

5. The control device according to claim 1, wherein the one or more processors which, by executing the instructions, further cause the control device to function as a display control unit that causes a first button for setting the reject to be displayed together with an indication indicating each of the tomosynthesis image and the projected image group.

6. The control device according to claim 5, wherein the display control unit causes a first button for setting a reject, and a second button for setting a reject and providing an instruction to perform re-imaging to be displayed together with an indication indicating each of the tomosynthesis image and the projected image group.

7. The control device according to claim 6, wherein the one or more processors which, by executing the instructions, further cause the control device to function as a selection unit that selects at least one of the projected image group or the tomosynthesis image, wherein
the display control unit enables pressing of the first and second buttons while the projected image group is being selected, and disables pressing of the second button while the tomosynthesis image is being selected.

8. The control device according to claim 6, wherein the display control unit makes the first and second buttons visible while the projected image group is being selected, and makes the second button invisible while the tomosynthesis image is being selected.

9. The control device according to claim 6, wherein in response to the second button being pressed, the setting unit executes a reject setting to set at least one of the tomosynthesis image or the projected image group as a reject, and a re-imaging setting to set imaging information for executing re-imaging for the tomosynthesis image or the projected image group.

10. The control device according to claim 1, wherein the one or more processors which, by executing the instructions, further cause the control device to function as a display control unit that causes at least either a warning or an indication asking whether or not to execute reconstruction of a new tomosynthesis image to be displayed in response to a specified number of tomosynthesis images or more being set as a reject for at least one tomosynthesis image corresponding to the first imaging information.

11. The control device according to claim 1, wherein the setting unit executes either of a first setting for setting a certain projected image included in the projected image group as a reject and a second setting for setting a certain slice image included in the tomosynthesis image as a reject.

12. The control device according to claim 11, wherein the one or more processors which, by executing the instructions, further cause the control device to function as a reconstruction unit that executes, in accordance with the first setting been executed, a reconstruction process based on projected images except for the certain projected image for which the first setting has been made.

13. The control device according to claim 12, wherein the one or more processors which, by executing the instructions, further cause the control device to function as a display control unit that causes a display unit to display, in accordance with the first setting being performed, at least any one of a GUI for providing an instruction as to whether or not to execute a reconstruction process based on a projected image group in which the certain projected image has been set as a reject, a message which recommends execution of the reconstruction process, and a message indicating that a tomosynthesis image based on the projected image group in which the certain projected image has been set as a reject is present.

14. An X-ray imaging apparatus comprising:
the control device according to claim 1; and
the X-ray detector.

15. An X-ray imaging system comprising:
the control device according to claim 1;
the X-ray detector;
the X-ray generation unit; and
the display unit.

16. The control device according to claim 1, wherein the one or more processors which, by executing the instructions, further cause the control device to function as a limitation unit that, in accordance with the number of projected images designated as rejects or a projection angle corresponding to the projected images within the projected image group, limits reconstruction based on a projected image not designated as a reject within the projected image group.

17. A control device for controlling tomosynthesis imaging for obtaining a tomosynthesis image from a projected image group captured by irradiating an object with X-rays from a plurality of different angles by using an X-ray generation unit and an X-ray detection unit, the control device comprising:
one or more processors which, by executing instructions, causes the control device to function as:
a selection unit that selects at least one of the projected image group or the tomosynthesis image;
an instruction unit that executes at least any one of a first instruction for providing an instruction to set the selected tomosynthesis image or the projected image group as a reject, and a second instruction for providing an instruction to re-acquire the selected tomosynthesis image or the projected image group;
a setting unit that, in a case where the selected tomosynthesis image or the projected image group indicates the projected image group, sets the projected image group as a reject in response to the first instruction having been given, and sets the projected image group and the tomosynthesis image based on the projected image group as rejects in response to the second instruction having been given;
a communication circuit that transmits at least either a tomosynthesis image and the projected image group to an external device;
an output control unit for limiting transmission of data set as a reject to the external device; and
a display control unit that causes an indication indicating each of the tomosynthesis image and the projected image group to be displayed and further causes a mark indicating whether or not the corresponding at least one of the projected images has been set as a reject by the setting unit to be superimposed on the indication,
wherein the display control unit causes an indication corresponding to the at least one of the projected images set as a reject by the setting unit to have superimposed thereon a mark indicating that the at least one of the projected images has been set as a reject,
wherein
the display control unit causes first imaging information for capturing a projected image group to be displayed in a first display area, and, in response to the projected image group corresponding to the first imaging information being captured, causes a thumbnail image indicating the projected image group to be displayed in the first display area, and
in response to a tomosynthesis image based on the projected image group being generated, the display control unit causes a thumbnail image of the tomosynthesis image to be displayed in the first display area.

18. A control method for controlling tomosynthesis imaging for obtaining a tomosynthesis image from a projected image group captured by irradiating an object with X-rays from a plurality of different angles by using an X-ray generation unit and an X-ray detection unit, the control method comprising:

a setting step of setting at least one of projected images of the projected image group as a reject, wherein the setting step sets the tomosynthesis image generated by reconstruction using the projected image group including the at least one of the projected images set as the reject, as a reject, a step of limiting transmission of data set as a reject to an external device, and a display control step of causing an indication indicating each of the tomosynthesis image and the projected image group to be displayed and further causing a mark indicating whether or not the corresponding at least one of the projected images has been set as a reject by the setting step to be superimposed on the indication, wherein the display control step causes an indication corresponding to the at least one of the projected images set as a reject by the setting step to have superimposed thereon a mark indicating that the at least one of the projected images has been set as a reject, wherein the display control step causes first imaging information for capturing a projected image group to be displayed in a first display area, and, in response to the projected image group corresponding to the first imaging information being captured, causes a thumbnail image indicating the projected image group to be displayed in the first display area, and in response to a tomosynthesis image based on the projected image group being generated, the display control step causes a thumbnail image of the tomosynthesis image to be displayed in the first display area.

19. A control method for controlling tomosynthesis imaging for obtaining a tomosynthesis image from a projected image group captured by irradiating an object with X-rays from a plurality of different angles by using an X-ray generation unit and an X-ray detection unit, the control method comprising:

a step of selecting at least one of the projected image group or the tomosynthesis image;

a step of providing at least any one of a first instruction for providing an instruction to set the selected tomosynthesis image or the projected image group as a reject, and a second instruction for providing an instruction to re-acquire the selected tomosynthesis image or the projected image group;

a step of, in a case where the selected tomosynthesis image or the projected image group indicates the projected image group, setting the projected image group as a reject in response to the first instruction having been given, and setting the projected image group and the tomosynthesis image based on the projected image group as rejects in response to the second instruction having been given;

a step of limiting transmission of data set as a reject to an external device; and a step of display control that causes an indication indicating each of the tomosynthesis image and the projected image group to be displayed and further causes a mark indicating whether or not the corresponding at least one of the projected images has been set as a reject by the step of setting to be superimposed on the indication, wherein the step of display control causes an indication corresponding to the at least one of the projected images set as a reject by the step of setting to have superimposed thereon a mark indicating that the at least one of the projected images has been set as a reject, wherein the step of display control causes first imaging information for capturing a projected image group to be displayed in a first display area, and, in response to the projected image group corresponding to the first imaging information being captured, causes a thumbnail image indicating the projected image group to be displayed in the first display area, and in response to a tomosynthesis image based on the projected image group being generated, the step of display control causes a thumbnail image of the tomosynthesis image to be displayed in the first display area.

20. A non-transitory computer readable storage medium storing a program for causing a computer to execute a control method for controlling tomosynthesis imaging for obtaining a tomosynthesis image from a projected image group captured by irradiating an object with X-rays from a plurality of different angles by using an X-ray generation unit and an X-ray detection unit, the control method comprising:

a setting step of setting at least one of projected images of the projected image group as a reject;

a limiting step of limiting transmission of data set as a reject to an external device, wherein the setting step sets the tomosynthesis image generated by reconstruction using the projected image group including at least one of the projected images set as the reject; and a display control step that causes an indication indicating each of the tomosynthesis image and the projected image group to be displayed and further causes a mark indicating whether or not the corresponding at least one of the projected images has been set as a reject by the setting step to be superimposed on the indication, wherein the display control step causes an indication corresponding to the at least one of the projected images set as a reject by the setting step to have superimposed thereon a mark indicating that the at least one of the projected images has been set as a reject, wherein the display control step causes first imaging information for capturing a projected image group to be displayed in a first display area, and, in response to the projected image group corresponding to the first imaging information being captured, causes a thumbnail image indicating the projected image group to be displayed in the first display area, and in response to a tomosynthesis image based on the projected image group being generated, the display control step causes a thumbnail image of the tomosynthesis image to be displayed in the first display area.

* * * * *